US009192520B2

(12) United States Patent
Cater et al.

(10) Patent No.: US 9,192,520 B2
(45) Date of Patent: Nov. 24, 2015

(54) EYEWEAR HAVING MULTIPLE VENTILATION STATES

(71) Applicant: Oakley, Inc., Foothill Ranch, CA (US)

(72) Inventors: Joel Cater, Ketchum, ID (US); Josh Gallegos, Corona, CA (US); David Ginther, Ladera Ranch, CA (US); Jason Hutchison, San Clemente, CA (US); Aaron Taylor, Hailey, ID (US)

(73) Assignee: OAKLEY, INC., Foorhill Ranch, CA (US)

( * ) Notice: Subject to any disclaimer, the term of this patent is extended or adjusted under 35 U.S.C. 154(b) by 171 days.

(21) Appl. No.: 14/014,209

(22) Filed: Aug. 29, 2013

(65) Prior Publication Data

US 2014/0063437 A1 Mar. 6, 2014

Related U.S. Application Data

(60) Provisional application No. 61/696,008, filed on Aug. 31, 2012.

(51) Int. Cl.
*G02C 11/08* (2006.01)
*A61F 9/02* (2006.01)

(52) U.S. Cl.
CPC .................. *A61F 9/028* (2013.01); *A61F 9/025* (2013.01); *G02C 11/08* (2013.01); *A61F 9/026* (2013.01)

(58) Field of Classification Search
CPC .................................. A61F 9/028; G02C 11/08
USPC .......... 351/62, 41, 158; 2/436, 437, 435, 440, 2/448; D16/309, 326
See application file for complete search history.

(56) References Cited

U.S. PATENT DOCUMENTS

| 1,206,457 | A | 11/1916 | Mills |
| 4,674,851 | A | 6/1987 | Jannard |
| 4,730,915 | A | 3/1988 | Jannard |
| 4,859,048 | A | 8/1989 | Jannard |
| 4,867,550 | A | 9/1989 | Jannard |
| 4,878,749 | A | 11/1989 | McGee |
| 5,007,727 | A | 4/1991 | Kahaney et al. |
| 5,170,502 | A | 12/1992 | Hegendorfer et al. |
| 5,191,364 | A | 3/1993 | Kopfer |
| 5,410,763 | A | 5/1995 | Bolle |

(Continued)

FOREIGN PATENT DOCUMENTS

| EP | 1810648 | 2/2011 |
| WO | WO 97/41815 | 11/1997 |

OTHER PUBLICATIONS

Invitation to Pay Additional Fees for PCT Patent Application No. PCT/US2013/057309, dated Dec. 17, 2013.

(Continued)

*Primary Examiner* — Hung Dang
(74) *Attorney, Agent, or Firm* — Knobbe, Martens, Olson & Bear, LLP

(57) ABSTRACT

Eyewear is disclosed that can have multiple ventilation states providing different amounts of ventilation through the eyewear. The eyewear can include a lens and a frame. In some embodiments, the lens can be movable with respect to the frame to provide the multiple ventilation states. In some embodiments, the eyewear can include a gasket that removably attaches to the frame. In some embodiments, the gasket can be movable with respect to the frame to provide the multiple ventilation states.

22 Claims, 49 Drawing Sheets

(56) References Cited

U.S. PATENT DOCUMENTS

| | | | |
|---|---|---|---|
| 5,412,438 A | 5/1995 | Bolle | |
| 5,428,407 A | 6/1995 | Sheffield | |
| 5,493,348 A | 2/1996 | Harald, Jr. et al. | |
| 5,608,470 A | 3/1997 | Sheffield | |
| 5,610,668 A | 3/1997 | Mage | |
| 5,638,145 A | 6/1997 | Jannard et al. | |
| 5,796,461 A | 8/1998 | Stepan | |
| 5,841,506 A | 11/1998 | Karasawa et al. | |
| 5,898,468 A | 4/1999 | Mage | |
| 5,929,963 A | 7/1999 | McNeal | |
| 6,062,688 A | 5/2000 | Vinas | |
| 6,206,519 B1 | 3/2001 | Lin | |
| 6,231,179 B1 | 5/2001 | Lee | |
| 6,233,342 B1 | 5/2001 | Fernandez | |
| 6,244,705 B1 | 6/2001 | Ledbetter et al. | |
| 6,260,964 B1 | 7/2001 | Kroman | |
| 6,282,727 B1 | 9/2001 | Lindahl | |
| 6,290,354 B1 | 9/2001 | Safran | |
| 6,375,321 B1 | 4/2002 | Lee et al. | |
| 6,386,703 B1 | 5/2002 | Huang | |
| 6,474,812 B1 | 11/2002 | Moon | |
| 6,502,937 B2 | 1/2003 | Yang | |
| 6,550,914 B1 | 4/2003 | Kopfer | |
| 6,641,263 B2 | 11/2003 | Olney | |
| 6,702,439 B1 | 3/2004 | Lee | |
| 6,718,561 B2 | 4/2004 | Dondero | |
| 6,749,299 B1 | 6/2004 | Hsu | |
| 6,783,235 B1 * | 8/2004 | Lin | 351/62 |
| 6,793,336 B2 | 9/2004 | Min | |
| 6,817,709 B2 | 11/2004 | Min | |
| 6,863,394 B1 | 3/2005 | Nelson et al. | |
| 6,926,403 B2 | 8/2005 | Yi et al. | |
| 6,938,277 B2 | 9/2005 | Lindahl | |
| 6,969,170 B1 | 11/2005 | Smith | |
| 6,969,171 B2 * | 11/2005 | Lane et al. | 351/62 |
| 7,029,114 B2 | 4/2006 | Smith | |
| 7,036,927 B2 | 5/2006 | Kopfer | |
| 7,039,959 B2 | 5/2006 | Dondero | |
| 7,083,276 B2 | 8/2006 | Olney | |
| 7,091,634 B2 | 8/2006 | Yi et al. | |
| D537,097 S | 2/2007 | Freeman | |
| D537,860 S | 3/2007 | Freeman | |
| 7,192,134 B2 | 3/2007 | Teng | |
| 7,200,875 B2 | 4/2007 | Dondero | |
| 7,204,589 B2 | 4/2007 | Pieterman | |
| 7,237,891 B2 | 7/2007 | Min | |
| 7,244,022 B2 | 7/2007 | Lee | |
| 7,267,434 B2 | 9/2007 | Lane et al. | |
| 7,278,733 B2 | 10/2007 | Olney | |
| 7,364,287 B2 | 4/2008 | Lee et al. | |
| 7,370,961 B2 | 5/2008 | Lerner et al. | |
| 7,384,141 B2 | 6/2008 | Zelman | |
| 7,390,086 B2 | 6/2008 | Lee | |
| 7,396,124 B1 | 7/2008 | Wang | |
| 7,407,281 B2 | 8/2008 | Tagawa | |
| 7,431,453 B2 | 10/2008 | Hogan | |
| 7,434,929 B2 | 10/2008 | Jackson | |
| 7,441,889 B2 | 10/2008 | Zelman | |
| 7,452,068 B2 | 11/2008 | Collier et al. | |
| 7,520,604 B2 | 4/2009 | Choi | |
| 7,594,280 B2 | 9/2009 | Lindahl | |
| 8,028,350 B2 | 10/2011 | Hogen | |
| 8,235,523 B2 | 8/2012 | Yang | |
| 8,307,466 B2 | 11/2012 | Hsu | |
| 2004/0083540 A1 | 5/2004 | Dondero | |
| 2005/0105041 A1 | 5/2005 | Lerner et al. | |
| 2007/0024806 A1 | 2/2007 | Blanshay et al. | |
| 2007/0091253 A1 | 4/2007 | Chao | |
| 2007/0182916 A1 | 8/2007 | Blanshay et al. | |
| 2008/0094567 A1 | 4/2008 | Choi | |
| 2008/0266515 A1 | 10/2008 | Hou | |
| 2009/0066906 A1 | 3/2009 | Huang | |
| 2009/0079931 A1 | 3/2009 | Yang | |
| 2009/0122254 A1 | 5/2009 | Van Der Heijde et al. | |
| 2009/0151037 A1 | 6/2009 | Hsu | |
| 2014/0059747 A1 | 3/2014 | Belbey et al. | |
| 2014/0063438 A1 | 3/2014 | Cater et al. | |
| 2014/0078460 A1 | 3/2014 | Chang et al. | |

OTHER PUBLICATIONS

International Search Report and Written Opinon for PCT Patent Application No. PCT/US2013/057309, dated Feb. 24, 2014.

Oakley Wind Jacket, released at least as early as Aug. 30, 2011.

\* cited by examiner

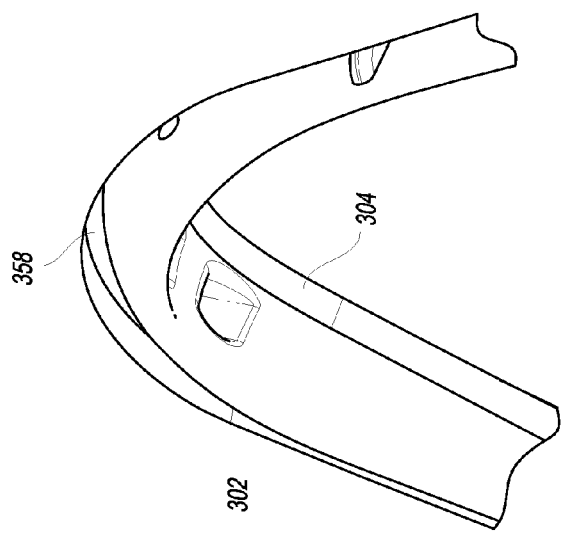
FIG. 36
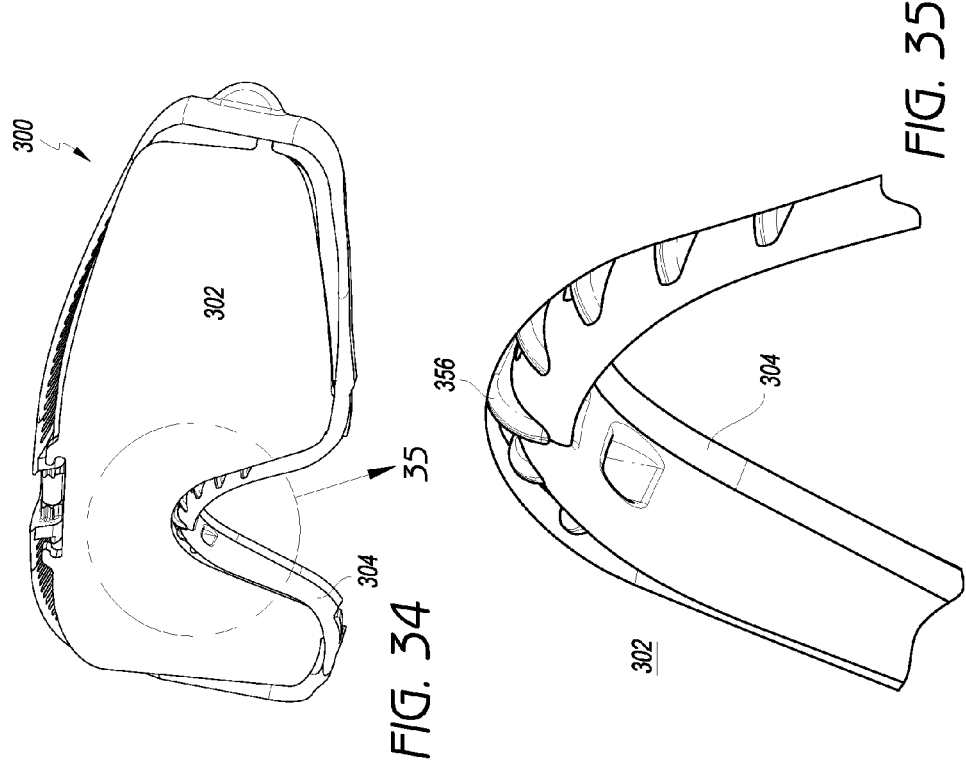
FIG. 35
FIG. 34

EYEWEAR HAVING MULTIPLE VENTILATION STATES

CROSS-REFERENCE TO RELATED APPLICATIONS

This application claims the benefit under 35 U.S.C. §119 (e) of U.S. Provisional Patent Application No. 61/696,008, filed Aug. 31, 2012, and titled "EYEWEAR HAVING MULTIPLE VENTILATION STATES," the entirety of which is hereby incorporated by reference and made a part of this specification for all that it discloses.

BACKGROUND

1. Field of the Disclosure

This disclosure relates to vented eyewear, and more specifically to eyewear having multiple ventilation states that produce different levels of ventilation.

2. Description of the Related Art

A wide variety of eyewear products are available. Some eyewear products suffer from various drawbacks, such as insufficient ventilation, insufficient protection (e.g., at lateral portions of the eyewear), insufficient ballistic impact resistance, etc. The embodiments disclosed herein address some of these drawbacks.

SUMMARY OF CERTAIN EMBODIMENTS

Various embodiments disclosed herein relate to eyewear that includes a lens and a frame that is configured to support the lens in a field of view of a wearer. The eyewear can include a gasket attached to the frame, and the gasket can include a flange configured to conform to the face of the wearer. The gasket can be movable relative to the frame between a closed position and an open position, and the open position provides more ventilation through the eyewear than the closed position.

In some embodiments, the lens does not move relative to the frame when the gasket is transitioned between the closed position and the open position.

The gasket can be movable relative to the frame to one or more intermediate positions that provide more ventilation than the closed position and less ventilation than the open position.

In some embodiments, the frame can include a pair of ear stems.

The gasket can be removably attached to the frame. The lens and frame can be configured to be wearable without the gasket (e.g., in a reduced protective configuration). In some embodiments, the gasket can be removably attachable to the lens (or lenses) of the eyewear. For example, the gasket can have a subframe that is configured to engage the lens (or lenses) of the eyewear.

The gasket can include a subframe configured to abut against the frame when the gasket is in the closed position. In some embodiments, the subframe can be configured to deform when the gasket is in the open position, and the deformation of the subframe can be configured to increase the ventilation through the eyewear as compared to an undeformed configuration of the subframe. In some embodiments, the subframe can be substantially rigid, and the subframe can be configured to pivot about a nose portion between the open position and the closed position.

Various embodiments disclosed herein relate to eyewear that includes a lens and a frame configured to support the lens in a field of view of a wearer. The eyewear can include a gasket that is removably attachable to the frame. In some embodiments, the gasket can be removably attachable to the lens (or lenses) of the eyewear. The gasket can include a flange configured to conform to the face of the wearer.

In various embodiments, the lens and frame can be configured to be wearable with the gasket in a protective configuration having a low level of ventilation, and the lens and frame can be configured to be wearable without the gasket in a reduced protective configuration having a high level of ventilation.

The gasket can include a gasket retention member configured to removably attach the gasket to the frame. The gasket retention member can include a grippable portion positioned at the top of the gasket. In some embodiments, the grippable portion and gasket retention member can provide a quick release that allows the gasket to be removed from the frame while the frame is being worn, without removal of the eyewear from the wearer's face. The gasket retention member can include a clip configured to engage a bridge portion of the frame. In some embodiments, the grippable portion can extend forward past the front end of the frame.

Various embodiments disclosed herein relate to eyewear that includes a lens having a front surface and a back surface and a frame configured to support the lens in a field of view of a wearer. The eyewear can include a gasket having a subframe that includes a front side and a back side. The gasket can include a flange on the back side of the subframe, and the flange can be configured to conform to the face of the wearer. The gasket can include a front seal on the front side of the subframe, and the front seal can be configured to abut against the back surface of the lens.

In some embodiments, the front seal can be attached to the flange. In some embodiments, the flange and the front seal can be integrally formed. The subframe can include one or more holes extending from the front side of the subframe to the back side of the subframe. A material can extend through the one or more holes to interconnect the flange to the front seal. In some embodiments, a material can extend around the outside of at least a portion of the subframe to interconnect the flange to the front seal.

In some embodiments, the gasket can be configured to allow ventilation through the eyewear. For example, the front seal can include one or more vent gaps that provide ventilation. In some embodiments, the flange can include one or more vent gaps that provide ventilation. In some embodiments, the subframe can include one or more vent gaps that provide ventilation. In some embodiments, the gasket can include a porous material that provides ventilation.

The gasket can include a gasket retention member configured to removably attach the gasket to the frame. The gasket retention member can include a grippable portion positioned at the top of the gasket, and the gasket can be configured to be removable from the frame while the frame is worn. In some embodiments, the lens and frame can be configured to be wearable without the gasket.

Various embodiments disclosed herein relate to eyewear that includes a lens and a frame configured to support the lens in a field of view of a wearer. The lens can be movable with respect to the frame between a closed position and an open position, and the open position can provide more ventilation through the eyewear than the closed position. The eyewear can include a lens retaining member configured to toggle the lens between the closed position and the open position, and the lens retaining member can be configured to retain the lens in the closed position in the event of a lens impact event.

The lens retaining member can include a front arm positioned forward of the lens when in the closed position and one or more positioning features that can be configured to engage one or more corresponding features on the frame to retain the lens in the closed position. The front arm can be coupled to the one or more positioning features at a junction that is rearward of the one or more corresponding features on the frame such that a force applied to the front arm by an impact on the lens is transferred to the one or more positioning features through the junction to prevent disengagement of the one or more positioning features from the one or more corresponding features on the frame. In some embodiments, the positioning features can be positioned on a front side of the lens retaining member, and the juncture can be on a back side of the lens retaining member.

Various embodiments disclosed herein relate to eyewear having a lens and a frame configured to support the lens in a field of view of a wearer. The lens can be movable with respect to the frame between a closed position and an open position, and the open position can provide more ventilation through the eyewear than the closed position. The frame can have a nose portion. The lens in the open position can be spaced apart from the nose portion of the frame such that a linear line can be drawn from a location outside the eyewear, between the nose portion and the lens, and to a location inside the eyewear that is rearward of the frame. The eyewear can include at least one ridge disposed between the nose portion of the frame and the lens such that the at least one ridge intersects the linear line. In some embodiments, all of one or more openings between the lens and the nose portion of the frame through which a linear line extends from a location outside the eyewear to a location inside the eyewear and rearward of the frame can have a width of about 1.5 mm or less.

Various embodiments disclosed herein relate to eyewear that includes a lens comprising one or more tabs and a frame configured to support the lens in a field of view of a wearer. The lens can be movable with respect to the frame between a closed position and an open position, and the open position can provide more ventilation through the eyewear than the closed position. The frame can include one or more grooves configured to receive the one or more tabs therein. The grooves and tabs can be configured to cause the lens to deform when in the open position, and the deformation of the lens can increase ventilation in the eyewear as compared to an undeformed configuration of the lens.

Various embodiments disclosed herein can relate to an eyewear attachment that can include a subframe and a flexible flange extending rearward from the subframe. The flexible flange can be configured to rest against and conform to the face of a wearer. The eyewear attachment can include a retention member configured to removably attach the eyewear attachment to eyewear. The retention member can include a grip for releasing the eyewear attachment from the eyewear, the grip positioned at a top of the eyewear attachment.

In some embodiments, the eyewear attachment can be used with eyewear that includes a lens and a frame configured to support the lens in a field of view of a wearer. The eyewear attachment can be removably coupled to the eyewear, and the lens and frame can be configured to be wearable without the eyewear attachment. The eyewear attachment can be removably coupled to a portion of the frame that is disposed proximate a top periphery of the lens. In some embodiments, the eyewear attachment is removably coupled to an engagement portion of the frame, and the grip can extend forward past the engagement portion of the frame.

In some embodiments, the retention member can include a clip configured to engage a bridge portion of the eyewear. The grip can extend forward past the clip. The eyewear attachment can be configured to be removable from the eyewear while the eyewear is being worn. The eyewear attachment can include a nose piece engagement member that is configured to engage a nose piece on the eyewear.

Various embodiments disclosed herein can relate to an eyewear attachment that includes a subframe having a front side and a back side, a retention member configured to removably couple the subframe to eyewear, a flexible flange on the back side of the subframe, where the flexible flange is configured to rest against and conform to the face of the wearer, and a front element on the front side of the subframe. The front element can be configured to abut against a back surface of a lens of the eyewear.

The eyewear attachment can be used with eyewear that includes a lens and a frame. The frame can be configured to support the lens in a field of view of a wearer. The eyewear attachment can be removably coupled to the eyewear. The lens and frame can be configured to be wearable without the eyewear attachment. The eyewear attachment can be removably coupled to the frame.

The front element can be a front seal that includes a flexible material that is configured to seal against at least a portion of the back surface of the eyewear lens. The front element can be attached to the flexible flange. The flexible flange and the front element can be integrally formed of the same material. The subframe can include one or more holes extending from the front side of the subframe to the back side of the subframe, and a material can extend through the one or more holes to interconnect the flexible flange to the front element. A material can extend around the outside of at least a portion of the subframe to interconnect the flexible flange to the front element. In some embodiments, the eyewear attachment can be configured to allow ventilation through the eyewear. For example, at least one of the front element, the flexible flange, and the subframe can include a porous material and/or vent gaps that provide ventilation.

The retention member can include a grip positioned at the top of the eyewear attachment, and in some embodiments, the eyewear attachment can be configured to be removable from the eyewear while the eyewear is worn.

The flexible flange can include a right orbital and a left orbital. The right orbital can be configured to at least partially seal around the wearer's right eye, and the left orbital can be configured to at least partially seal around the wearer's left eye. The enclosed volume inside the right orbital can be separated from an enclosed volume inside the left orbital to impede exchange of air between the enclosed volumes inside the right and left orbitals.

Various embodiments disclosed herein can relate to a method of removing an eyewear attachment. The method can include wearing eyewear and an eyewear attachment. The eyewear can include a lens and a frame supporting the lens in a field of view of a wearer. The eyewear attachment can include a subframe, a flexible flange conforming to the face of the wearer, and a retention member removably coupling the subframe to the eyewear. The retention member can include a grip disposed at a top of the eyewear attachment. The method can include pulling generally upwardly on the grip to disengage the retention member from the eyewear and to remove the eyewear attachment from the eyewear while the frame and lens are being worn.

Various embodiments disclosed herein can relate to eyewear that includes a lens, a frame configured to support the lens in a field of view of a wearer, and a lens retaining member coupled to a brow portion of the frame. The lens retaining member can be rotatable between a closed position and an open position. The closed position of the lens retaining member can retain the lens on the frame in a closed configuration such that the lens is in the field of view of the wearer. The open position of the lens retaining member can retain the lens on the frame in an open configuration such that the lens is in the field of view of the wearer. The open configuration of the lens can provide more ventilation through the eyewear than the closed configuration of the lens.

The lens retaining member can include a back arm disposed rearward of the lens and configured to push the lens to the open configuration when the lens retaining member is moved to the open position. The lens retaining member can include a front arm disposed forward of the lens and configured to push the lens to the closed configuration when the lens retaining member is moved to the closed position. The lens retaining member can include one or more positioning features configured to engage one or more corresponding features on the frame to maintain the lens retaining member in the closed position.

The eyewear can be a goggle that includes a flexible flange configured to rest against and conform to the face of the wearer. In some embodiments, the lens can substantially seal against the frame when the lens is in the closed configuration. The lens can include one or more tabs, and the frame can include one or more grooves configured to receive the one or more tabs therein. The tabs can slide within the grooves when the lens moves between the closed configuration and the open configuration. The frame can include a first lateral side and a second lateral side, and the brow portion can extend between the first and second lateral sides. In some embodiments, the lens retaining member can be substantially centered on the brow portion of the frame.

Various embodiments disclosed herein can relate to eyewear that includes a lens and a frame configured to support the lens in a field of view of a wearer. The lens can be movable with respect to the frame between a closed position and an open position. The lens can be configured to be in the field of view of the wearer when in the open position and when in the closed position. The open position can provide more ventilation through the eyewear than the closed position. A lens retaining member can be configured to toggle the lens between the closed position and the open position. The lens retaining member can be rotatable between a first position associated with the closed position of the lens and a second position associated with the open position of the lens. The lens retaining member can be configured to impede the lens from moving from the closed position to the open position in response to a force pushing the lens toward the open position.

The lens retaining member can include a front arm positioned forward of the lens when the lens is in the closed position, and the lens can apply a force on the front arm when the lens is pushed toward the open position. The lens retaining member can include one or more positioning features on a first side of the lens retaining member, and the one or more positioning features can be configured to engage one or more corresponding features on the frame when the lens is in the closed position. The front arm can be coupled to the one or more positioning features at a junction on a second side of the lens retaining member such that the force applied to the front arm by the lens imparts a force on to the one or more positioning features in a direction that further secures the lens in the closed position.

In some embodiments, the second side of the lens retaining member can be substantially opposite the first side of the lens retaining member. The one or more positioning features can be on a front side of the lens retaining member, and the junction can be on a back side of the lens retaining member. The one or more positioning features can include hooks. The one or more corresponding features on the frame can include teeth.

In some embodiments, the lens retaining member can include one or more positioning features configured to engage one or more corresponding features on the frame when the lens is in the closed position. The lens retaining member can include a locking element that can be configured such that the force that pushes the lens toward the open position causes the locking element to press against the one or more positioning features to impede the one or more positioning features from disengaging from the one or more corresponding features on the frame so as to impede the lens from moving from the closed position to the open position.

The lens retaining member can include a front arm positioned forward of the lens when the lens is in the closed position, and the locking element can be disposed on a front side of the front arm.

In some embodiments, the lens retaining member can be movable between the first position associated with the closed position of the lens, the second position associated with the open position of the lens, and a releasing position configured to enable the lens to be removed from the frame.

Various embodiments disclosed herein can relate to eyewear that includes a lens and a frame that has a nose portion. The frame can be configured to support the lens in a field of view of a wearer. The lens can be movable with respect to the frame between a closed position and an open position, and the open position can provide more ventilation through the eyewear than the closed position. The lens in the open position can be spaced apart from the nose portion of the frame such that a linear line extends from a location outside the eyewear, between the nose portion and the lens, and to a location inside the eyewear that is rearward of the frame. At least one ridge can be disposed between the nose portion of the frame and the lens and the at least one ridge can intersect the linear line.

The at least one ridge can be configured such that, when the lens is in the open position, all of one or more openings between the lens and the nose portion of the frame through which a linear line extends from a location outside the eyewear to a location inside the eyewear and rearward of the frame have a width of about 1.5 mm or less. The nose portion can include one or more openings extending through the nose portion and configured to increase ventilation through the eyewear when the lens is in the open position. The nose portion can include a plurality of ridges and the one or more openings can be disposed between the plurality of ridges.

The brow portion of the frame can include a plurality of openings. The plurality of openings in the brow portion can be in communication with the inside of the eyewear to provide ventilation when the lens is in the open position, and in some embodiments, the plurality of openings in the brow portion are not in communication with the inside of the eyewear when the lens is in the closed position.

Various embodiments disclosed herein can relate to an eyewear attachment for coupling to eyewear. The eyewear attachment can include a subframe and a flexible flange extending rearward from the subframe. The flexible flange can be configured to rest against and conform to the face of a wearer. The eyewear attachment can include an engagement member extending forward from the subframe and a retention member configured to couple to a frame of the eyewear. The engagement member can engage the retention member such that the eyewear attachment is configured to be disposed between the face of the wearer and the eyewear frame. The engagement member can be engageable with the retention member at a first location for positioning the eyewear attachment in an open position and a second location for positioning the eyewear attachment in a closed position. The open position is configured to provide more ventilation through the eyewear than the closed position.

The eyewear attachment can be used with eyewear that includes a lens and a frame configured to support the lens in a field of view of a wearer. The eyewear attachment can be coupled to the frame. The retention member can be removably coupled to the frame, and the lens and the frame can be configured to be wearable without the eyewear attachment. In some embodiments, the lens does not move relative to the frame when the eyewear attachment is moved between the closed position and the open position.

In some embodiments, the subframe can be configured to deform when the eyewear attachment is in the open position, and the deformation of the subframe can be configured to increase the ventilation through the eyewear as compared to an undeformed configuration of the subframe. The subframe can be configured to abut against the frame when the eyewear attachment is in the closed position. The eyewear attachment can be configured to be movable relative to the frame to one or more intermediate positions that provide more ventilation than the closed position and less ventilation than the open position.

Various embodiments disclosed herein can relate to an eyewear attachment for use with eyewear. The eyewear attachment can include a flexible flange configured to rest against and conform to the face of a wearer and an engagement member coupled to the flexible flange and configured to couple the eyewear attachment to an eyewear frame in a closed position and in an open position. The flexible flange can be configured to move relative to the frame between the closed position and the open position, and the open position can be configured to provide more ventilation through the eyewear than the closed position.

The eyewear attachment can be used with eyewear that includes a lens and a frame configured to support the lens in a field of view of a wearer. The eyewear attachment can be coupled to the frame. In some embodiments, the lens does not move relative to the frame when the eyewear attachment is moved between the closed position and the open position. The frame can include a pair of ear stems and a brow portion extending between the pair of ear stems. The engagement member can couple the eyewear attachment to the brow portion of the frame. The engagement member can be substantially centered on the brow portion of the frame.

The eyewear attachment can be removably coupled to the frame. The lens and the frame can be configured to be wearable without the eyewear attachment. The eyewear can be configured to substantially seal against the wearer's face when the eyewear attachment is in the closed position. The eyewear attachment can be configured to be movable relative to the eyewear frame to one or more intermediate positions that provide more ventilation than the closed position and less ventilation than the open position.

The eyewear attachment can include a subframe. The subframe can be configured to abut against the eyewear frame when the eyewear attachment is in the closed position. The subframe can be configured to deform when the eyewear attachment is in the open position, and the deformation of the subframe can be configured to increase the ventilation through the eyewear as compared to an undeformed configuration of the subframe. The eyewear attachment can be configured to remain attached to a nose portion of the eyewear frame when the eyewear attachment moves from the closed position to the open position.

The eyewear attachment can include a retention member that can be configured to couple to the frame. The flexible flange and engagement member can be movably coupled to the retention member. The engagement member can include one or more slots having one or more detents that separate the one or more slots into a first portion and a second portion. The retention member can include one or more prongs configured to engage the one or more slots. The prongs can be positioned in the first portion of the one or more slots when the flexible flange is in the closed position, and the prongs can be positioned in the second portion of the one or more slots when the flexible flange is in the first position. The retention member can be configured to removably couple to the eyewear frame. The retention member can be configured to couple to a brow portion of the eyewear frame, and the engagement member can be positioned on a brow portion of the eyewear attachment.

Various embodiments disclosed herein can relate to a method of ventilating eyewear. The method can include wearing eyewear and an eyewear attachment. The eyewear can include a lens and a frame supporting the lens in a field of view of a wearer. The eyewear attachment can include a retention member coupled to the frame, a subframe, a flexible flange conforming to the face of the wearer, and an engagement member with an arm extending forward from the subframe. The engagement member can engage the retention member to couple the eyewear attachment to the frame. The eyewear attachment can be in a closed position. The method can include pressing the arm rearward to move the eyewear attachment relative to the frame to an open position. The open position can provide more ventilation through the eyewear than the closed position.

In some embodiments, the lens does not move relative to the frame when the eyewear attachment is moved between the closed position and the open position. In some embodiments, the flexible flange remains in contact with the wearer's face as the eyewear attachment moves relative to the frame to the open position, and the frame moves away from the wearer's face as the eyewear attachment moves relative to the frame to the open position.

BRIEF DESCRIPTION OF THE DRAWINGS

The abovementioned and other features of the embodiments disclosed herein are described below with reference to the following drawings. The drawings are intended to illustrate example embodiments, and do not limit the inventions. The drawings contain the following Figures:

FIG. 34 shows a perspective view of the goggle.

FIG. 35 shows a detailed view of the nose portion of the goggle as shown in FIG. 34.

FIG. 36 shows a detailed view of the nose portion of the goggle with the ridges on the nose portion omitted from view.

DETAILED DESCRIPTION OF CERTAIN EMBODIMENTS

While the present description sets forth specific details of various embodiments, it will be appreciated that the description is illustrative only and should not be construed in any way as limiting. Additionally, although particular embodiments may be disclosed or shown in the context of unitary lens eyewear systems, dual lens eyewear systems can also be used. Further, although embodiments disclosed herein can be used with eyeglasses that have removable and replaceable lenses, embodiments are also contemplated in which the eyeglasses are not intended to provide for removable or replaceable lenses.

Figure 1:
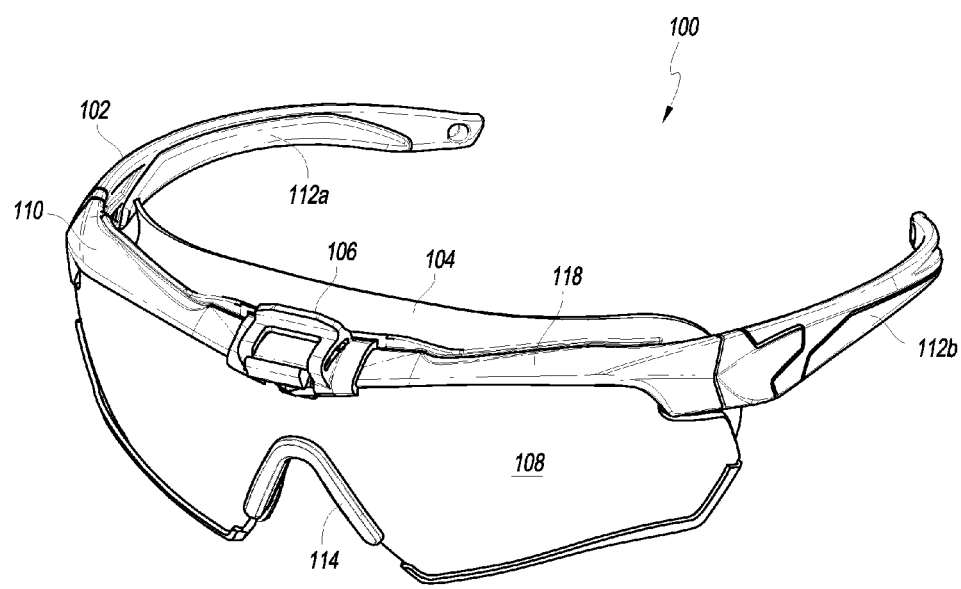
FIG. 1 is an isometric view of an example embodiment of eyewear.
Figure 2:
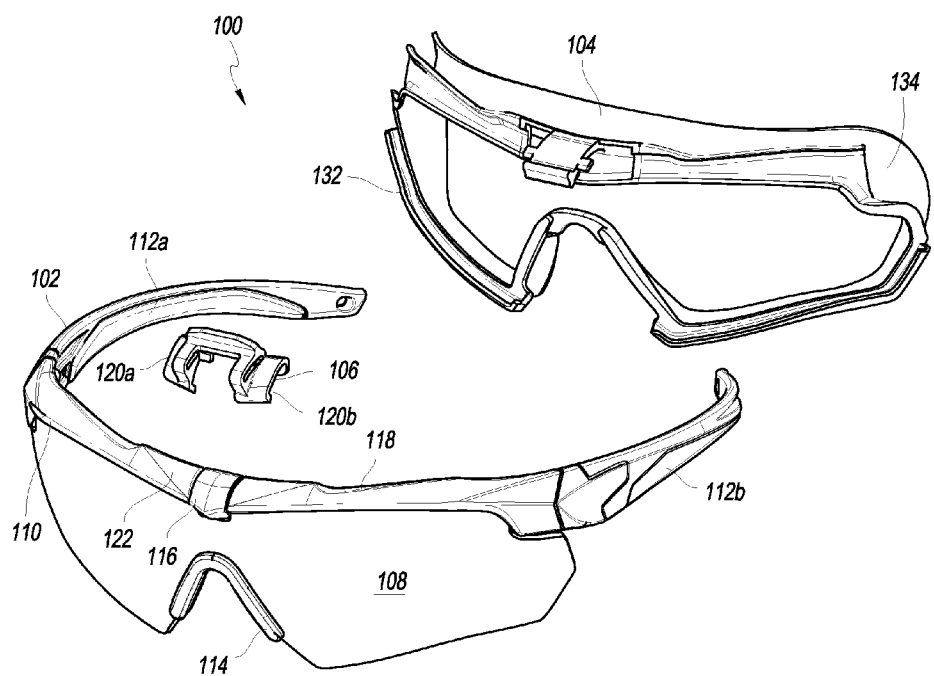
FIG. 2 is an exploded isometric view of the eyewear of FIG. 2.

FIG. 1 shows an isometric view of an example embodiment of eyewear 100. FIG. 2 is an exploded isometric view of the eyewear 100. Various features of the eyewear 100 can be similar to, or the same as, the other eyewear embodiments disclosed herein. The eyewear 100 can include an eyeglass 102, a gasket 104 (also referred to herein as an eyewear attachment), and a gasket retention member 106. The gasket 104 can be removably attached to the eyeglass 102 to convert the eyeglass 102 into eyewear 100 with protection from dust and debris, similar to a goggle. In some embodiments, the gasket retention member 106 can be part of the eyewear attachment, and the retention member 106 can be configured to removably couple the eyewear attachment to the eyeglass 102. The gasket 104 can be removed from the eyewear 100 to convert the eyewear 100 into an eyeglass 102 with reduced protection, for example when lateral protection from dust and debris is not needed. Thus, the user can wear the eyewear 100 in a protective configuration with the gasket 104 attached to the eyeglass 102, and the user can wear the eyewear 100 in a reduced protective configuration, as the eyeglass 102 without the gasket 104.

The eyeglass 102 can include a lens 108 and a frame 110 configured to position the lens 108 in a field of view of a wearer. The frame 110 can include a pair of ear stems 112a and 112b. The eyeglass 102 can also include a nose piece 114 configured to rest on the nose of a wearer. In some embodiments, the eyeglass 102 can include a lens retaining member 116 that can be configured to removably secure the lens 108 to the frame 110, thereby allowing the wearer to interchange the lens 108 of the eyeglass 102. For example, the lens 108 can be interchanged for a different lens if the lens 108 become damaged or dirty, and the lens 108 can be interchanged for a different lens having different optical properties depending on the conditions of use. The lens retaining member 116 can be configured to retain the lens 108 on the frame 110 in the event of impact to the lens 108 (e.g., a ballistic impact). Additional details relating to the eyeglass 102 are disclosed in U.S. Patent Publication No. 2011/0194065 (the "'065 Publication"), published on Aug. 11, 2011, and titled "EYEWEAR WITH ENHANCED BALLISTIC RESISTANCE," the entirety of which is incorporated by reference herein and made a part of this specification for all that it discloses.

Figure 3:
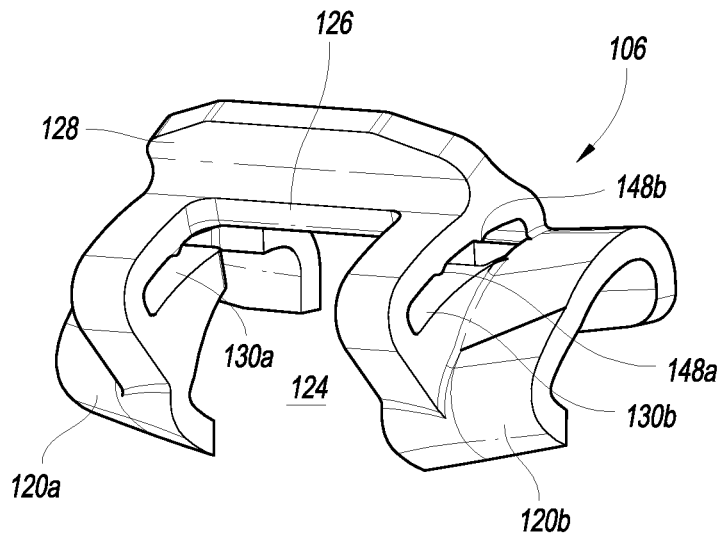
FIG. 3 is an isometric view of an example embodiment of a gasket retention member.
Figure 4:
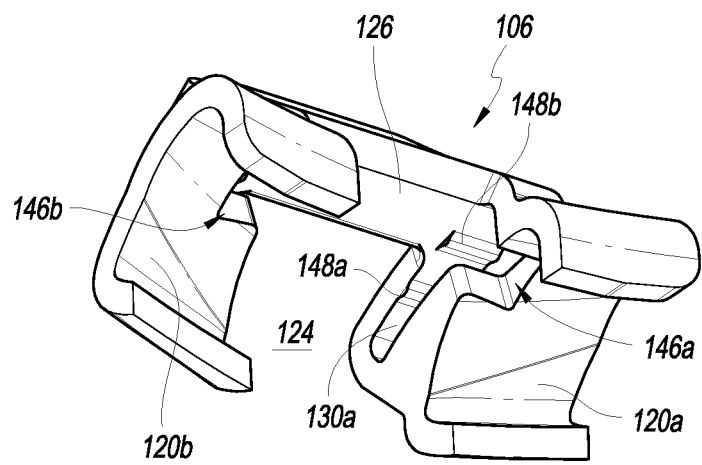
FIG. 4 shows the underside of the gasket retention member of FIG. 3.
Figure 5:
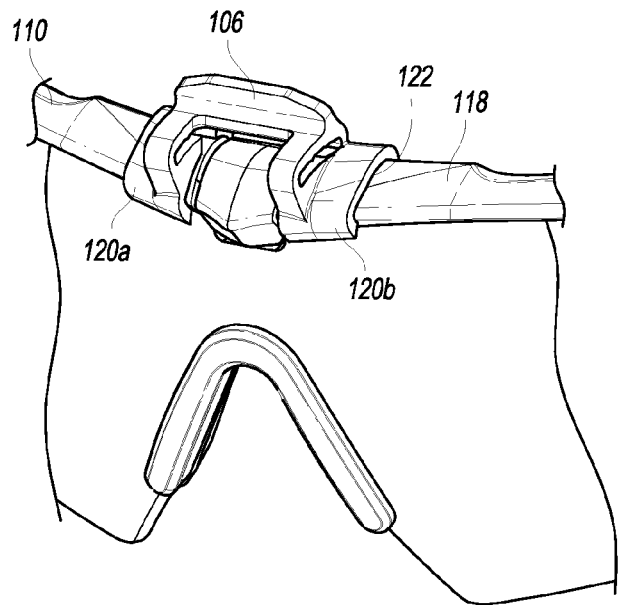
FIG. 5 shows an isometric view of the gasket retention member attached to the frame of the eyewear.

The gasket retention member 106 can be coupled to the frame 110, for example, to a brow portion 118 of the frame 110. In some embodiments, the gasket retention member 106 can be removably attachable to the frame 110. The gasket retention member 106 can include one or more engagement members that are configured to engage corresponding engagement members, or an engagement area, on the frame 110 to removably secure the gasket retention member 106 to the frame 110. The engagement members can cause engagement by a snap-fit, a friction-fit, a clip, etc. FIG. 3 is an isometric view of an example embodiment of a gasket retention member 106 that includes first and second clips 120a and 120b, although in some embodiments, a single clip can be used or other engagement members can be used. FIG. 4 shows the underside of the gasket retention member 106. The clips 120a and 120b can be generally C-shaped and can have curved arms that are shaped to correspond to an engagement area 122 on the brow portion 118 of the frame 110. FIG. 5 shows an isometric view of the gasket retention member 106 attached to the frame 110.

Figure 6:
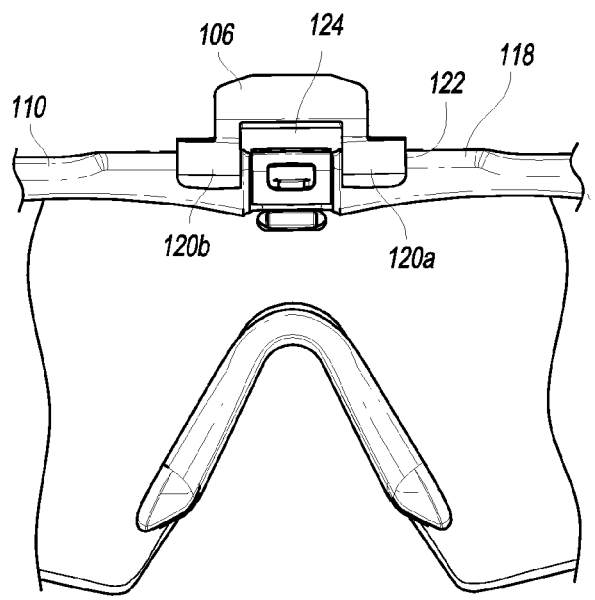
FIG. 6 is a back view of the gasket retention member attached to the frame of the eyewear.

With further reference to FIGS. 3 and 4, the clips 120a and 120b can be spaced apart forming a gap 124 therebetween. A bridge portion 126 can extend between the clips 120a and 120b, and the bridge portion 126 can be raised above the clips 120a and 120b so that the gap 124 is formed between the clips 120a and 120b and between the bridge portion 126 and the frame 110, as can be seen in FIG. 6. The gap can be configured to receive an engagement member of the gasket 104, as discussed herein. A tab 128 can extend upward from the bridge portion 126. The gasket retention member 106 can include a pair of advancing slots 130a and 130b positioned, for example, positioned above the clips 120a and 120b. In some embodiments, a single advancing slot can be used. The advancing slots 130a and 130b can be used to adjust the position of the gasket 106 relative to the frame 110, as discussed herein.

Figure 7:
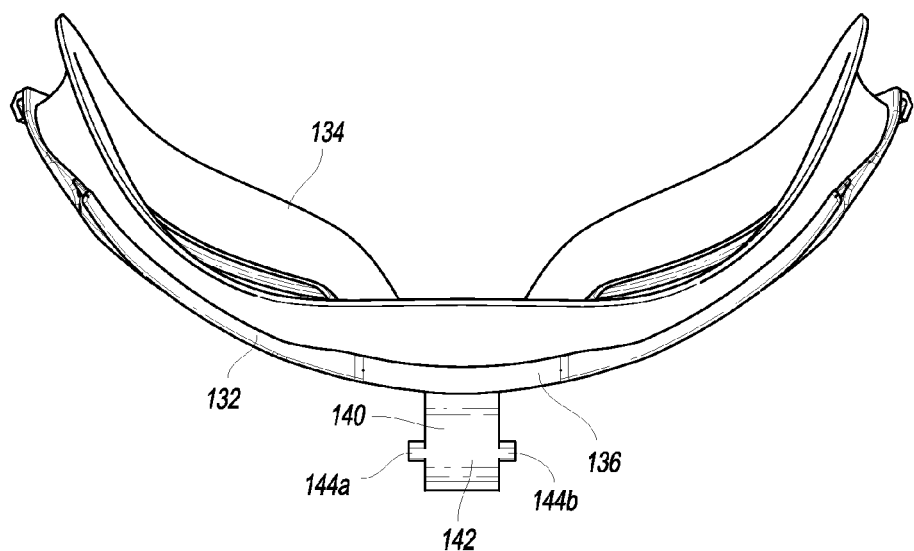
FIG. 7 shows a top view an example embodiment of a gasket.
Figure 8:
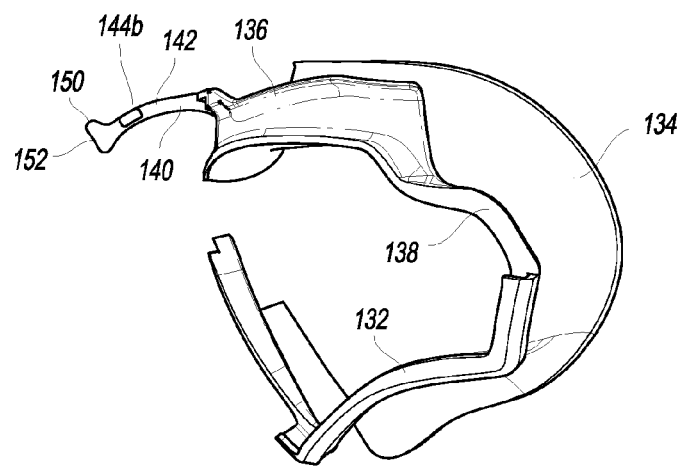
FIG. 8 shows a side view of the gasket of FIG. 7.
Figure 9:
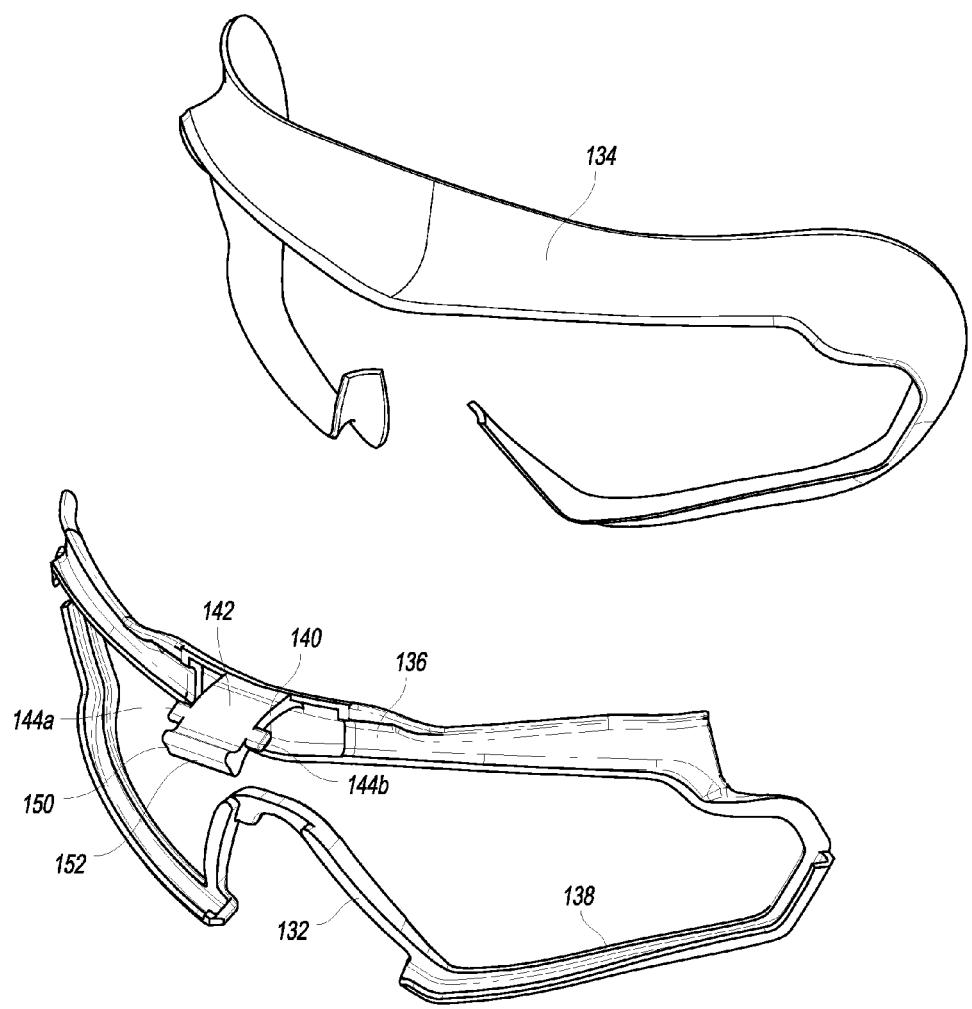
FIG. 9 shows an exploded isometric view of the gasket of FIG. 7
Figure 10:
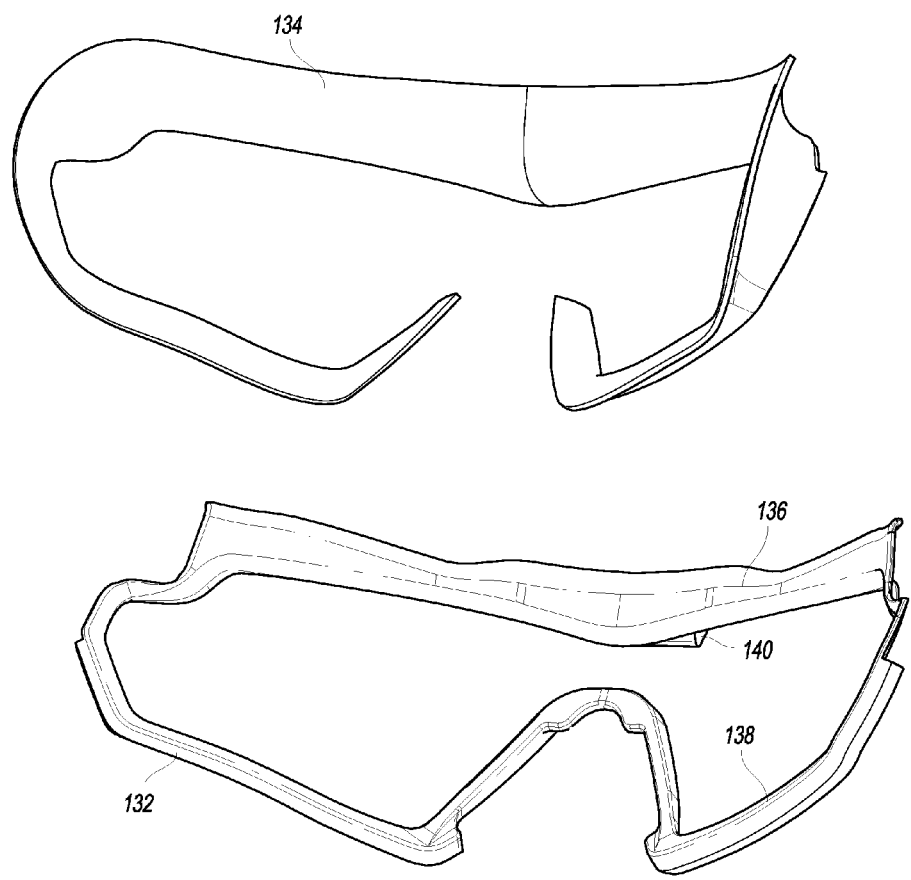
FIG. 10 shows another exploded isometric view of the gasket of FIG. 7.

FIG. 7 shows a top view of the gasket 104. FIG. 8 shows a side view of the gasket 104. FIG. 9 shows an exploded isometric view of the gasket 104, and FIG. 10 shows another exploded isometric view of the gasket 104. The gasket 104 can include a subframe 132 and a flange 134 (also referred to herein as a face flange). The face flange 134 can have contours that correspond to the face of the wearer so that when the face flange 134 is pressed against the face of the wearer, the face flange 134 can create a seal on at least a portion of the perimeter around the face flange 134, to substantially prevent dust and debris from passing between the face flange 134 and the wearer's face. The face flange 134 can include a flexible and resilient material that can conform to the contours of the wearer's face.

The face flange 134 can be attached to the subframe 132, for example, by an adhesive. The subframe can include a brow portion 136 that has a front surface that is contoured to correspond to the shape of the back surface of the brow portion 118 of the frame 110 of the eyeglass 102. Thus, when the gasket 104 is coupled to the eyeglass 102 in a closed configuration, the front surface of the brow portion 136 of the gasket subframe 132 can abut against the back surface of the brow portion 118 of the eyeglass frame 110, which can create a seal to substantially prevent dust and debris from passing between the gasket subframe 132 and the eyeglass frame 110 at the brow portions thereof. The subframe 132 can include a lens orbital 138 that is configured to have a shape that generally conforms to the perimeter of the lens 108. In some embodiments, when the gasket 104 is attached to the eyeglass 102 in a closed configuration, the lens 108 can abut against the lens orbital 138 along at least a portion of the perimeter of the lens 108, which can create a seal that substantially prevents dust and debris from passing between the lens 108 and the lens orbital 138. In some embodiments, the brow portion 136 and lens orbital 138 of the subframe 132 can be integrally formed of the same material, while in other embodiments, the brow portion 136 can be formed separately from the lens orbital 138, and can be attached thereto (e.g., by an adhesive). In some embodiments, the lens orbital 138 can be formed from a generally flexible and resilient material. The brow portion 136 can be formed of the same material as the lens orbital 138, or of a more rigid material.

The gasket 104 can include a gasket engagement member 140 that is configured to couple the gasket to the eyeglass 102. For example, the gasket engagement member 140 can be configured to engage the gasket retention member 106 to removably attach the gasket 104 to the eyeglass 102. The gasket engagement member 140 can include an arm 142 extending forward from the gasket subframe 132, such as from the brow portion 136 thereof. In some embodiments, the arm 142 can be integrally formed with some or all of the gasket subframe 132 (e.g., integrally formed with the brow portion 136 thereof). In other embodiments, the arm 142 can be separately formed from the subframe 132 and attached thereto. In some embodiments, the arm 142 can be formed of a rigid or semi-rigid material. The arm 142 can be configured to fit slidably into the gap 124 shown in FIG. 6.

The arm 142 can include a pair of prongs 144*a* and 144*b* extending out from the sides of the arm 142. The prongs 144*a* and 144*b* can be configured to engage the advancing slots 130*a* and 130*b* on the gasket retention member 106. As can be seen in FIG. 4, cutouts 146*a* and 146*b* can be formed at the back of the slots 130*a* and 130*b* to provide access for the prongs 144*a* and 144*b* to enter the slots 130*a* and 130*b*. When the gasket retention member 106 is attached to the frame 110, the frame can block the cutouts 146*a* and 146*b*, thereby preventing the prongs 144*a* and 144*b* from exiting the advancing slots 130*a* and 130*b* and retaining the gasket 104 attached to the eyeglass 102. Thus, to attach the gasket 104 to the eyeglass 102, the gasket retention member 106 and the gasket 104 can first be attached by inserting the prongs 144*a* and 144*b* through the cutouts 146*a* and 146*b* and into the advancing slots 130*a* and 130*b*. Then the gasket retention member 106 can be attached to (e.g., clipped onto) the frame 110, which can block off the cutouts 146*a* and 146*b* to retain the gasket 104 onto the eyeglass 102.

Figure 11:
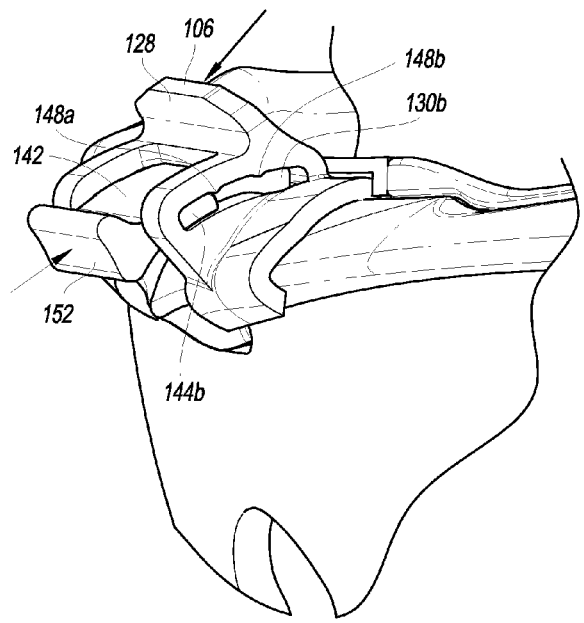
FIG. 11 shows the eyewear in a closed configuration.
Figure 12:
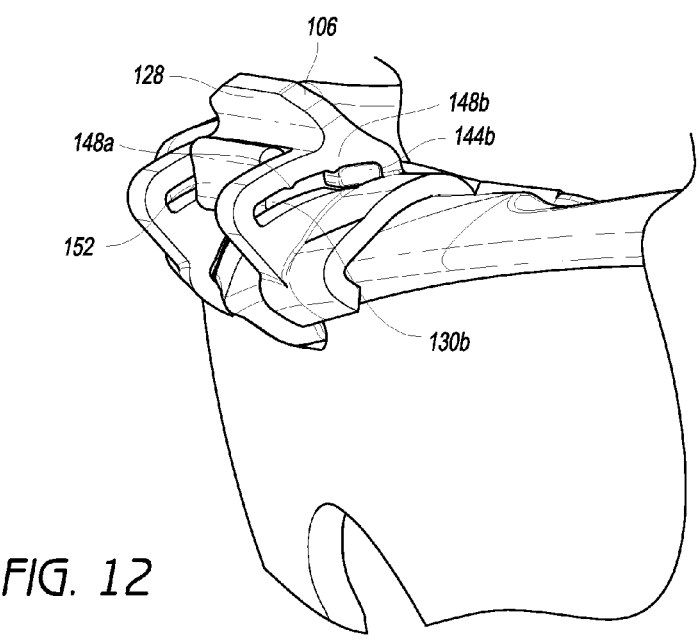
FIG. 12 shows the eyewear in an open configuration.

With reference now to FIGS. 11 and 12, in some embodiments, the eyewear 100 can have a plurality of ventilation states that produce different amounts of ventilation between the eyewear 100 and the wearer's face, and the eyewear 100 can be toggled between the plurality of ventilation states by the wearer. For example, the advancing slots 130*a* and 130*b* can have one or more detents 148*a* and 148*b* that separate the advancing slots 130*a* and 130*b* into a plurality of engagement positions. FIGS. 11 and 12 show advancing slots 130*a* and 130*b* having two detents 148*a* and 148*b*, thereby defining three engagement positions, but other configurations are also possible. A single detent in each advancing slot 130*a* and 130*b* can define only two engagement positions, or additional detents can be included to provide additional engagement positions (e.g., four, five, or more engagement positions).

FIG. 11 shows the gasket 104 in a closed position relative to the eyeglass 102. In the closed position, the prongs 144*a* and 144*b* can be advanced to the most forward position in the slots 130*a* and 130*b* (e.g., forward of the forward detent 148*a*), thereby bringing the gasket 104 forward to abut against the frame 110 and lens 108 as discussed herein. In the closed position, the eyewear 100 can provide a minimum amount of ventilation through the eyewear 100. For example, in some embodiments, the eyewear 100 can be substantially sealed when the gasket 104 is in the closed position, thereby substantially preventing dust and debris from entering the eyewear 100. The arm 142 can have an end portion 150, which in some cases can have a pushing surface 152 on the front surface thereof. The gasket 104 can be toggled to an open position by pushing the arm 142 rearward. For example, the tab 128 and pushing surface 152 can be configured to allow a user to use a thumb and finger to pinch the tab 128 and pushing surface 152 towards each other (as shown by arrows in FIG. 11). The tab 128 and pushing surface 152 can have prominent surfaces to allow the user to toggle the eyewear 100 to the open configuration while wearing gloves. In some embodiments, the eyewear 100 can be configured to allow the wearer to toggle the eyewear back to the closed configuration by pressing the eyewear against the wearer's face, which can also be performed reliably and comfortably while wearing gloves.

The arm 142 can be pushed back so that the prongs 144*a* and 144*b* are positioned rearward of the back detent 148*b* to transition the gasket 104 in an open position relative to the eyeglass 102, as shown in FIG. 12. In the open position, the gasket 104 can be spaced apart from the eyeglass 102 to allow air flow through the eyewear 100. The open configuration can provide a maximum amount of air flow through the eyewear 100. Although not shown in FIGS. 11 and 12, the gasket 104 can be positioned at an intermediate position by positioning the prongs 144*a* and 144*b* between the detents 148*a* and 148*b*. In some embodiments, an intermediate position can provide an intermediate amount of air flow that is greater than the closed position and less than the open position. In some embodiments, the eyewear 100 can be configured to have only two configurations: open and closed. In other embodiments, the eyewear 100 can have multiple intermediate configurations to provide various different amounts of air flow.

Figure 13:
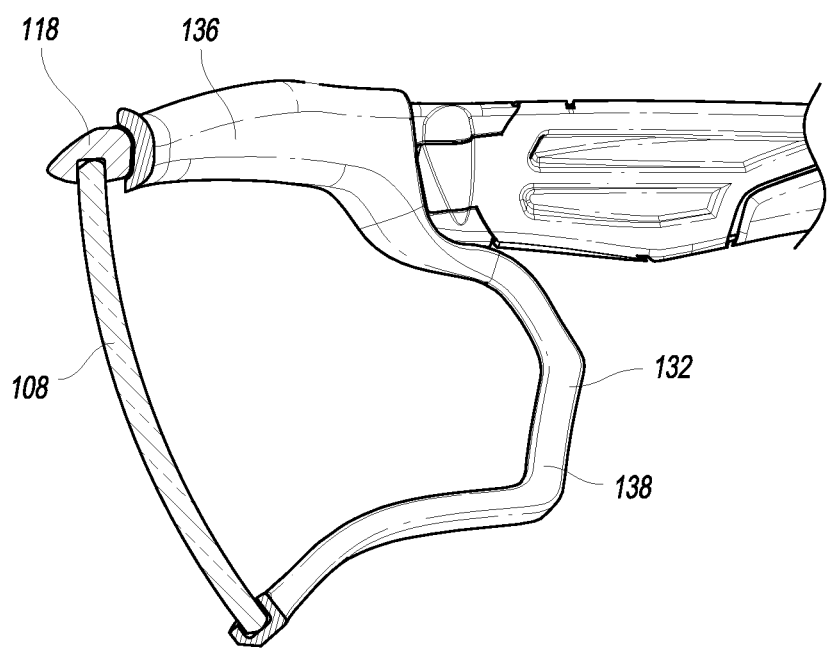
FIG. 13 shows a cross-sectional view of the eyewear in the closed configuration of FIG. 11.
Figure 14A:
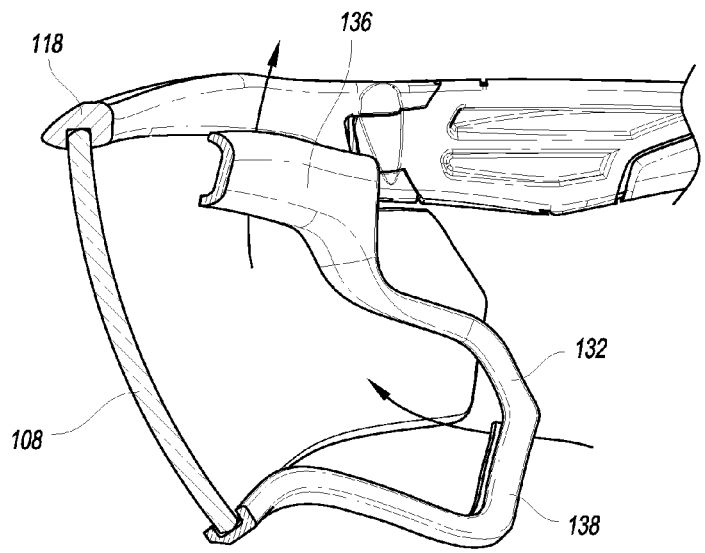
FIG. 14A shows a cross-sectional view of the eyewear in the open configuration of FIG. 12.

FIG. 13 shows a cross-sectional view of the eyewear 100 in the closed configuration of FIG. 11. The brow portion 136 of the gasket subframe 132 can abut against the brow portion 118 of the frame 110, and the lens 108 can abut against the lens orbital 138 of the subframe 132, thereby substantially sealing off air flow between the gasket 104 and the eyeglass 102. FIG. 14A shows a cross-sectional view of the eyewear 100 in the open configuration of FIG. 12. The brow portion 136 of the gasket subframe 132 can be displaced rearward from the brow portion 118 of the frame 110, thereby opening an air vent at the top of the eyewear 100, and the lens orbital 138 can be displaced away from the lens 108 at the outer portions of the eyewear 100, thereby opening air vents at the bottom and side portions of the eyewear 100. The open configuration can produce a chimney effect that allows hot, moist air to escape (e.g., through the top), which can be replenished by fresh air (e.g., received into the eyewear 100 from the sides and bottom). The air can flow across the inside surface of the lens 108, and the air can exit the eyewear 100 out the top, as shown by the arrows in FIG. 14A. The air flow through the eyewear 100 can remove moisture and rapidly defog the lens 108. The air flow through the eyewear 100 can prevent the lens 108 from fogging, or can improve the fogging resistance of the eyewear 100.

As can be seen in FIG. 14A, the subframe 132 can deform when eyewear 100 is transitioned from the closed configuration (as shown in FIG. 13) to the open configuration (as shown in FIG. 14A). The deformation of the subframe 132 can cause the air vent at the bottom of the eyewear 100 to open wider, than if the subframe 132 didn't deform. As can be seen, in FIGS. 8 and 11, for example, the arm 142 can be curved gradually, and the advancing slots 130*a* and 130*b* can have a gradual curvature that corresponds to the curvature of the arm 142. The curvature of the arm 142 and slots 130*a* and 130*b* can facilitate the deformation of the subframe 132 for widening the bottom air vents in the open configuration. Due to the curvature of the arm 142 and the slots 130*a* and 130*b*, as the arm is driven rearward to the open position, the brow portion 136 of the subframe 132 is driven downward as it opens (e.g., compare the brow portion 136 position in FIG. 13 (closed configuration) to FIG. 14A (open configuration)). Driving the brow portion 136 downward can cause the lens orbital 138 to buckle at the sides and deform. In some embodiments, the nose piece 114 can couple the subframe to the lens at the nose or central, lower portion of the eyewear 100. Thus, the nose piece 114 can prevent the central, lower portion of the subframe 132 from displacing downward or rearward as the brow portion 136 is driven downward and rearward, thereby facilitating the deformation of the subframe 132 at the side portions thereof. In some embodiments, the subframe 132 does not substantially deform when transitioned between the open state and the closed state. The subframe 132 (e.g., a substantially rigid, non-deforming subframe 132) can articulate when moved between the open state and the closed state. For example, in some embodiments, subframe 132 can pivot about the nose portion or interface between the subframe 132 and the lower edge or portion of the lens 108 when moved between the open state and the closed state.

Figure 14B:
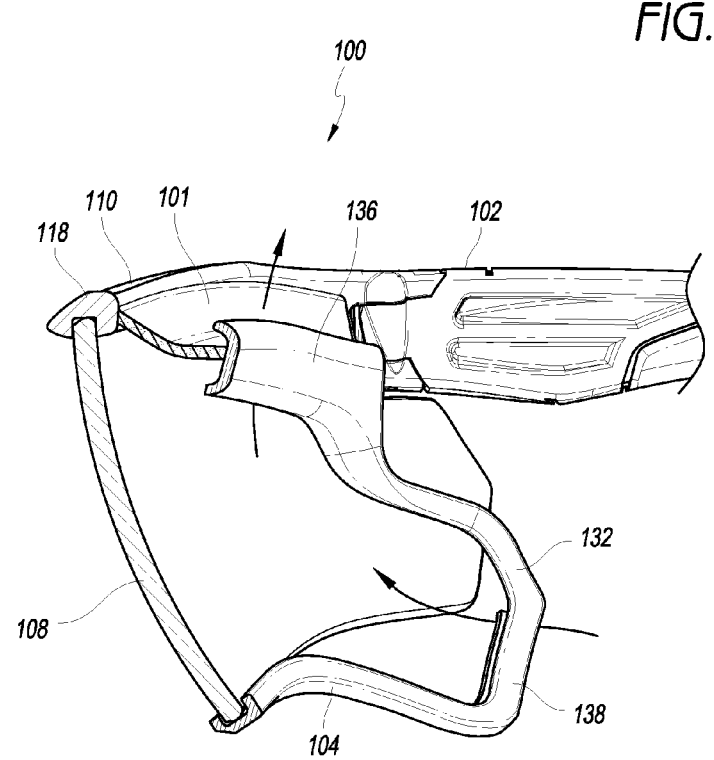
FIG. 14B shows a cross-sectional view of an example embodiment of eyewear configured to provide filtered ventilation.

In some embodiments, the eyewear 100 can provide for filtered ventilation. For example, in FIG. 14B, a filter 101 can be positioned between at least a portion of the gap between the eyeglass 102 and the gasket 104 when the gasket 104 is open. The filter 101 can be an air-permeable material, such as an open-cell foam. In some embodiments, the filter 101 can allow air to pass through while blocking dust and debris from entering the eyewear 100. The filter 101 can be coupled (e.g., adhered) to one or both of the eyeglass 102 and the gasket 104 to position the filter between the gasket 104 and the eyeglass 102. In some embodiments, the filter 101 can extend between the frame 110 of the eyeglass 102 and the subframe 132 of the gasket 104, although the filter 101 can also extend between other portions of the eyewear 100 (e.g., between the lens 108 and the subframe 132). Although FIG. 14B shows the filter 101 extending only along an upper opening, the filter 101 can extend across a majority or a substantial entirety of the opening between the eyeglass 102 and the gasket 104. In some embodiments, the filter 101 can be compressible, so that when the gasket 104 is advanced to the closed position, the filter 101 can be compressed between the eyeglass 102 and the gasket 104. In some embodiments, the filter 101 can be flexible (e.g., so that it can fold when the gasket 104 is advance to the closed position).

Figure 15A:
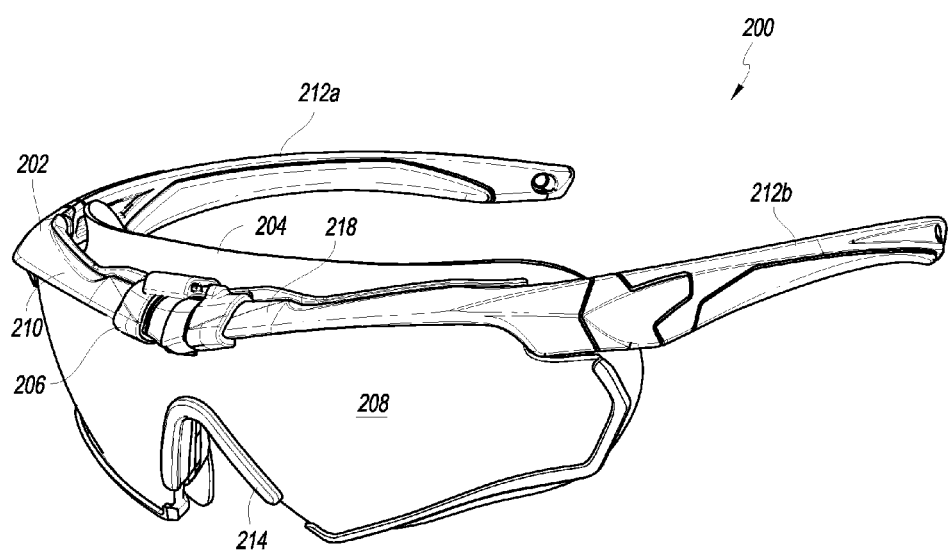
FIG. 15A shows an isometric view of an example embodiment of eyewear.
Figure 15B:
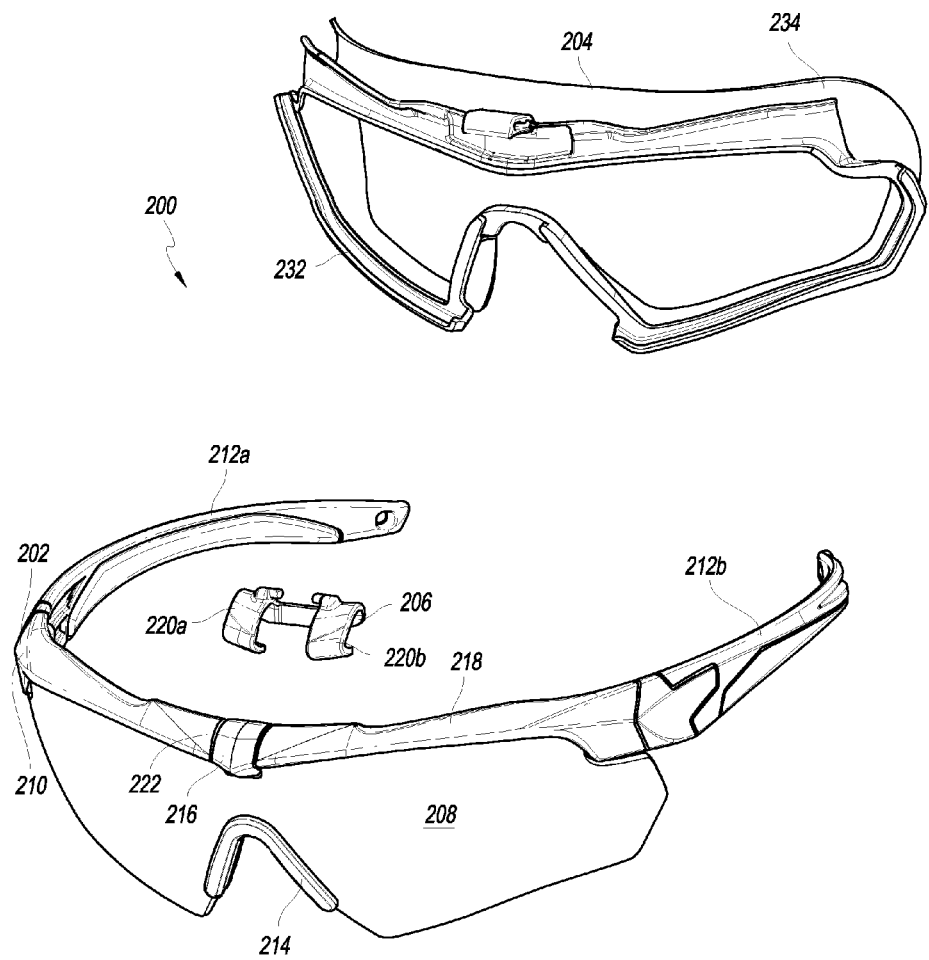
FIG. 15B shows an exploded isometric view of the eyewear of FIG. 15A.

Many modifications can be made to the eyewear 100. For example, the gasket can be attachable to the eyeglass in various suitable manners. FIG. 15A shows an isometric view of an example embodiment of eyewear 200, which can include features similar to, or the same as, the eyewear 100 or the other eyewear embodiments discussed herein. FIG. 15B shows an exploded isometric view of the eyewear 200. The eyewear 200 can include an eyeglass 202 and a gasket 204 (also referred to herein as an eyewear attachment). The eyeglass 202 can include a frame 210, which can include a pair of ear stems 212a and 212b, and the frame 210 can support at least one lens 208 in front of the wearer's eyes. The eyeglass 202 can also include a nose piece 214. A gasket retention member 206 can be attached to the brow portion 218 of the eyeglass frame 210 and can be configured to couple the gasket 204 to the eyeglass 202 (e.g., to the frame 210). The gasket 204 and/or the gasket retention member 206 can enable the gasket 204 to be removably attached to the eyeglass 202. Thus, the eyeglass 202 can be configured to be worn without the gasket 204 (e.g., in conditions in which dust and debris are not present), and the gasket 204 can be attached to the eyeglass 202 to provide a seal against at least a portion of the face of the wearer (e.g., in conditions in which dust or debris are present). As discussed herein, the gasket 204 and/or the gasket retention member 206 can be configured to allow the gasket 204 to toggle between a closed configuration and an open configuration.

Figure 15C:
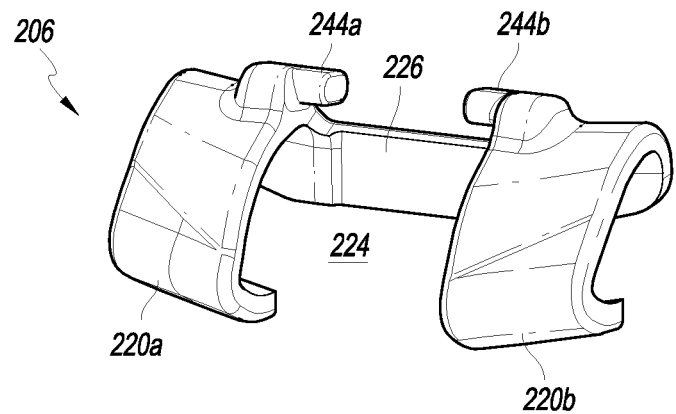
FIG. 15C is an isometric view of an example embodiment of a gasket retention member.
Figure 15D:
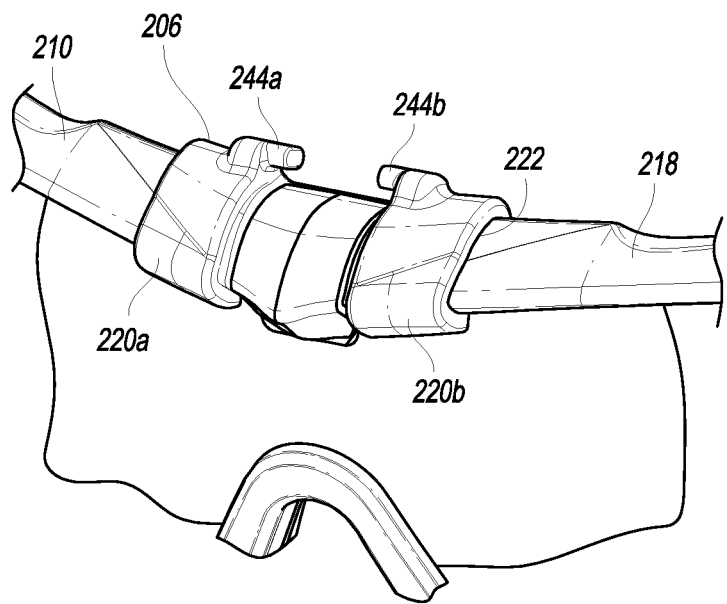
FIG. 15D shows the gasket retention member of FIG. 15C attached to the frame of the eyewear.

FIG. 15C shows an isometric view of the gasket retention member 206. FIG. 15D shows the gasket retention member 206 attached to an engagement area 222 on the brow portion 218 of the frame 210. The gasket retention member 206 can be configured to clip onto a brow portion 218 of an eyeglass frame 210, for example, using clips 220a and 220b, similar to the eyewear 100. The clips 220a and 220b can be spaced apart forming a gap 224 therebetween. A bridge portion 226 can extend between the clips 220a and 220b. The gasket retention member 206 can include one or more prongs 244a and 244b, which can extend inwardly into the gap 224.

Figure 15E:
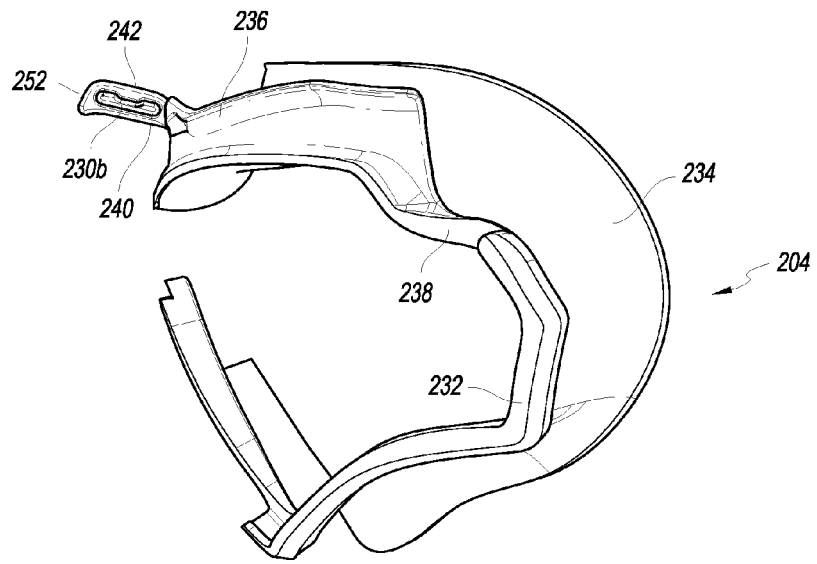
FIG. 15E shows a side view of an example embodiment of a gasket.
Figure 15F:
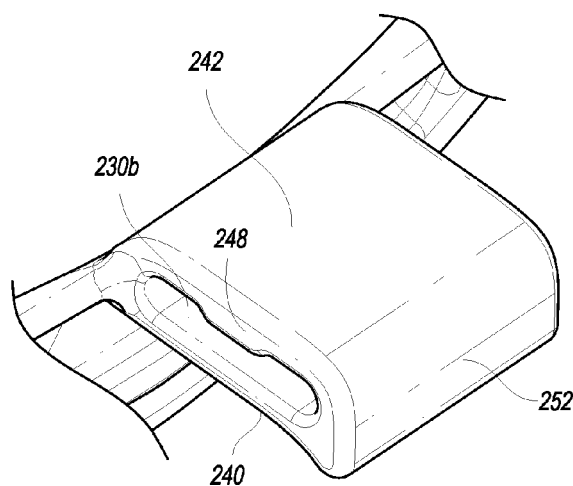
FIG. 15F shows an isometric view of a gasket attachment member on the gasket of FIG. 15E.
Figure 15G:
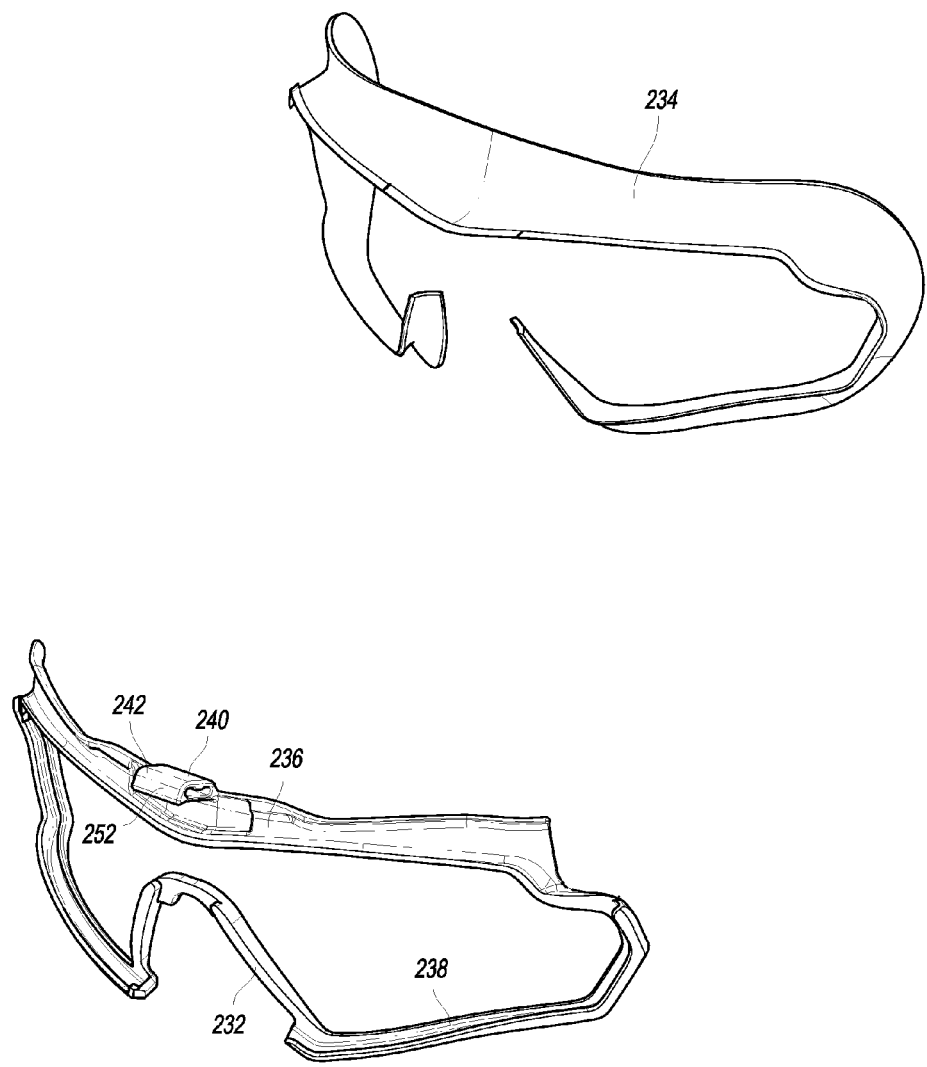
FIG. 15G shows an exploded isometric view of the gasket of FIG. 7.

FIG. 15E is a side view of the gasket 204. FIG. 15F is a detailed isometric view of the gasket engagement member 240 of the gasket 204. FIG. 15G is an exploded isometric view of the gasket 204. The gasket 204 can include a subframe 232 and a flange 234, similar to the gasket 104 discussed above. The subframe can include a brow portion 236 that has a front surface that is contoured to correspond to the shape of the back surface of the brow portion 218 of the frame 210 of the eyeglass 202. The subframe 232 can include a lens orbital 238 that is configured to have a shape that generally conforms to the perimeter of the lens 208.

The gasket engagement member 240 can be configured to couple the gasket 204 to the eyeglass 202. For example, the gasket engagement member 240 can be configured to engage the gasket retention member 206 to removably attach the gasket 204 to the eyeglass 202. The gasket engagement member 240 can include an arm 242 extending forward from the gasket subframe 232, such as from the brow portion 236 thereof. In some embodiments, the arm 242 can be integrally formed with some or the entire gasket subframe 232 (e.g., integrally formed with the brow portion 236 thereof). In other embodiments, the arm 242 can be separately formed from the subframe 232 and attached thereto. In some embodiments, the arm 242 can be formed of a rigid or semi-rigid material.

The arm 242 can include a pair of advancing slots 230a and 230b configured to engage the prongs 244a and 244b of the gasket retention member 206. The advancing slots 230a and 230b can include one or more detents 248 configured to separate the advancing slots 230a and 230b into two or more portions. For example, as shown in FIG. 15F, a single detent 248 can divide the advancing slot 230b into a front portion and a rear portion. A different number of detents (e.g., 2, 3, 4, or more detents) can be used than as shown in the Figures, and a different number of prongs and corresponding slots can be used than the two prongs 244a and 244b and two slots 230a and 230b shown in the Figures. For example, in some embodiments, a single slot can be used to engage a single prong.

Figure 15H:
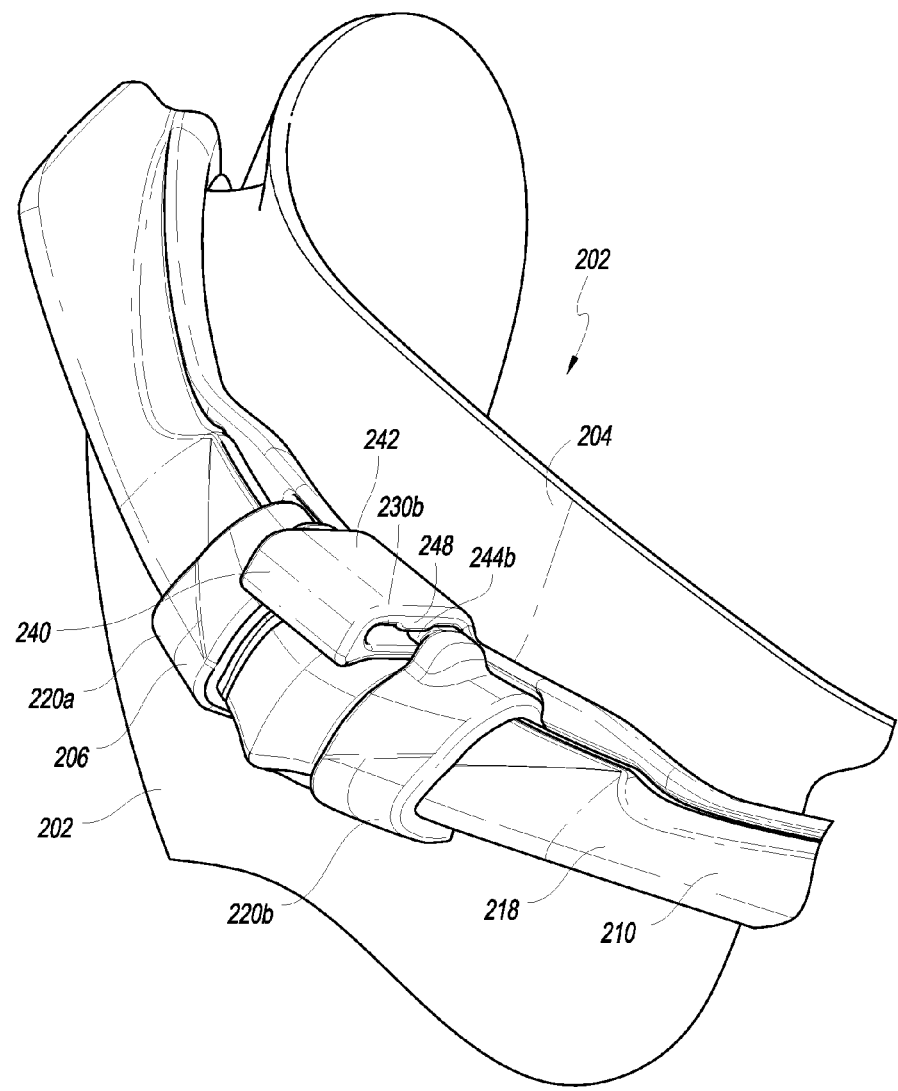
FIG. 15H shows the eyewear in a closed configuration.
Figure 15I:
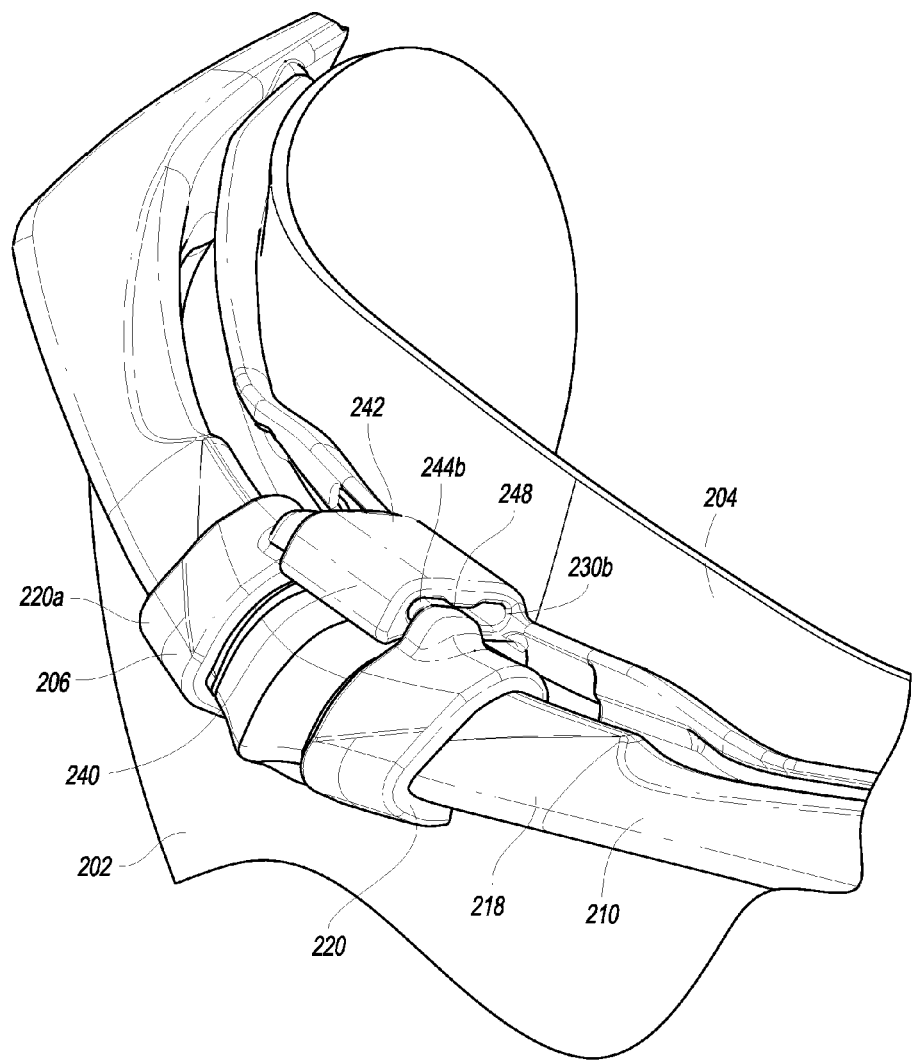
FIG. 15I shows the eyewear in an open configuration.

The at least one detent 248 can enable the gasket engagement member 240 to toggled between multiple configurations providing different amounts of air flow, as discussed herein. In some embodiments, a single detent 248 can be used to define two configurations: a closed configuration (as shown in FIG. 15H) and an open configuration (as shown in FIG. 15I). In the closed configuration, the gasket 204 can be advanced forward so that the prongs 244a and 244b are positioned rearward of the detents 248. A wearer can press the arm 242 rearward (e.g., by pressing on the pushing surface 252 of the arm 242) to toggle the eyewear 200 to the open configuration, separating at least a portion of the gasket 204 from the eyeglass 202 to increase air flow through the eyewear 200, as discussed herein. In the open configuration, the prongs 244a and 244b can be positioned forward of the detent 248. Many other variations are possible. For example, in some embodiments, the gasket retention member 206 can be integrally formed with the eyeglass frame 210.

In operation, the wearer can toggle the eyewear 200 to the open configuration by pressing the engagement member 240 (e.g., the arm 242) generally rearward (e.g., rearward and downward), which can cause the gasket 204 to move rearward relative to the frame 210. In some embodiments, the gasket 204 can abut against the face of the wearer, and pressing the arm 242 can cause the frame 210 to move forward away from the face of the wearer as the eyewear 200 changes to the open configuration. To toggle the eyewear 200 to the closed configuration, the user can press the eyeglass 202 (e.g., the frame 210 or the lens 208) rearward (e.g., posteriorly, towards the face of the wearer). The force on the eyeglass 202 can cause the engagement between the engagement member 240 and the retention member 206 to transition from an open position to a closed position. The gasket 204 can move forward (e.g., anteriorly) relative to the frame 210 to close the eyewear 200. In some embodiments, the gasket 204 can abut against the face of the wearer, and pressing the eyeglass 202 rearward can cause the frame 210 to move rearward to toggle the eyewear to the closed position. The user can open the eyewear 200 by pressing on a single location, as well as close the eyewear 200 by pressing on a single location, as opposed to pinching two objects together, pushing two locations simultaneously, holding one object or portion while moving a different object or portion, etc. Accordingly, the eyewear 200 can be opened and/or closed with a single hand, with a single hand wearing a glove, and/or with a single hand while holding an object, etc. The wearer does not need to grip anything to open and/or close the eyewear 200. This can be advantageous by allowing the wearer to open the eyewear 200 (e.g., to defog the eyewear) and/or close the eyewear 200 while the wearer's hands are engaged with other objects (e.g., during a combat situation).

Figure 16:
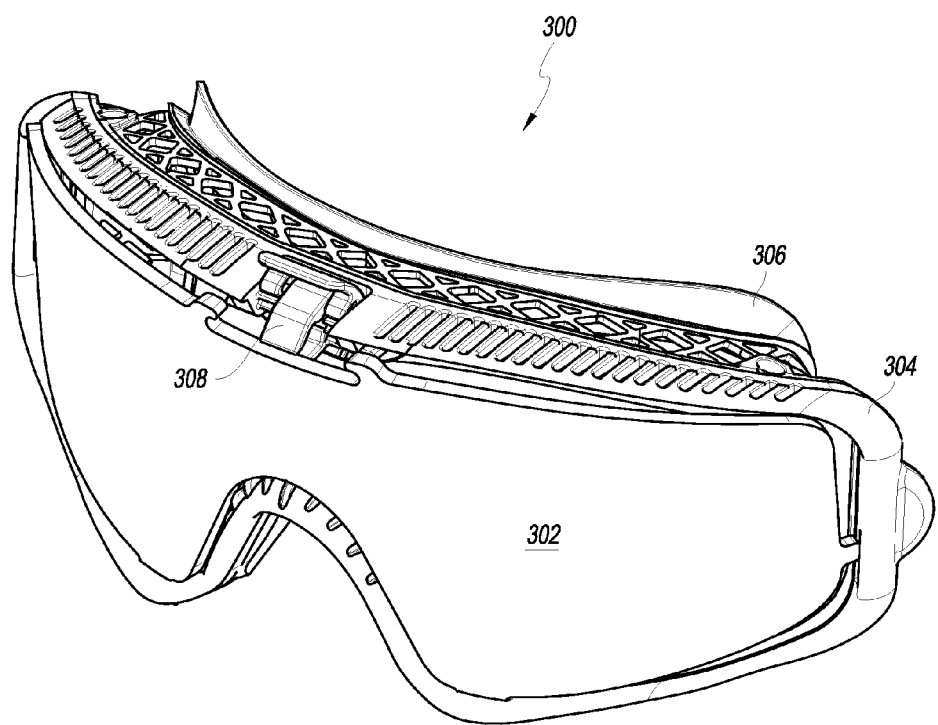
FIG. 16 is an isometric view of an example embodiment of eyewear, which can be a goggle.
Figure 17:
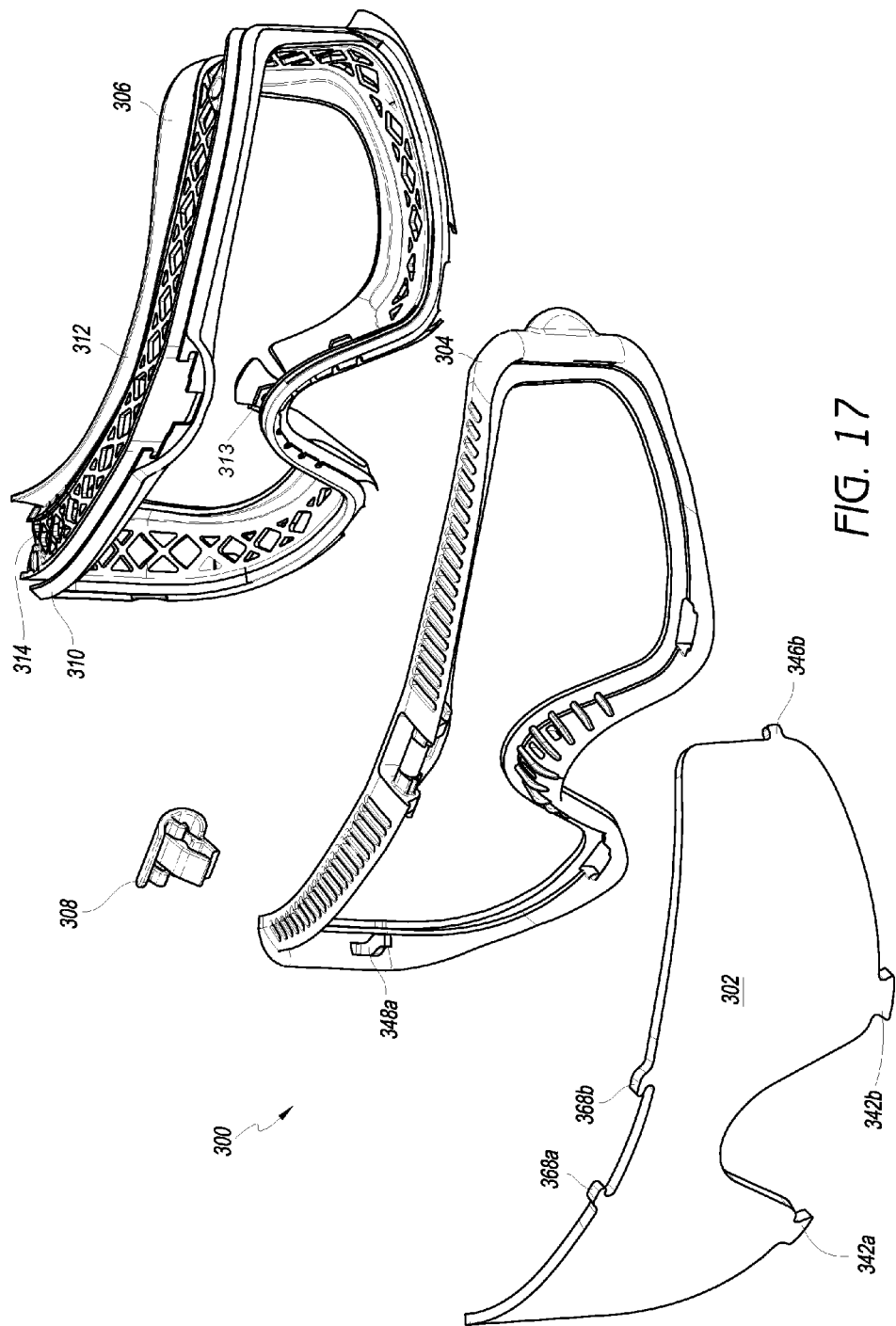
FIG. 17 is an exploded isometric view of the goggle of FIG. 16.
Figure 18:
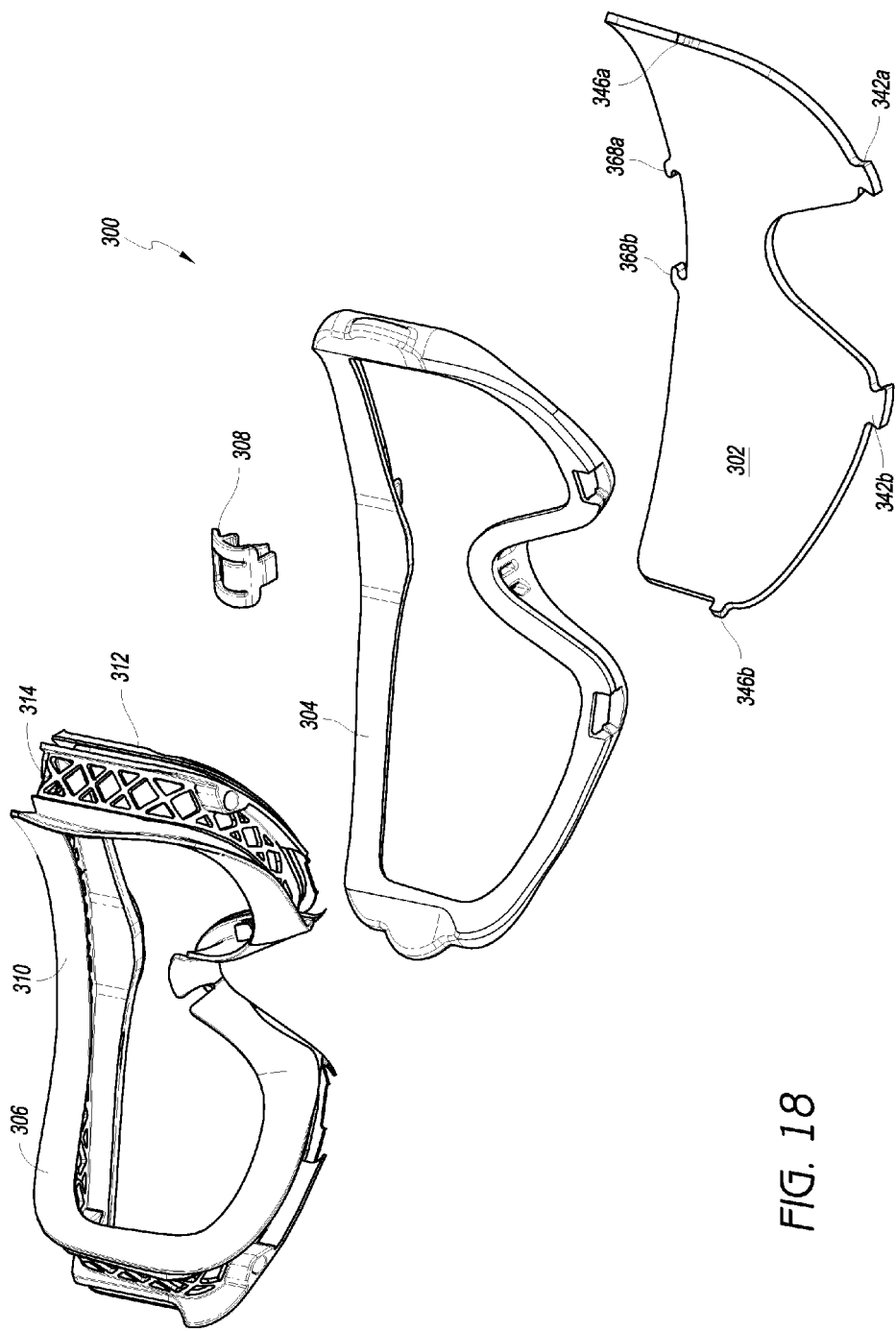
FIG. 18 is another exploded isometric view of the goggle.

FIG. 16 is an isometric view of an example embodiment of eyewear (e.g., a goggle 300) configured to have a plurality of ventilation states having different amounts of air flow through the goggle 300. FIG. 17 is an exploded isometric view of the goggle 300. FIG. 18 is another exploded isometric view of the goggle 300. The goggle 300 can include a lens 302, a frame 304, a flange 306 (also referred to herein as a face flange), and a lens retaining member 308 configured to toggle the goggle between the plurality of ventilation states. Various features of the eyewear 300 can be similar to, or the same as, the other eyewear embodiments disclosed herein.

The face flange 306 can have contours configured to fit to that face of a wearer, and the face flange can include a flexible, resilient material so that the face flange 306 can conform to the features of the wearer's face. In some embodiments, the face flange 306 can have a front portion 310 that is configured to attach to the frame 304, such as by an adhesive, a rear portion 312 that is configured to receive the face of the wearer, and an intermediate portion 314 extending between the front portion 310 and the rear portion 312. In some embodiments, the intermediate portion 314 can be vented and/or can include a porous material, such as foam, so that air exchange is permitted through the intermediate portion 314 of the face flange 306 even when the goggle 300 is in the closed configuration. However, in some embodiments, the air flow through the face flange 306 is insufficient to rapidly defog the lens 302 of the goggle 300. For example, the face flange 306 can be displaced rearward from the lens 302 such that air flow from the face flange 306 does not sufficiently clear air from the area adjacent to the lens 302. Accordingly, the goggle 300 can be configured to allow the lens 302 to be toggled between multiple positions to provide different amounts of air flow through the goggle 300 near the lens 302, as discussed herein. In some embodiments, the goggle 300 can be configured to be usable with a prescription eyewear attachment. For example, a prescription eyewear attachment (not shown) can include a prescription lens (or two prescription lenses) which can be mounted onto the goggle 300 in the wearer's field of view. For example the prescription eyewear attachment can include a subframe, which can include a first attachment portion. The goggle 300 can include a second, complementary prescription attachment portion 313 that is configured to engage the first attachment portion on the prescription eyewear attachment to couple the prescription eyewear attachment to the goggle 300. The first and second attachment portions on the prescription eyewear attachment and/or the goggle 300 can include various snap or interference fit features, clip mechanisms, or other attachment mechanisms as would be apparent to one of skill in the art based on the present disclosure.

Figure 19:
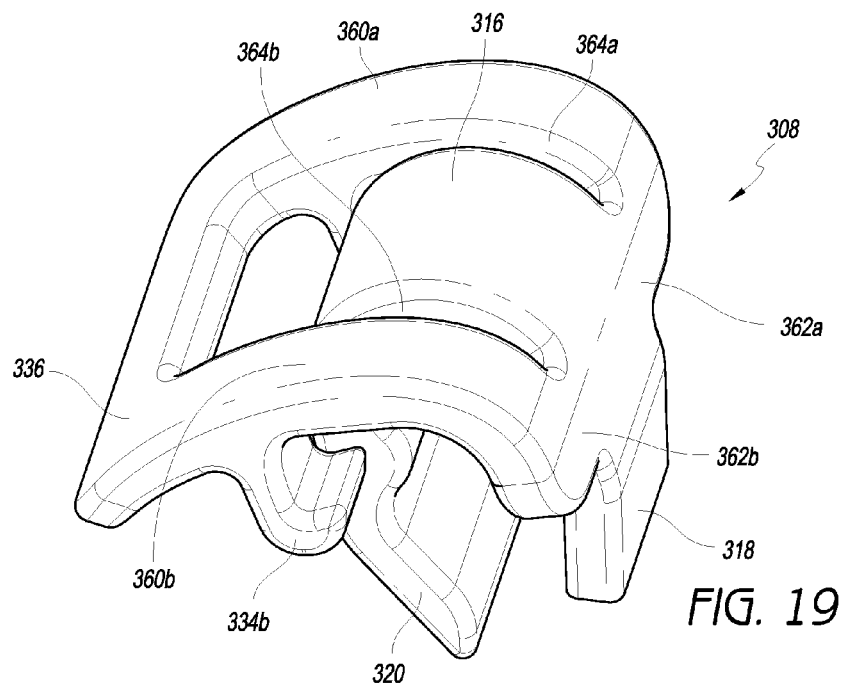
FIG. 19 is an isometric view of an example embodiment of a lens retaining member.
Figure 20:
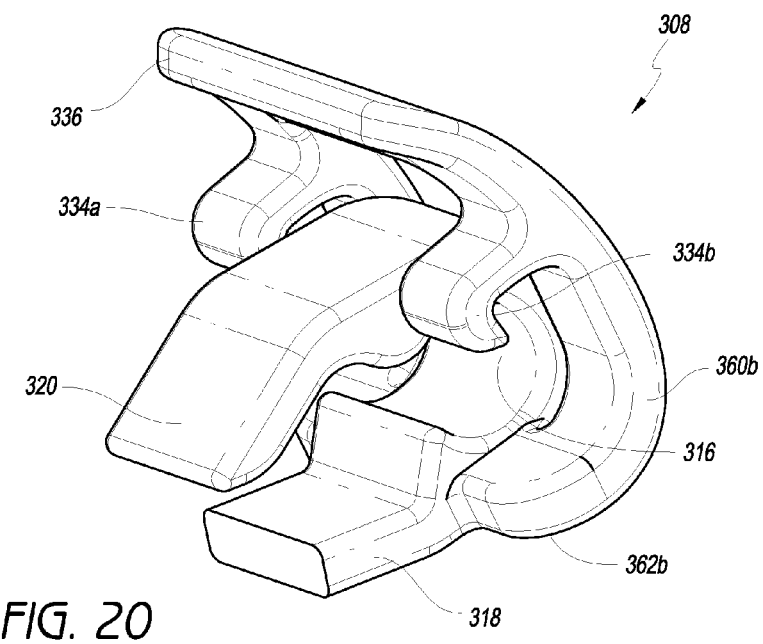
FIG. 20 is another view of the lens retaining member.

FIG. 19 is an isometric view of an example embodiment of a lens retaining member 308 that is configured to toggle the lens 302 between the plurality of positions to provide a plurality of ventilations states having different amounts of air flow through the goggle 300. FIG. 20 is another view of the lens retaining member 308. The lens retaining member 308 can be configured to movably attach to the frame 304 so as to be movable between different positions to move the lens 302 and set the ventilation state of the goggle 300. The lens retaining member 308 can include a clip 316 that is configured to clip onto the frame 304. The clip can include a first arm 318 extending down the back side of the clip 316, and a second arm 320 extending down the front side of the clip 316. The arms 318 and 320 can be configured to receive the lens 302 therebetween and to push the lens 302 to the different lens positions, as discussed herein. The clip 316 can be generally C-shaped. The lens retaining member 308 can have a tab 336 to allow the user to actuate the lens retaining member 308 to move the clip 316 for adjusting the position of the lens 302. As discussed elsewhere herein, the tab 336 can be coupled to the clip 316 on the back side of the clip 316, which can facilitate retention of the lens 302 in the closed position during a ballistic impact. Gaps 364a and 364b can be formed on either side of the clip 316 between the clip 316 and the extension arms 360a and 360b that extend from the tab 336 to the junction between the tab 336 and the clip 316.

Figure 21:
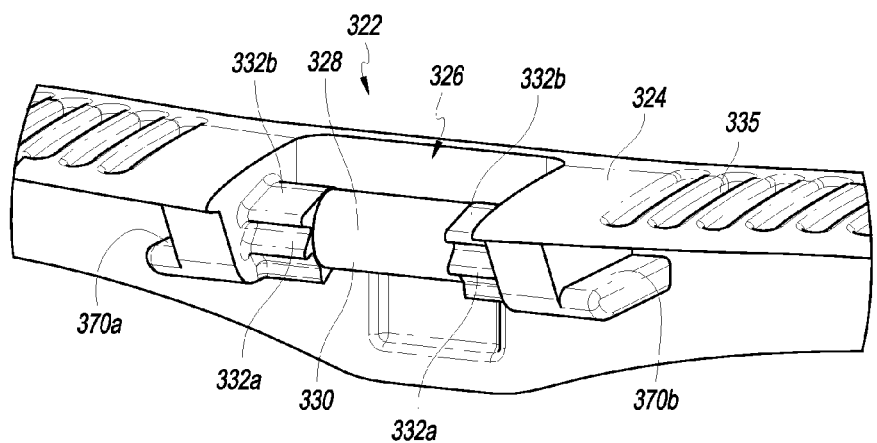
FIG. 21 shows an engagement portion of the frame of the goggle.
Figure 22:
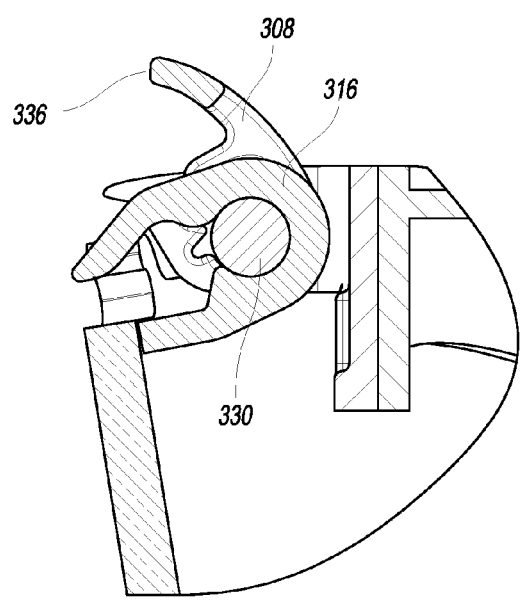
FIG. 22 is a cross-sectional view of the goggle.

FIG. 21 shows an engagement portion 322 of the frame 304, which can be positioned on a front of the brow portion 324 of the frame 304. The brow portion 324 of the frame 304 can extend forward forming an overhang over the top of the lens 302. A recess 326 can be formed in the brow portion 324 and an engagement bar 328 can extend across the recess 326. The clip 316 can be configured to clip onto the engagement bar 328. A gap can be formed behind the bar 328 so that the first arm 318 of the clip 316 can pass behind the engagement bar 328. A clipping portion 330 of the engagement bar 328 (e.g., at the central portion thereof) can have a substantially circular cross-sectional shape that corresponds to the shape of the inner surface of the clip 316 thereby allowing the clip 316 to rotate about the engagement bar 328, as can be seen in FIG. 22, which is a cross-sectional view taken through the clipping portion 330 of the bar 328.

The engagement portion 322 of the frame 304 can include positioning features, such as the teeth 332a and 332b, that are configured to define a plurality of positions for the lens retaining member 308. A pair of lower teeth 332a can be positioned on the sides or ends of the engagement bar 328, and a pair of upper teeth 332b can be positioned on the sides or ends of the engagement bar 328, as shown, although other configurations are possible. For example, a single set of teeth 332a and 332b can be used, or a different number of teeth (e.g., one tooth, or three, four, of five teeth) can be used depending on the desired number of lens positions. The lens retaining member 308 can include positioning features, such as the hooked arms 334a and 334b, that are configured to engage the positioning features on the frame 304, such as the teeth 332a and 332b.

Figure 23C:
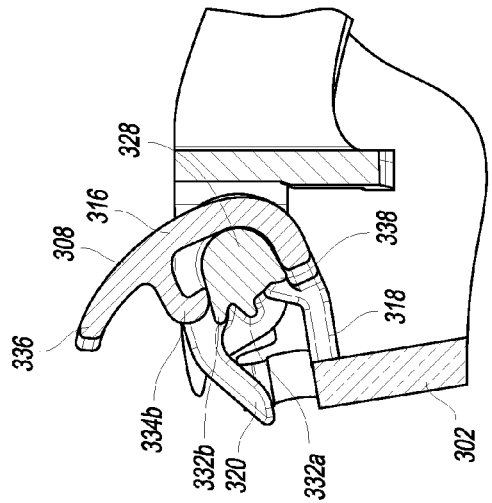
FIG. 23C is a cross-sectional view of the lens retaining member in a releasing position.
Figure 23B:
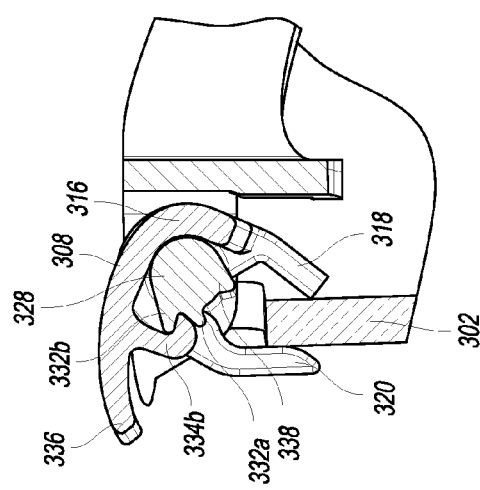
FIG. 23B is a cross-sectional view of the lens retaining member in an open position.
Figure 23A:
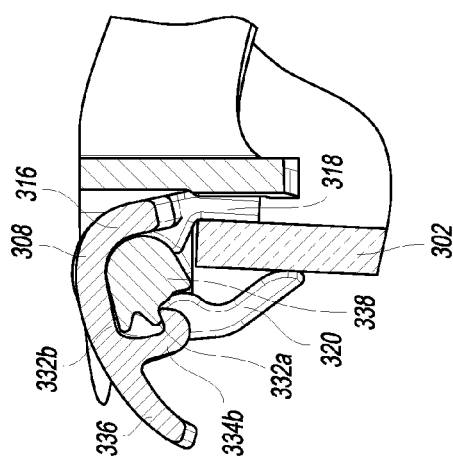
FIG. 23A is a cross-sectional view of the lens retaining member in a closed position.

FIG. 23A shows a cross-sectional view of the lens retaining member 308 in a closed position. FIG. 23B shows a cross-sectional view of the lens retaining member 308 in an open position. FIG. 23C shows a cross-sectional view of the lens retaining member 308 in a releasing position. In the closed position shown in FIG. 23A, the hooked arm 334a can be engaged below the lower tooth 332a thereby preventing the lens retaining member 308 from rotating towards the open position. The back arm 318 of the clip 315 can abut against the frame 304, which can prevent the lens retaining member from rotating further away from the open position. The front arm 320 can be positioned forward of the lens 302 to retain the lens 302 in the closed configuration.

To transition the goggle 300 to the open configuration (shown in FIG. 23B), the wearer can press upward on the tab 336 that is attached to the hooked arms 334a and 334b, thereby causing the hooked arms 334a and 334b to disengage from the lower teeth 332a to allow the lens retaining member 308 to rotate from the closed position to the open position. As shown in FIG. 23B, when in the open position, the hooked arm 334a can be engaged between the teeth 332a and 332b, to prevent the lens retaining member 308 from rotating towards the closed position or towards the releasing position. The lens 302 can be held in an open configuration between the arms 318 and 320. To transition the goggle 300 from the open configuration back to the closed configuration, the wearer can press the tab 336 downward to cause the hooked arm 334a snap over the lower tooth 332a. In some cases, the wearer can press on the lens 302 (e.g., in a rearward direction and/or towards the wearer's face) to toggle the goggle 300 to the closed configuration. In some cases, the user can press on the front arm 320 (e.g., in a rearward direction and/or towards the wearer's face) to toggle the goggle 300 to the closed configuration.

To transition the goggle 300 to the releasing configuration (shown in FIG. 23C), the wearer can press upward on the tab 336 to cause the hooked arms 334a and 334b to snap over the top tooth 332b so that the lens retaining member 308 rotates from the open position to the releasing position. The top tooth 332b can prevent the lens retaining member 308 from rotating back towards the open or closed positions. In some embodiments, the lens retaining member 308 can be prevented from rotating further in the releasing direction than shown in FIG. 23C. The back of the engagement bar 328 can have a generally circular curvature that allows the lens retaining member 308 to rotate between the closed, open, and releasing positions. The engagement bar 328 can include a protrusion 338 (e.g., on the bottom thereof) that can abut against the back of the lens retaining member 308 when the lens retaining member 308 is rotated to the releasing position (shown in FIG. 23C), thereby preventing the lens retaining member 308 from rotating further in the releasing direction. In some embodiments, the protrusion 338 can be an additional tooth positioned below the teeth 332a and 332b, although the additional tooth 338 is not configured to engage the hooked arms 334a and 334b as are the teeth 332a and 332b. When in the releasing position, the back arm 318 can push the lens 302 away from the frame 304, and in some cases can extend generally orthogonal to the back surface of the lens 302. When in the releasing position, the front arm 320 is not positioned in front of the lens 302, and can be positioned above the lens 302 as shown, so that the lens 302 can be removed. Thus, to release the lens, the user can toggle the lens retaining member 308 from the closed position to the open position, and then toggle the lens retaining member from the open position to the releasing position. With the lens retaining member 308 in the releasing position, the user can remove the lens 302 from the frame 304 (e.g., by lifting generally upwardly on the lens 302 and/or by pulling or pushing the lens 302 forward). The goggle 300 can be configured to position the lens 302 in the field of view of the wearer when the lens 302 is in the closed, open, and/or releasing positions.

Figure 24:
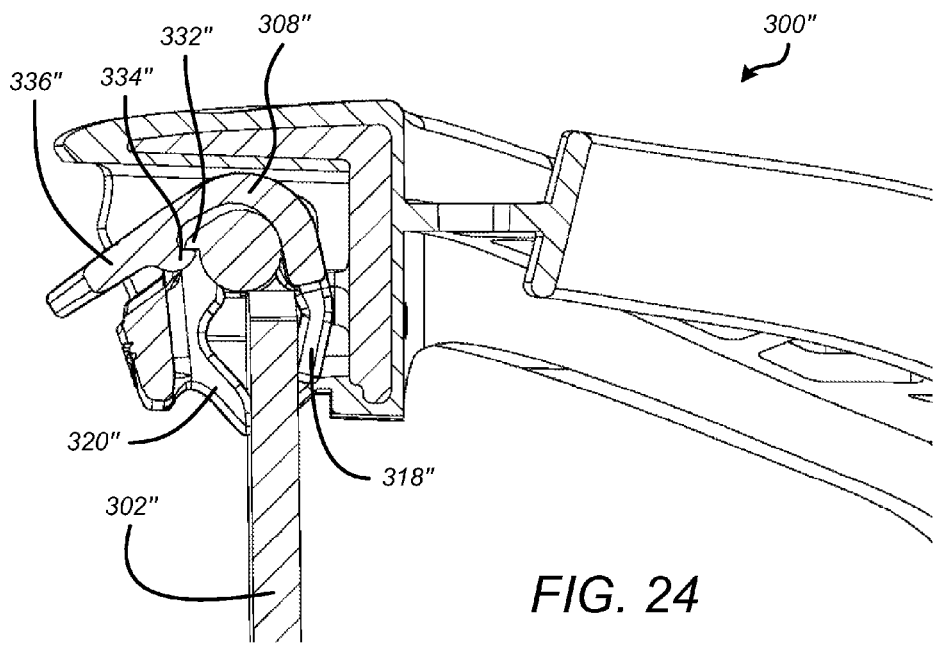
FIG. 24 is a cross-sectional view of another embodiment of a lens retaining member in a closed position.
Figure 25:
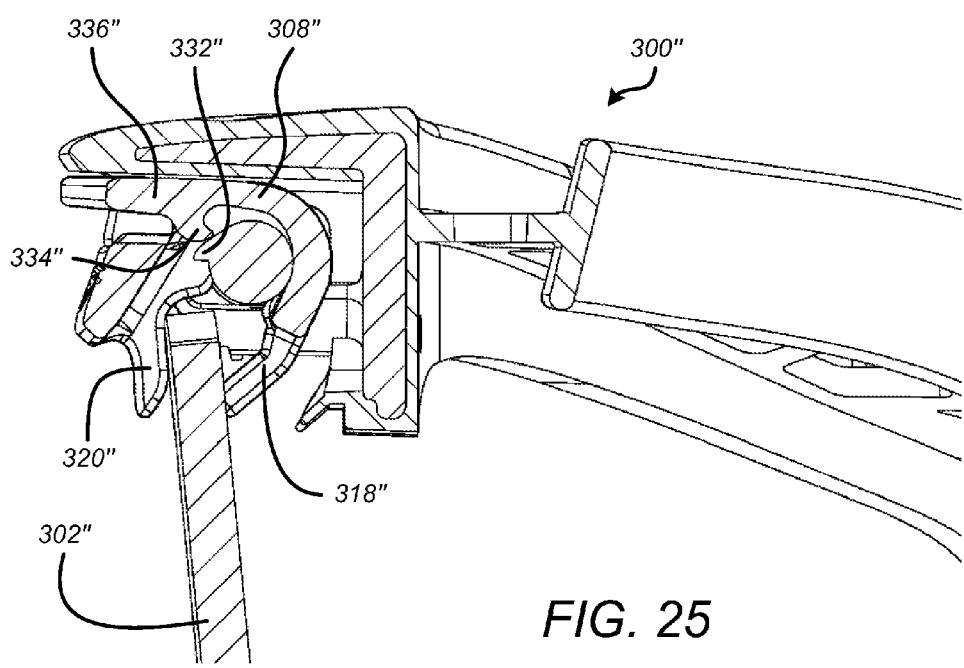
FIG. 25 is a cross-sectional view of the lens retaining member of FIG. 24 in an open position.

FIG. 24 shows another example embodiment of a lens retaining member 308" in a closed position on a goggle 300". FIG. 25 shows the lens retaining member 308" in an open configuration. The lens retaining member 308" and other features of the goggle 300" can be similar to the corresponding features on other embodiments disclosed herein (e.g., goggle 300 and goggle 300'). Thus, features of the goggle 300" not specifically discussed can be the same as, or similar to the goggle 300, later described goggle 300', and/or other embodiments discussed herein. The lens retaining member 308", and other features described in connection with FIGS. 24 and 25, can be used as alternatives to the lens retaining member 308, and other corresponding features, on goggle 300. The lens retaining member 308" can be movable (e.g., rotatable) between a closed position (shown in FIG. 24) and an open position (shown in FIG. 25). When the lens retaining member 308" is in the closed position, the lens 302" can be in a closed position (as shown in FIG. 24), and when the lens retaining member 308" is in the open position, the lens 302" can be in the open position (as shown in FIG. 25). The goggle 300" can be configured to position the lens 302" in the field of view of the wearer when the lens 302" is in the closed and open positions.

The lens retaining member 308" can include one or more positioning features (e.g., hooked arm 334") that are configured to engage with one or more corresponding features on the frame (e.g., tooth 332") for positioning the lens retaining member 308". For example, when the lens retaining member 308" is in the closed position, the hooked arm 334" can be disposed on a first side of (e.g., below) the tooth 332" (see FIG. 24). A threshold amount of force can be needed to overcome the engagement between the hooked arm 334" and tooth 332" to cause the lens retaining member 308" to toggle from the closed position to the open position. For example, a sufficient force applied to the tab 336" in an upward direction can cause the hooked arm 334" to disengage from the tooth 332" to allow the lens retaining member 308" to toggle to the open position. When the lens retaining member 308" is in the open configuration, the hooked arm 334" can be positioned on a second side of (e.g., above) the tooth 332" (see FIG. 25). A threshold amount of force can be needed to overcome the engagement between the hooked arm 334" and the tooth 332" to toggle the lens retaining member 308" from the open position to the closed position. As discussed further herein, a sufficient force pushing the lens rearward (e.g., towards the wearer's face) can cause the lens 302" and the lens retaining member 308" to toggle to the closed position. Also, a sufficient force pushing the front arm 320" of the lens retaining member 308" rearward (e.g., towards the wearer's face) can cause the lens retaining member 308" to toggle to the closed position.

In some embodiments, the lens retaining member 308" does not have a dedicated position for releasing the lens 302". In some embodiments, the lens retaining member 308" can deform past the open position (shown in FIG. 25) to permit the lens 302" to be removed. To remove the lens 302", the lens retaining member 308" can be toggled to the open position. The lens 302" can then be removed by pushing the lens forward (e.g., away from the wearer's face) when the lens retaining member 308" is in the open position. The force of the lens 302" pushing forward on the front arm 320" can cause the lens retaining member 308" to elastically deform sufficiently beyond the open position to allow the lens 302" to release from the frame. For example, the deformation can cause the front arm 320" to deflect forward and/or upward from the open position shown in FIG. 25. Once the lens retaining member 308" has deformed sufficiently, the top edge of the lens 302" can pass forward past the front arm 320". In some embodiments, the lens 302" can then be lifted generally upwardly, which can disengage one or more tabs on the lens 302" (e.g., tabs on lower portions or cheek portions of the lens 302", not shown in FIGS. 24 and 25) from corresponding slots in the frame (e.g., slots on lower portions or cheek portions of the frame, not shown in FIGS. 24 and 25).

In some embodiments, the lens 302" is not removable by actuating the lens retaining member 308". This can prevent the lens 302" from being unintentionally released by unintentionally actuating the lens retaining member 308" past the open position to the releasing position. In some embodiments, the tab 336" can abut against or be positioned near a portion of the frame when in the open position, and the portion of the frame can serve as a stop to prevent a force on the tab 336" from actuating the lens retaining member 308" past the open position.

Accordingly, a method of moving the lens to an open position to increase ventilation through the goggle 300" can include pushing the tab 336" (e.g., in a generally upward direction) to move (e.g., rotate) the lens retaining member 308" from the closed position to the open position. The rear arm 318" can push the lens 302" forward to the open position to increase ventilation through the eyewear. Thus, the lens 302" can be opened by pushing on a single location, as opposed to pinching two objects together, pushing two locations simultaneously, holding one object or portion while moving a different object or portion, etc. The lens 302" can be closed by pushing the lens 302" (e.g., rearward) or by pushing the front arm 320" (e.g., rearward). Thus, the lens 302" can be closed by pushing on a single location. Accordingly, the lens 302" can be opened and/or closed with a single hand, with a single hand wearing a glove, and/or with a single hand while holding an object, etc. The wearer does not need to grip anything to open and/or close the lens 302". This can be advantageous by enabling the wearer to increase ventilation (e.g., to defog the eyewear) and/or close the goggle 300 while the wearer's hands are engaged with other objects (e.g., during a combat situation).

Figure 27:
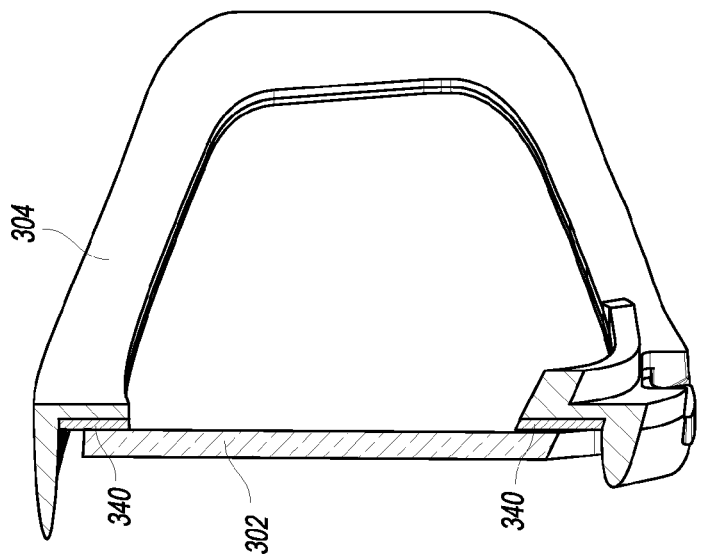
FIG. 27 is a cross-sectional view of the goggle in the closed configuration.
Figure 26:
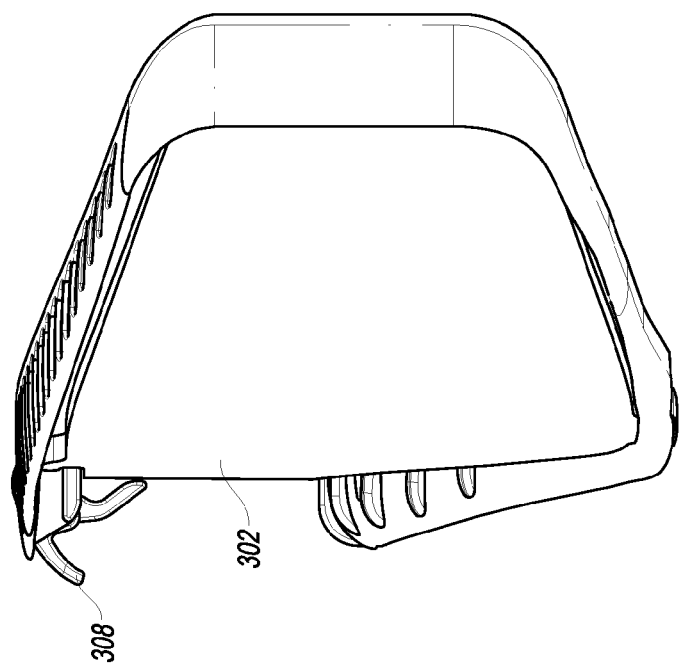
FIG. 26 is a side view of the goggle in the closed configuration.

FIG. 26 is a side view of the goggle 300 in the closed configuration. FIG. 27 is a cross-sectional view of the goggle 300 in the closed configuration. In the closed configuration, the lens 302 can abut against the frame 304 to create a seal that substantially prevents dust and debris from passing between the lens 302 and the frame 304. In some embodiments, the frame 304 can include a gasket 340, which can be formed of a flexible and resilient material and the gasket 340 can be configured to facilitate sealing between the lens 302 and the frame 304.

Figure 29:
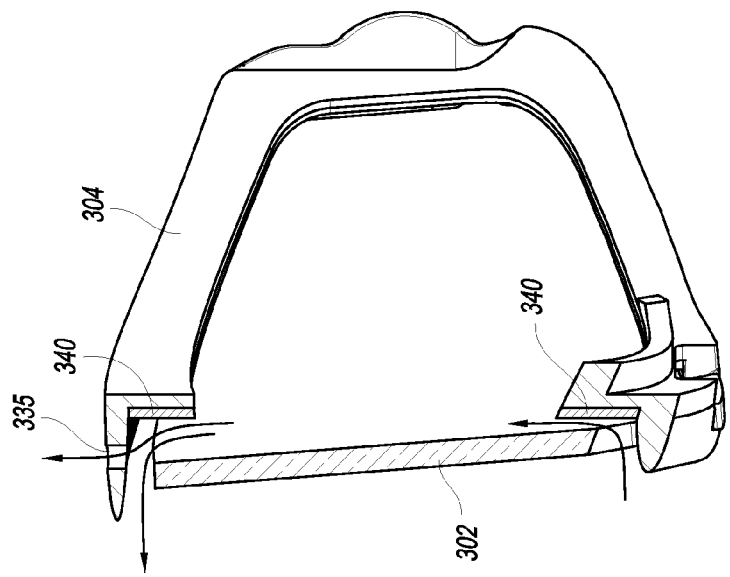
FIG. 29 is a cross-sectional view of the goggle in the open configuration.
Figure 28:
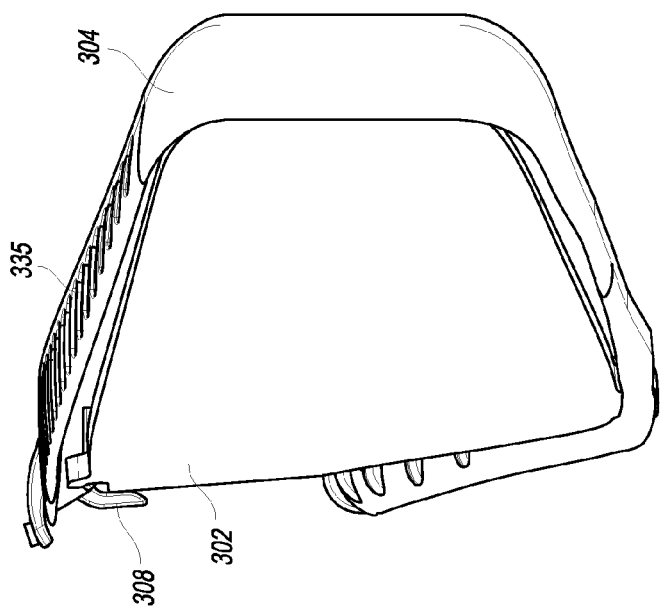
FIG. 28 is a side view of the goggle in the open configuration.

FIG. 28 is a side view of the goggle 300 in the open configuration. FIG. 29 is a cross-sectional view of the goggle 300 in the open configuration. In the open configuration, the at least part of the lens 302 can be displaced forward from the frame 304, thereby allowing air to pass between the lens 302 and the frame 304. The goggle 300 can create a chimney effect, in which fresh air can enter the goggle 300 from the bottom and side portions of the goggle 300 and can exit the goggle 300 at the top thereof, as shown by the arrows in FIG. 29. The goggle 300 can be configured to allow the air to enter and exit the goggle 300 at areas adjacent to the lens 302 so that air flows through the goggle 300 near the lens 302 and can be used to rapidly defog the lens 302 by flushing humid air out of the goggle 300. In some embodiments, the brow portion of the frame 304 can include one or more openings (e.g., slits 335) that allow air to pass upward through the brow portion 324 as shown in FIG. 29. In some embodiments, the brow portion 324 can extend forward past the opening formed between the lens 302 and the frame 304 when the lens 302 is in the open position. The brow portion 324 can protect the goggle 300 from debris from falling through the vent opening at the top of the goggle 300. In some embodiments, the slits 335 can be omitted so that the brow portion 324 can provide improved protection from debris entering the goggle 300. The openings (e.g., slits 335) can be sized such that the goggle 300 has no openings wider than a threshold size for which a linear line can be drawn from a location outside the goggle 300, through the opening, to a location inside the goggle 300 (e.g., that is behind the frame 304). In some embodiments, the threshold size can be less than or equal to about 3 mm, less than or equal to about 2 mm, less than or equal to about 1.5 mm, less than or equal to about 1.0 mm, or less than or equal to about 0.5 mm. For example, the openings (e.g., slits 335) can have a width or diameter that is less than or equal to about 3 mm, less than or equal to about 2 mm, less than or equal to about 1.5 mm, less than or equal to about 1.0 mm, or less than or equal to about 0.5 mm. The openings (e.g., slits 335) can have a width or diameter that is at least about 0.1 mm, at least about 0.25 mm, at least about 0.5 mm, or at least about 1.0 mm. The openings (e.g., slits 335) can be configured such that the openings are in communication with the interior of the goggle 300 when the lens 302 is in the open position, and the openings are not in communication with the interior of the goggle 300 when the lens 302 is in the closed position. Thus, when the lens 302 is closed, the openings do not provide venting to the goggle 300, and when the lens 302 is open, the openings do provide ventilation for the goggle 300.

In some embodiments, the lens 302 can pivot about one or more pivot locations (e.g., at the bottom of the lens 302) when the lens 302 moves between the closed, open, and releasing positions. As can be seen in FIGS. 17 and 18, the lens can include pivot tabs 342*a* and 342*b*, which can be positioned on the lower portion of the lens 302, such as at or near the lowest points on the lens 302, with one tab 342*a* on one side of the lens 302 and another tab 342*b* on the other side of the lens 302. The frame 304 can include slots 344*a* and 344*b* that are configured to receive the tabs 342*a* and 342*b*. When the lens 302 is driven to different locations between the open configuration, the closed configuration, and the releasing configuration, the tabs 342*a* and 342*b* and remain engaged with the slots 344*a* and 344*b*, so that the lens 302 pivots about the interface between the tabs 342*a* and 342*b* and the slots 344*a* and 344*b*. The tabs 342*a* and 342*b* and slots 344*a* and 344*b* can be shaped so that the tabs 342*a* and 342*b* engage the slots 344*a* and 344*b* to secure the lens 302 to the bottom of the frame 304 when the lens 302 is in the closed or open (vented) positions, thereby preventing the lens 302 from moving vertically upwardly (e.g., in the event of a deformation of the goggle, such as during a ballistic impact). The tabs 342*a* and 342*b* and slots 344*a* and 344*b* can be shaped so that the tabs 342*a* and 342*b* disengage from the slots 344*a* and 344*b* when the lens 302 is moved to the releasing position (e.g., forward of the open, vented position) to allow the lens 302 to be moved upwardly away from the frame 304 to release the lens 302. When pivoted forward to the open configuration, the lens 302 can be closer to the frame 304 at the bottom of the lens 302 and further from the frame 304 at the top of the lens 302. In some cases the air vent area at the top of the lens 302 can be larger than the air vent area at the bottom and/or sides of the lens 302.

Figure 30:
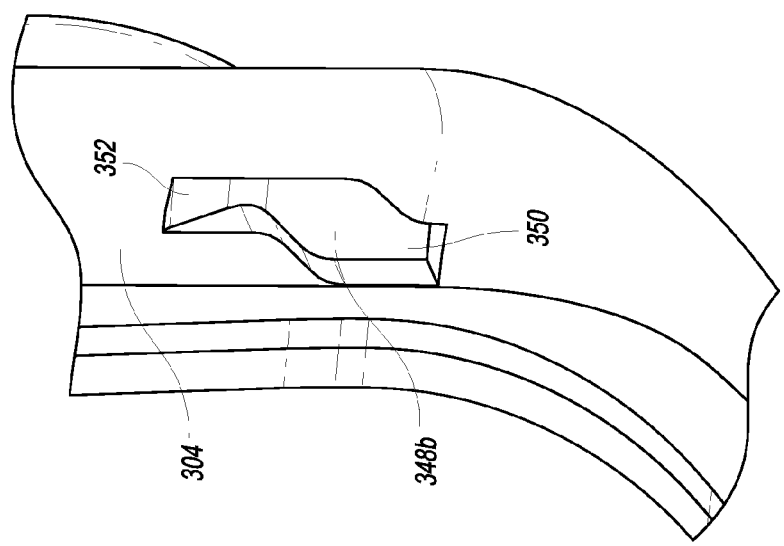
FIG. 30 shows a detailed isometric view of a groove in the frame of the goggle.

In some embodiments, the goggle 300 can include additional lens retention features and the goggle 300 can include features that are configured to increase the size of the air vents, e.g., at the sides and/or bottom of the lens 302. For example, as shown in FIGS. 17 and 18, the lens 302 can include tabs 346a and 346b positioned at the sides of the lens 302. The tabs 346a and 346b can be configured to engage grooves 348a and 348b that can be formed on the inward facing sides of the frame 304. In some embodiments, the tabs 346a and 346b can be positioned at laterally opposite sides of lens 302 (e.g., at the temples), and the corresponding grooves 348a and 348b can be formed on laterally opposite sides of the frame 304 (e.g., at the temples). FIG. 30 shows a detailed isometric view of the groove 348b (which can have a similar shape and function as the other groove 238a). The groove 348b can include a lower portion 350 and an upper portion 352. When the lens 302 is in the closed position, the tabs 346a and 346b can be positioned in the lower positions 350 of the grooves 348a and 348b. The lower portion 350 of the groove 348b can be configured to snuggly secure the lens 302 to reduce or prevent play in the lens 302 when in the closed position. For example, in some embodiments, the lower portion 350 of the groove 348b can be thin enough such that the tab 346b can fit snuggly therein to reduce or prevent play in the lens 302 when in the closed position. In some embodiments, the lower portion 350 of the groove 348b can be positioned sufficiently rearward to press the lens 302 snuggly against the gasket 340 that is disposed between the lens 302 and the frame 304. As the lens 302 pivots forward to the open position, the tabs 346a and 346b can slide up the grooves 348a and 348b towards the upper portions 352 thereof. In some embodiments, the grooves 348a and 348b can be configured to apply force to the lens 302 as the tabs 346a and 346b slide to the upper portions 352 thereof, thereby causing the lens 302 to deform when in the open configuration, and the deformation of the lens 302 can increase the air vent area (e.g., at the sides and/or bottom of the lens 302). For example, the upper portions 352 of the grooves 348a and 348b can be positioned further forward than the lower portions 350 thereof, such that the upper portions 352 of the grooves 348a and 348b can press the tabs 346a and 346b forward as the tabs 346a and 346b slide up to the upper portions 352 of the grooves 348a and 348b, thereby deforming the lens 302 (e.g., by increasing the radius of curvature thereof). In some embodiments, the tabs 346a and 346b and the grooves 348a and 348b can cause substantially no deformation in the lens 302 when lens 302 is transitioned between the closed and open positions. The grooves 348a and 348b can be longer than the tabs 346a and 346b so that the tabs 346a and 346b can slide in the grooves 348a and 348b when the lens 302 moves between the closed and open positions. The upper portions 352 of the grooves can be further forward than the lower portions 350 of the grooves such that the tabs 346a and 346b can move into the upper portions 352 as the lens 302 moves forward to the open position without pinching the tabs 346a and 346b and without substantially deforming the lens 302. Because the grooves 348a and 348b allow the tabs 346a and 346b to move forward with the lens 302 as it moves toward the open position, the grooves 348a and 348b can increase the size of the opening between the lens 302 and the frame (e.g., at the lateral portions of the goggle 300), as compared to an embodiment in which the tabs 346a and 346b are not permitted to slide forward with the lens 302. In some embodiments, the tabs 346a and 346b and the grooves 348a and 348b can be configured to maintain the lens 302 in the closed position against the frame 304 in situations where the goggle structure may be deformed (e.g., a ballistic impact or handling by the user).

Figure 31:
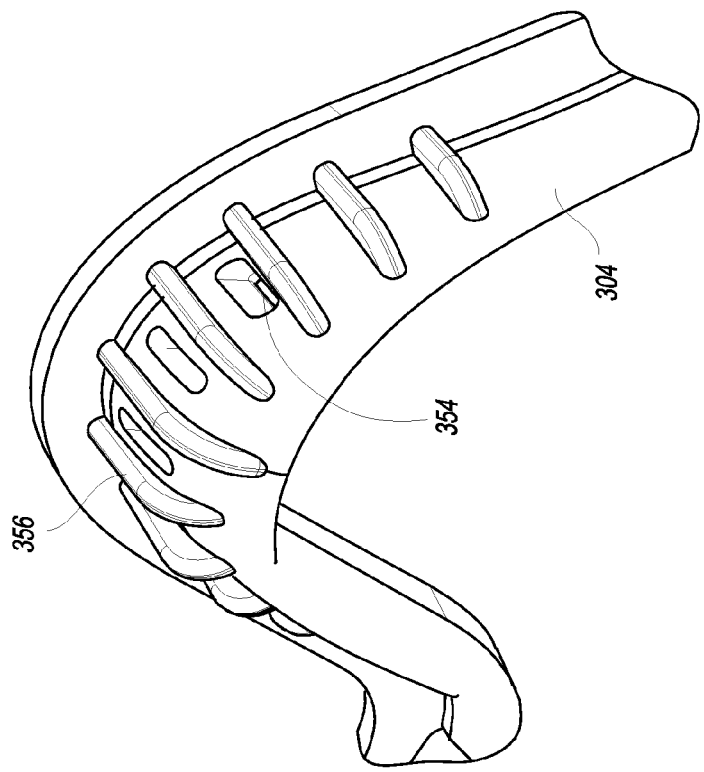
FIG. 31 shows a detailed isometric view of the nose portion of the frame.
Figure 32:
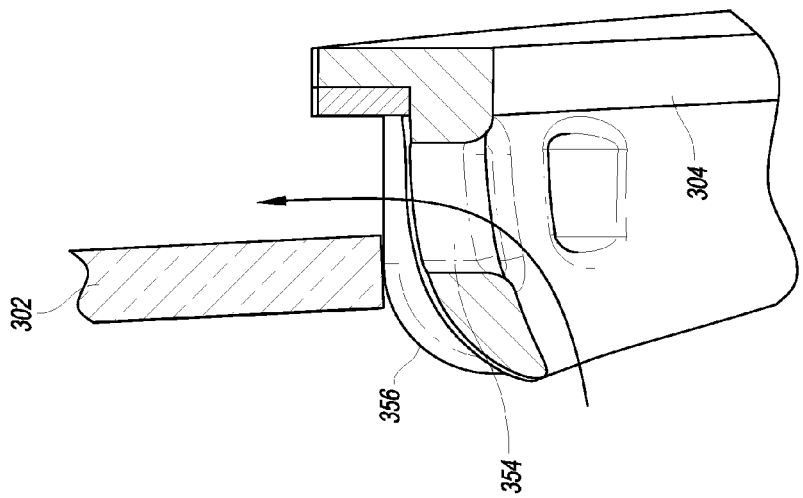
FIG. 32 shows a cross-sectional view of the nose portion of the frame and the lens in an open configuration.

FIG. 31 shows a detailed isometric view of the nose portion of the frame 304. FIG. 32 shows a cross-sectional view of the nose portion of the frame 304 and the lens 302 in an open configuration. The nose portion of the frame 304 can include one or more openings (e.g., slits 354) that extend through the frame 304. In the illustrated embodiments, four slits can be formed near the top of the nose arc. As can be seen in FIG. 32, at least a portion of the slits 354 can be positioned rearward of the lens 302 when the lens 302 is in the open configuration, so that air can pass through the slits 354 and can enter the goggle 300 behind the lens 302. The openings (e.g., slits 354 can be sized such that the goggle 300 has no openings wider than a threshold size for which a linear line can be drawn from a location outside the goggle 300, through the opening, to a location inside the goggle 300 (e.g., that is behind the frame 304). In some embodiments, the threshold size can be less than or equal to about 3 mm, less than or equal to about 2 mm, less than or equal to about 1.5 mm, less than or equal to about 1.0 mm, or less than or equal to about 0.5 mm. For example, the openings (e.g., slits 354) can have a width or diameter that is less than or equal to about 3 mm, less than or equal to about 2 mm, less than or equal to about 1.5 mm, less than or equal to about 1.0 mm, or less than or equal to about 0.5 mm. The openings (e.g., slits 354) can have a width or diameter that is at least about 0.1 mm, at least about 0.25 mm, at least about 0.5 mm, or at least about 1.0 mm. The openings (e.g., slits 354) can be configured such that the openings are in communication with the interior of the goggle 300 when the lens 302 is in the open position, and the openings (e.g., slits 354 are not in communication with the interior of the goggle 300 when the lens 302 is in the closed position. Thus, when the lens 302 is closed, the openings (e.g., slits 354) do not provide venting to the goggle 300, and when the lens 302 is open, the openings (e.g., slits 354) do provide ventilation for the goggle 300.

Figure 33:
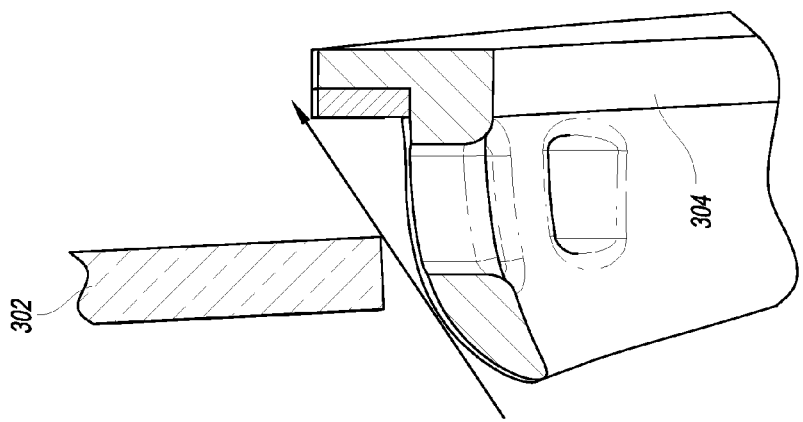
FIG. 33 shows a cross-sectional view with an opening between the lens and frame through which a linear line can be drawn from a location outside the goggle to a location inside the goggle.

The nose portion of the frame 304 can also include one or more ridges 356 formed on the top thereof. The ridges 356 can be configured to reduce the size of openings the lead into the interior of the goggle 300. In some embodiments, it can be desirable to eliminate, or minimize the size of, openings in the goggle 300 through which a linear line can be drawn from a location outside the goggle 300 to a location inside the goggle 300 (e.g., that is behind the frame 304). Linear openings, like that shown in FIG. 33, can allow shrapnel, flying debris, or other projectiles to enter the goggle 300, which can endanger the eyes of the wearer. In some embodiments, the lens 302 of the goggle 300 can be spaced apart from the frame 304 when in the open configuration, thereby creating an opening between the lens 302 and the frame 304. The opening can allow air to pass therethrough for ventilating the goggle 300, as discussed herein. In some cases, the openings between the lens 302 and the frame 304 can be configured to provide a bent pathway into the goggle 300, such that a linear line cannot be drawn from a location outside the goggle 300, through the opening, to a location inside the goggle 300 (e.g., that is behind the frame 304), such as, for example, the opening formed at the bottom of the lens 302 in FIG. 29. In some embodiments, when the goggle 300 is in the open configuration, the goggle 300 can include no openings wider than a threshold size for which a linear line can be drawn from a location outside the goggle 300, through the opening, to a location inside the goggle 300 (e.g., that is behind the frame 304). In some embodiments, the threshold size can be less than or equal to about 3 mm, less than or equal to about 2 mm, less than or equal to about 1.5 mm, less than or equal to about 1.0 mm, or less than or equal to about 0.5 mm.

As mentioned above, the ridges 356 on the nose portion of the frame 304 can be configured to eliminate, or reduce the size of, linear openings into the goggle 300. FIG. 34 shows a perspective view of the goggle 300. FIG. 35 shows a detailed view of the nose portion of the goggle 300 as shown in FIG. 34. FIG. 36 shows a detailed view of the nose portion of the goggle 300 with the ridges 356 omitted from view. As can be seen in FIG. 36, without the ridges 356, an opening 358 between the frame 304 and the lens 302 would provide a linear path into the goggle 300. By comparing FIGS. 35 and 36, it can be seen that the ridges 356 can eliminate, or reduce the size of, linear openings into the goggle 300.

Figure 38:
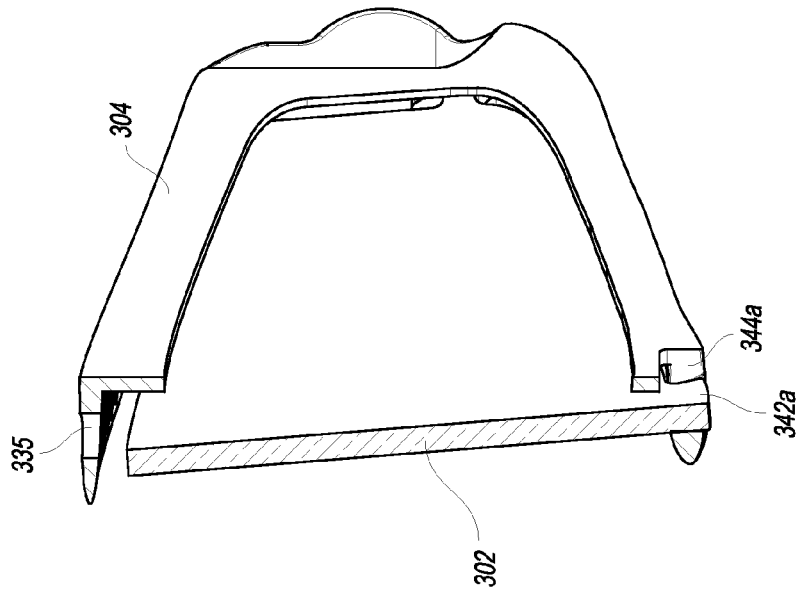
FIG. 38 shows a cross-sectional view of the goggle in the releasing configuration.
Figure 37:
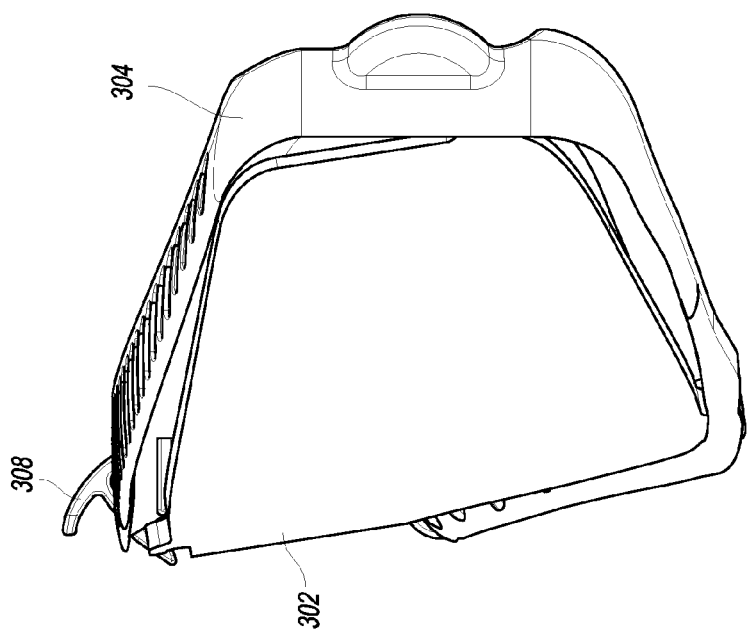
FIG. 37 shows a side view of the goggle in the releasing configuration.

In some embodiments, the lens 302 can be removable from the frame 304, so that the lens 302 can be interchanged with other lenses. FIG. 37 shows a side view of the goggle 300 in the releasing configuration. FIG. 38 shows a cross-sectional view of the goggle 300 in the releasing configuration taken through a plane that intersects the tab 342a and the slot 344a. To remove the lens 302, the wearer can grip the top portion of the lens 302 and lift the lens 302 (as shown by the arrow in FIG. 38) until the tabs 342a and 342b disengage from the slots 344a and 344b. The lens 302 can be attached to the frame 304 by lowering the tabs 342a and 342b into the slots 344a and 344b and then pivoting the lens 302 back towards the frame 304.

In some embodiments, the goggle 300 can be impact resistant. For example, the goggle 300 can be configured to resist ballistic impacts, for example, for combat uses. The lens retaining member 308 can be configured to retain the lens 302 onto the frame 304 in the event of an impact on the lens 302. And the lens retaining member 308 can be configured to maintain the closed lens 302 in the closed position in the event of an impact on the lens 302. With reference to FIGS. 19 and 20, the positioning features (e.g., the hooked arms 334a and 334b) that are configured to hold the lens retaining member 308 in the closed position can be located on the front side thereof (e.g., next to the front arm 320 of the clip 316), and the hooked arms 334a and 334b can be coupled to the clip 316 at on the back side thereof. Extension arms 360a and 360b can extend rearward from the hooked arms 334a and 334b on the front side of the clip 316 and can couple to the clip 316 at junctions 362a and 362b on the back side of the clip 316. Gaps 364a and 364b can extend between the clip 316 and the extension arms 360a and 360b. Coupling the hooked arms 334a and 334b to the clip 316 on the back side thereof can facilitate retention of the lens 302 in the closed position during in impact on the lens 302.

Figure 39:
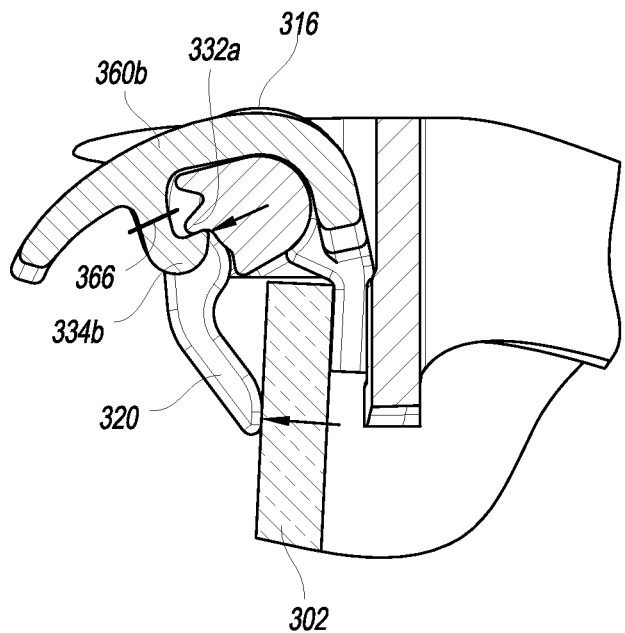
FIG. 39 shows the lens retaining member with a junction positioned on the front side thereof.

With reference to FIG. 39, an impact on the lens 302 can cause the lens to rebound, thereby applying a force that pushes against the front arm 320 of the clip 316. If the hooked arms 334a and 334b were coupled to the clip 316 on the front side thereof (e.g., at junction 366), the force of the lens rebound 302 would be transferred into the hooked arms 334a and 334b in a forward direction that could push the hooked arms 334a and 334b off of the lower tooth 332a. Thus, if the hooked arms 334a and 334b were coupled to the clip 316 at junction 366 on the front of the clip 316, a lens impact of sufficient force could transition the lens 302 to the open configuration, or to the releasing configuration, and could cause the lens 302 to disengage from the frame 304.

Figure 40A:
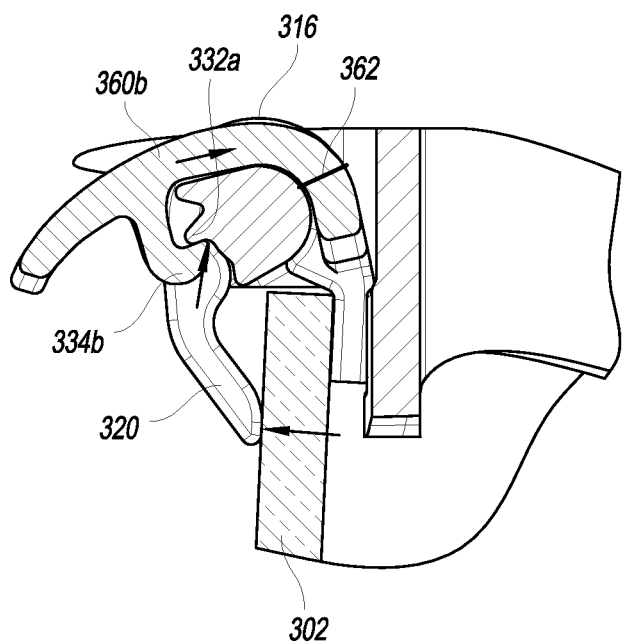
FIG. 40A shows the lens retaining member with the junction positioned at the back side thereof.

FIG. 40A shows the lens retaining member 308 with the junction 362 positioned rearward of the interface between the hooked arms 334a and 334b and the teeth 332a and 332b. The junction 362 can be positioned rearward of the teeth 332a and 332b and/or rearward of the engagement bar 328. The force of the lens rebound can be transferred through the front arm 320 of the clip 316 and to the back side of the clip 316, wherein the force can be transferred through the junction 362 into the extension arms 360a and 360b and the hooked arms 334a and 334b. Because the force on the hooked arms 334a and 334 is directed rearward (e.g., a pulling force from the junction 362 applied through the rearward extending extension arms 360a and 360b), the force of the lens rebound can cause the hooked arms 334a and 334b press harder against the engagement bar 328 to further engage the tooth 332a, instead of pushing the hooked arms 334a and 334b forward as in FIG. 39. Thus, coupling the hooked arms 334a and 334b to the back side of the clip 316 can facilitate retention of the lens 302 in the closed position in the event of lens impact. In some embodiments, the one or more positioning features (e.g., hooked arms 332a and 332b) can be positioned on a first side of the lens retaining member 316 and the junction 362 can be positioned on a second side of the lens retaining member 316 substantially opposite the first side, so that a force transferred through the junction 362 to the hooked arms 332a and 332b causes the hooked arms 332a and 332b to further engage the frame 304 to prevent unintentional opening or release of the lens 302.

In some instances, a lens impact can also cause the frame 304 to deform. In some cases, the brow portion 324 of the frame can deform by deflecting upward, which can cause the lens 302 to disengage from the lens retaining member 308 and/or release from the frame 304. In some embodiments, the lens 302 can includes one or more engagement features that are configured to engage corresponding engagement features on the frame 304 to prevent or reduce deformation of the frame 304 and/or facilitate retention of the lens 302 on the frame 304 in the event of a lens impact. The engagement features can be positioned on the brow portion 324 of the frame 304 and on the upper periphery of the lens 302. For example, with reference now to FIGS. 17 and 18, the lens 302 can include one or more hooks 368a and 368b at the periphery of the lens 302 (e.g., at the top central portion of the periphery of the lens 302). The hooks 368a and 368b can be configured to engage corresponding engagement surfaces 370a and 370b on the brow 324 of the frame 304, so that in the event of a lens impact, deformation of the brow portion 324 can cause the engagement surfaces 370a and 370b to pull on the lens hooks 368a and 368b. Coupling the lens 302 to the brow portion 324 of the frame 304 can provide support and added rigidity to the brow portion 324, thereby reducing the amount of brow portion deflection during a lens impact. In some cases, upward deflection of the brow portion 324 can pull the lens 302 upward as well, thereby preventing the lens from disengaging from the frame 304.

In some embodiments, the goggle 300 can have unfiltered venting when in an open configuration (e.g., venting between the lens 302 and frame 304, or venting at other locations that are not covered or filtered). In some embodiments, the goggle 300 can include filtered venting (e.g., through the intermediate portion 314 shown in FIGS. 17 and 18) which can be covered by a filtering material. In some cases the filtered venting can provide venting to the goggle 300 when the goggle 300 is in the closed and open positions, and the unfiltered venting can provide venting when the goggle 300 is open and not when the goggle 300 is closed. Venting area can refer to the sum of the area of all apertures on the goggle 300 through which air can pass in or out of the goggle 300, without considering the presence or absence of a filtering material. For example, the top of intermediate portion 314 includes a plurality of distinct apertures separated by struts. The venting area through the intermediate portion 314 is thus the sum of the area of the individual apertures in intermediate portion 314. If a foam material or other filtering material is disposed over the intermediate portion 314, the filtering material does not change the amount of venting area of the intermediate portion 314. With the filtering material, the venting area of intermediate portion 314 is considered to be filtered venting area. Venting areas that allow exchange of air without a filtering material are considered unfiltered venting area. For example, in some embodiments, the area between the open lens 302 and the frame 304 can allow air to pass in and out of the goggle 300 without passing through a filtering material, and that area is considered to be unfiltered venting area. Other unfiltered venting areas can be provided, such as by an opening on the frame that can be opened or closed to change the amount of unfiltered venting. When in the open configuration, the goggle 300 can include an unfiltered venting area of at least about 900 mm$^2$, at least about 1000 mm$^2$, at least about 1100 mm$^2$, at least about 1200 mm$^2$, at least about 1230 mm$^2$, at least about 1250 mm$^2$, or more. The unfiltered venting area of the goggle 300 in the open configuration can be less than or equal to about 2000 mm$^2$, less than or equal to about 1500 mm$^2$, less than or equal to about 1300 mm$^2$, less than or equal to about 1250 mm$^2$, less than or equal to about 1230 mm$^2$, or less. The goggle 300 can have a closed configuration and an open configuration, and the increase of venting area between the closed configuration and the open configuration can be an area of at least about 900 mm$^2$, at least about 1000 mm$^2$, at least about 1100 mm$^2$, at least about 1200 mm$^2$, at least about 1230 mm$^2$, at least about 1250 mm$^2$, or more. In some embodiments, the increase of the venting area between the closed and open configurations can be less than or equal to about 2000 mm$^2$, less than or equal to about 1500 mm$^2$, less than or equal to about 1300 mm$^2$, less than or equal to about 1250 mm$^2$, less than or equal to about 1230 mm$^2$, or less. In some embodiments, the increased venting area from the closed configuration to the open configuration can be unfiltered venting area, and in some embodiments, the increased venting area from the closed configuration to the open configuration can be filtered venting area. For example, as described in connection with FIGS. 40J and 40K, in some embodiments, some or all of the area between the lens 302 and the frame 304 can be filtered when the lens 302 is in the open position. In some embodiments, the goggle 300 having the described venting area can still be of a size that is compatible with military night vision systems, and can still be worn with a military helmet. For example, in some embodiments, the volume of the goggle 300 can include area occupied by the goggle 300 itself and the area inside the goggle 300 that is enclosed by an imaginary surface that extends between the rearward edges of the face flange 306. The volume of the goggle 300 can be less than or equal to about 300 cm$^3$, less than or equal to about 250 cm$^3$, less than or equal to about 225 cm$^3$, less than or equal to about 200 cm$^3$, less than or equal to about 175 cm$^3$, less than or equal to 150 cm$^3$, or less. The volume of the goggle 300 can be at least about 100 cm$^3$, at least about 150 cm$^3$, at least about 175 cm$^3$, at least about 200 cm$^3$, at least about 225 cm$^3$, or more.

Figure 40B:
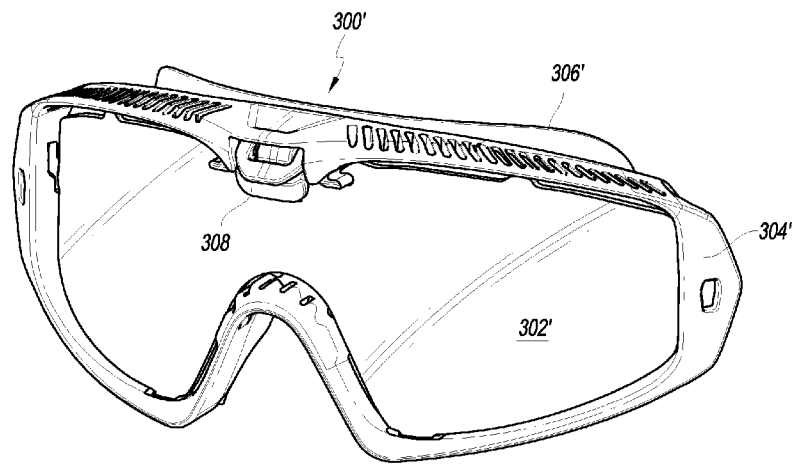
FIG. 40B is a front perspective view of an example embodiment of eyewear, which can be a goggle.
Figure 40C:
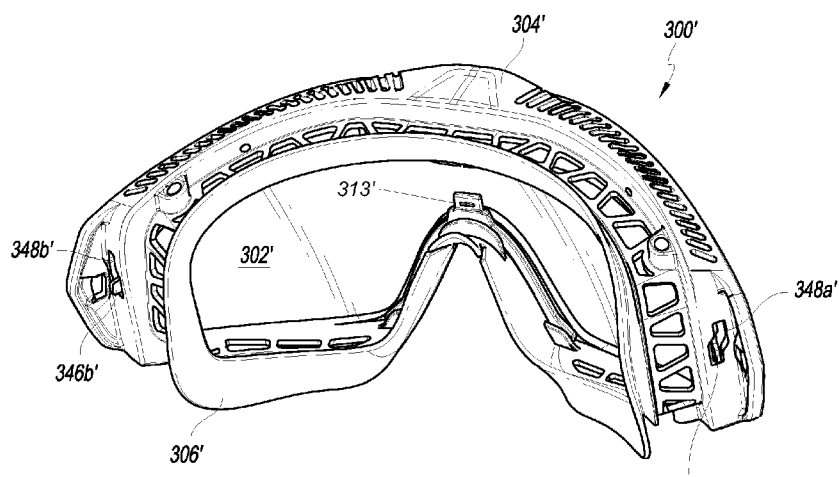
FIG. 40C is a rear perspective view of the goggle of FIG. 40B.
Figure 40D:
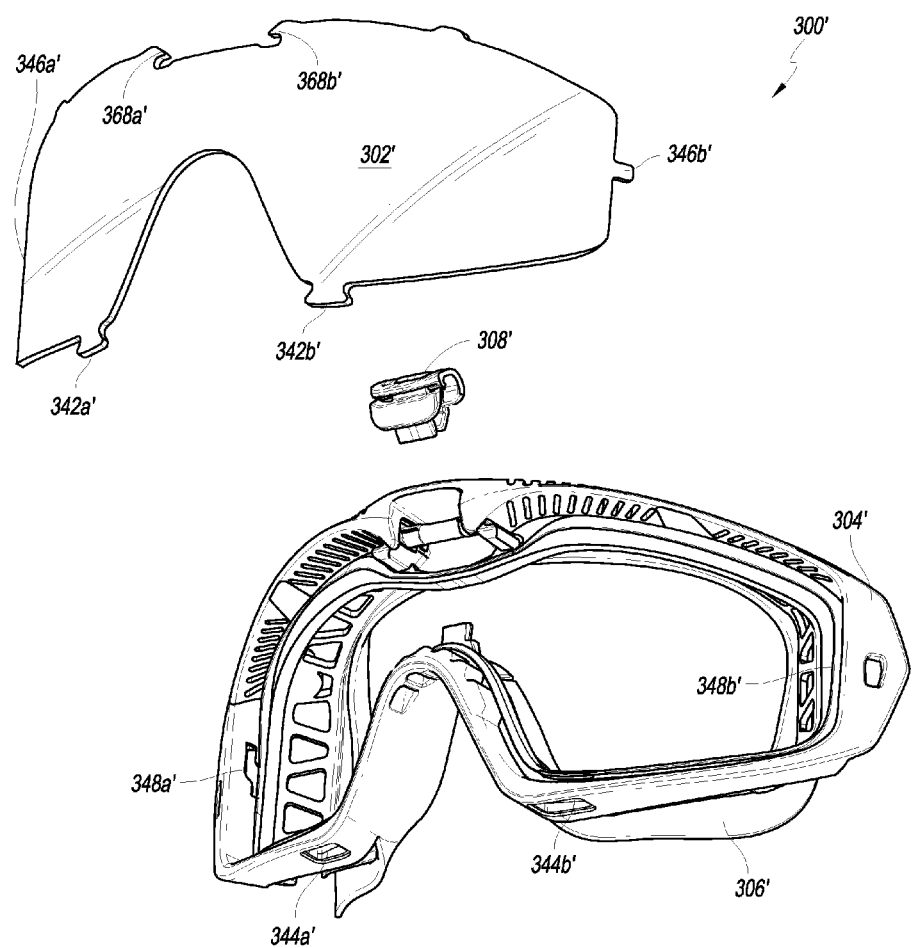
FIG. 40D is an exploded perspective view of the goggle of FIG. 40B.

FIG. 40B is a front perspective view of an example embodiment of eyewear (e.g., goggle 300'). FIG. 40C is a rear perspective view of the goggle 300'. FIG. 40D is an exploded perspective view of the goggle 300'. The goggle 300' can have various features similar to, or the same as, the goggle 300, the goggle 300", and/or other embodiments disclosed herein. Various features disclosed in connection with the other embodiments discussed herein can be incorporated into the goggle 300' even when not specifically discussed herein. Additionally, the features described in connection with the goggle 300' can be incorporated into the goggle 300, or into the other embodiments disclosed herein. The goggle 300' can include a frame 304' that supports a lens 302' similar to the goggle 300 discussed herein. A flange 306' (also referred to herein as a face flange) can extend from the back of the frame 304' and can be configured to conform to the face of a wearer. The goggle 300' can include a lens retaining member 308' for coupling the lens 302' to the goggle frame 304'. The goggle 300' can include a prescription attachment portion 313' configured to couple a prescription eyewear attachment (not shown) to the goggle 300'. The prescription attachment portion 313' can be similar to the prescription attachment portion 313 described herein. Various other embodiments disclosed herein (e.g., the goggle 300" can include a prescription attachment portion, which can be similar to the prescription attachment portions 313 and/or 313').

Figure 40E:
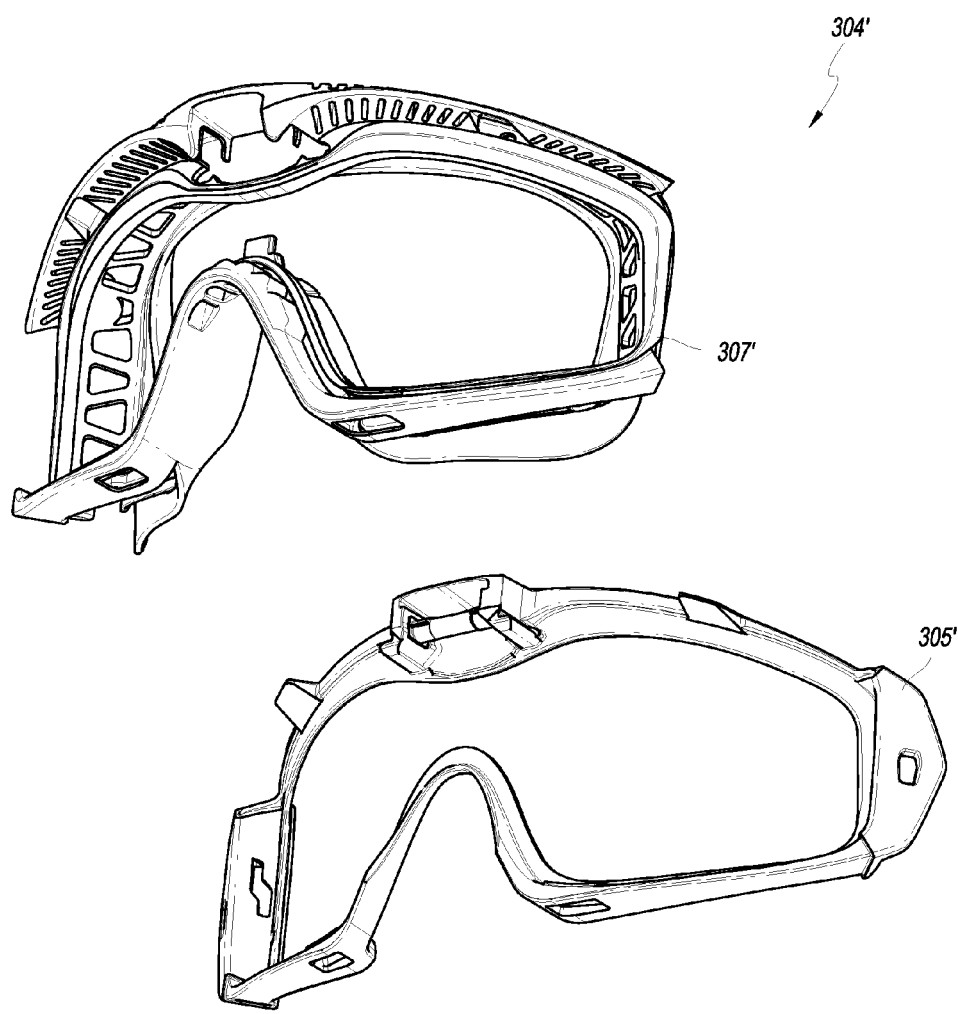
FIG. 40E is an exploded view of an example embodiment of a frame for use with the goggle of FIG. 40B.

With reference to FIG. 40E, the frame 304' can include a base member 305', and a covering 307', which, for example, can be overmolded over the base member 305'. In some embodiments, the base member 305' can be formed of a rigid or semi-rigid material, and the covering 307' can be formed of a generally flexible material.

Figure 40F:
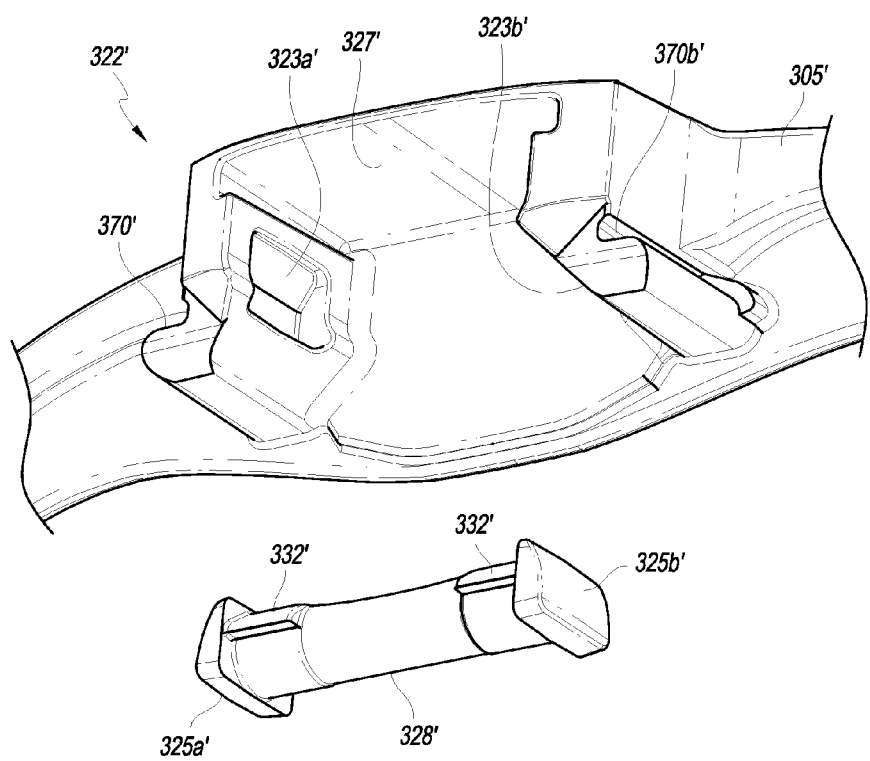
FIG. 40F is a partial view of frame showing an engagement portion of the frame.

The lens retaining member 308' can engage an engagement bar 328' in a manner similar to the goggle 300'. In some embodiments, the engagement bar 328' can be separately formed from the frame 304' and coupled to the frame 304' (e.g., using a clip, snap-fit, friction fit, adhesive, or other suitable attachment mechanism). For example, FIG. 40F shows an example embodiment of the engagement bar 328' and the frame base member 305' in a decoupled configuration. The engagement portion 322' of the frame 304' can include engagement members (e.g., recesses 323a' and 323b'), and the engagement bar 328' can include corresponding engagement members that are configured to engage the engagement members on the frame 304' to couple the engagement bar 328' to the frame 304'. For example, the engagement bar 328' can include end pieces 325a' and 325b' that are shaped to correspond to the recesses 323a' and 323b'. The end pieces 325a' and 325b' can have tapered ends to facilitate insertion of the engagement bar 328' into the engagement portion 322'. For example, the end pieces 325a' and 325b' can be thinner at the top portions thereof and wider at the bottom portions thereof. Although the engagement bar 328' can be integrally formed with the frame 304' (e.g., as in the goggle 300), the separately formed engagement bar 328' can be easier to mold than an engagement bar 328' that is integrally formed with the frame 304'.

In some embodiments, the engagement bar 328 can include a pair of teeth 332' configured to engage the lens retaining member 308' in a manner similar to the teeth 332a and 332b discussed in connection with the goggle 300. In some embodiments, a single tooth can be used instead of the pair of teeth 332'. The lens 302' can be toggled between a closed position and an open position, wherein the open position provides more ventilation through the goggle 300' than the closed position. When the lens 302' is in the open position, the lens 302' can be removed from the goggle 300' without toggling the lens retaining member 308' to a separate, lens removal position. The lens 302' can be removed (when in the open position), for example by applying a force to the lens in the forward direction (e.g., by pressing on the back surface of the lens 302' or by inserting one or more fingers around the edges of the lens 302' can pulling the lens 302' forward), which can cause the front arm 320' of the lens retaining member 308' to deform (as discussed below), thereby allowing the lens 302' to slip past the front arm 320' of the lens retaining member 308'. Then the lens 302' can be lifted upward to disengage the tabs 342a' and 342b' from the slots 344a' and 344b' (which are shown in FIG. 40D). The hooks 368a' and 368b' on the top of the lens 302' can engage the engagement surfaces 370a' and 370b' on the frame 304' in a manner similar to that described in connection with the goggle 300. In some embodiments, the hooks 368a' and 368b' can engage the engagement surfaces 370a' and 370b' when the lens 302' is in both the closed position and the open position. When the lens 302' is forced forward during disengagement, the hooks 368a' and 368b' can slide off of the front of the engagement surfaces 370a' and 370b' to facilitate removal of the lens 302'.

With further reference to FIG. 40F, the engagement portion 322' of the frame 304' can include an overhang portion 327' positioned over the lens retaining member 308'. When the lens retaining member 308' is rotated forward (e.g., to toggle the lens 302' to the open position), the overhang portion 327' can prevent the lens retaining member 308' from rotating further (e.g., past the open position). For example, the tab 336' of the lens retaining member 308' can abut against the underside of the overhang portion 327' to prevent the lens retaining member 308' from rotating past the open position.

Figure 40G:
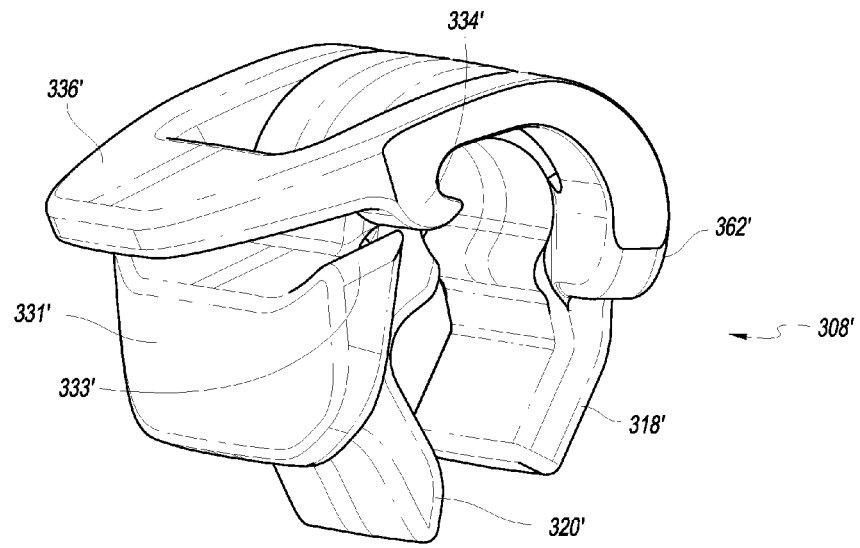
FIG. 40G is a perspective view of an example embodiment of a lens retaining member for use with the goggle of FIG. 40B.
Figure 40H:
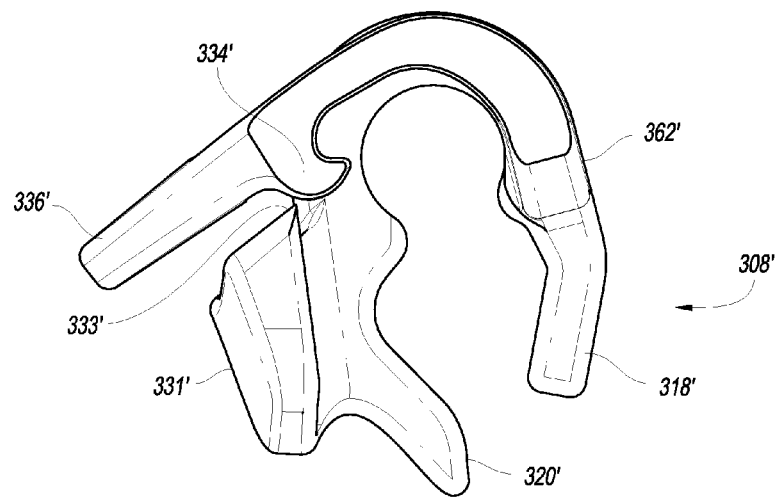
FIG. 40H is a side view of the lens retaining member of FIG. 40G.

FIG. 40G is a perspective view of an example embodiment of the lens retaining member 308'. FIG. 40H is a side view of the lens retaining member 308'. The lens retaining member 308' can have features similar to, or the same as, the lens retaining member 308 discussed above. Accordingly, various features of the lens retaining member 308' are not described in detail herein, and the disclosure relating to the lens retaining member 308 relates to the lens retaining member 308' as well. The lens retaining member 308' includes a back arm 318' and a front arm 320' configured to be positioned on either side of the lens 302' for pushing the lens 302' between the open and closed positions. Hooked arms 334' can be configured to engage the teeth 332' of the engagement bar 328', as described above. When the hooked arms 334' engage the teeth 332', the lens 302' can be held in the closed position (e.g., by the front arm 320'). When tab 336' is pressed upward by the user, the hooked arms 334' can disengage from the teeth 332' and the lens retaining member 308' can rotate to the open position (until the tab 336' abuts against the overhang portion 327').

In some embodiments, the hooked arms 334' can be coupled to the arms 318' and 320' at a junction 362' on the back of the lens retaining member 308' to prevent the lens retaining member 308' from unintentionally rotating to the open position in the event of lens impact (e.g., a ballistic impact). In some embodiments, the lens retaining member 308' can includes a locking element 331' that can prevent unintentional rotation of the lens retaining member 308' to the open position. The locking element 331' can be configured to lock the hooked arms 334' against the teeth 332' in the event of a lens impact event. For example, the locking element 331' can be positioned on the front of the front clip 320' such that a locking surface 333' is positioned near the hooked arm 334' on one or both sides of the lens retaining member 308'. An impact on the lens can cause the lens 302' to rebound forward, thereby pressing on the front arm 320' of the lens retaining member 308' and causing the front arm 320' to deform and rotate forward. The locking element 331' can rotate along with the front arm 320', which can cause the locking surface 333' to abut against the hooked arm 334' and press the hooked arm 334' against the tooth 332'. The stronger the lens 302' is pushed forward, the stronger the locking element 331' presses the hooked arms 334' against the teeth 332', thereby preventing the hooked arms 334' from unintentionally disengaging from the teeth 332'.

When in the open position (e.g., with the hooked arms 334' disengaged from the teeth 332' and disposed above the teeth 332'), the front arm 320' of the lens retaining member 308' can deform forward sufficiently to allow removal of the lens 302' before the locking element 331' abuts against the hooked arms 334' to prevent further movement of the front arm 320'.

Figure 40I:
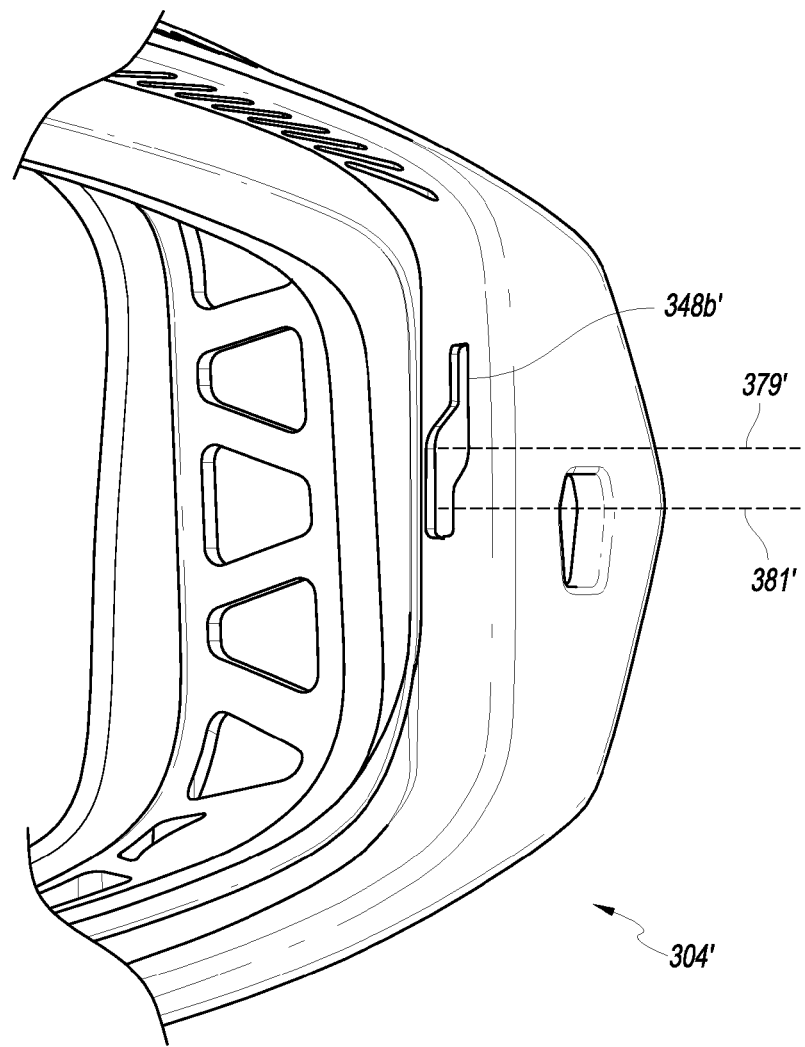
FIG. 40I is a partial front view of the frame.

The lens 302' can include tabs 346a' and 346b' disposed at the temporal sides of the lens 302', which can be configured to engage slots 348a and 348b in the frame 304' in a manner similar to the goggle 300. When the lens 302' is toggled to the open position, the slots 348a' and 348b' and tabs 346a' and 346b' can cause the lens 302' to deform in a manner similar to the goggle 300. In some embodiments, the slots 348a and 348b can be disposed on an upper portion of the temporal side of the frame 304', which can facilitate the deformation of the lens 302' to improve ventilation when the lens 302' is in the open position. For example, with reference to FIG. 40I, the center 379' of the slot 348b' can be positioned above the center 381' of the temporal side of the frame 304'. In some embodiments, a majority of the slot 348b' can be positioned above the center 381' of the temporal side. In some embodiments, substantially the entire slot 348b' can be positioned above the center 381' of the temporal side. The slot 348a' can be configured similar to the slot 348b' that is shown in FIG. 40I.

Figure 40J:
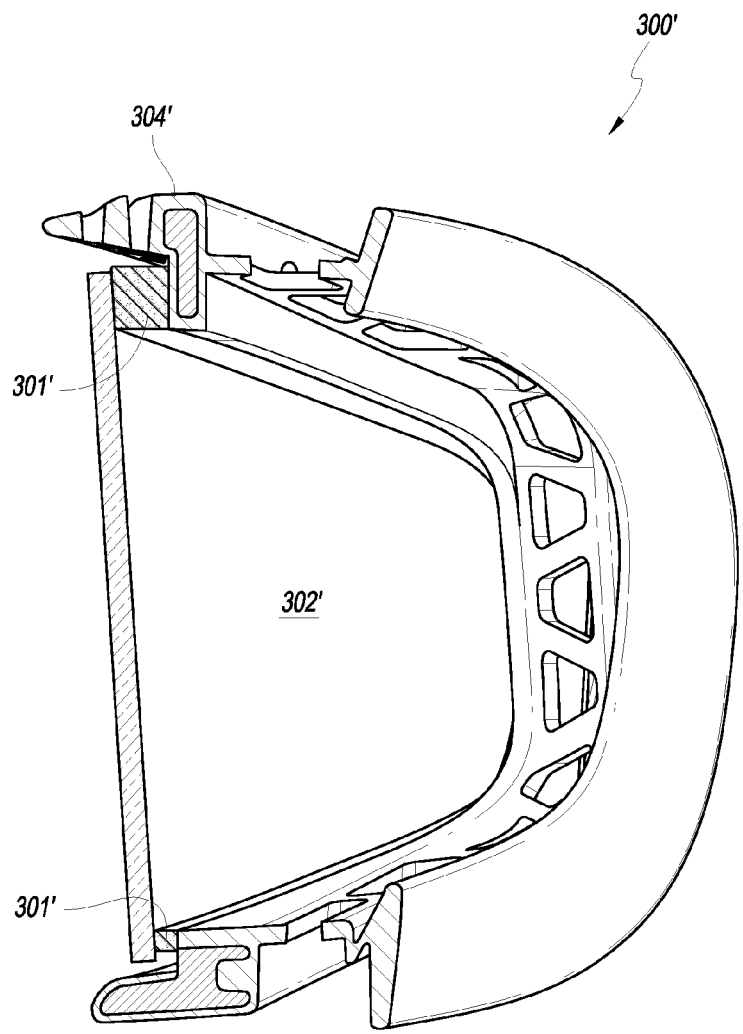
FIG. 40J is a cross-sectional view of an example embodiment of eyewear that provides filtered ventilation.
Figure 40K:
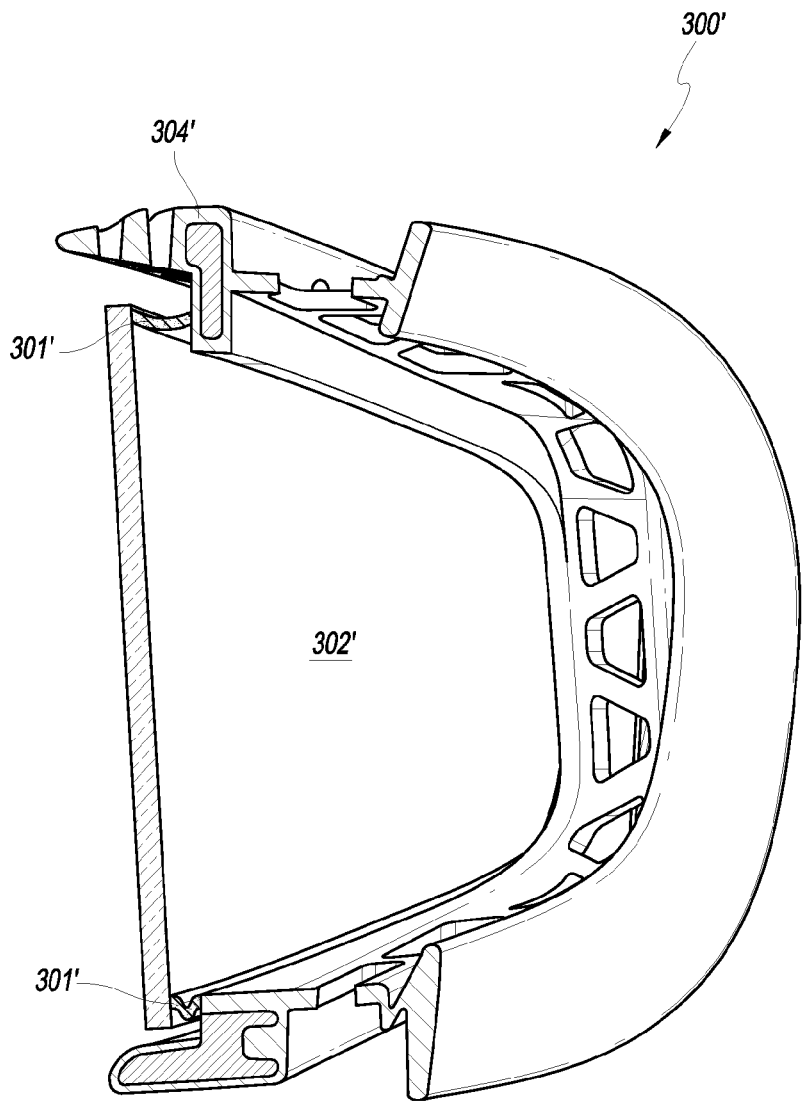
FIG. 40K is a cross-sectional view of an example embodiment of eyewear that provides filtered ventilation.

In some embodiments, the goggle 300' can provide for filtered ventilation. For example, in FIG. 40J, a filter 301' can be positioned between at least a portion of the gap between the frame 304' and the lens 302' when the lens 302' is in the open position. The filter 301' can be an air-permeable material, such as an open-cell foam. In some embodiments, the filter 301' can allow air to pass through while blocking dust and debris from entering the goggle 300'. The filter 301' can be coupled (e.g., adhered) to one or both of the frame 304' and the lens 302' to position the filter 301'. The filter 301' can extend only along an upper portion of the opening, or the filter 301' can extend across a majority or a substantial entirety of the opening between the frame 304' and the lens 302'. In some embodiments, the filter 301' can be compressible, so that when the lens 302' is in the closed position, the filter 301' can be compressed between the frame 304' and the lens 302'. As shown in FIG. 40J, the filter 301' can be flexible (e.g., so that it can fold when the lens 302' is moved to the closed position).

Figure 41:
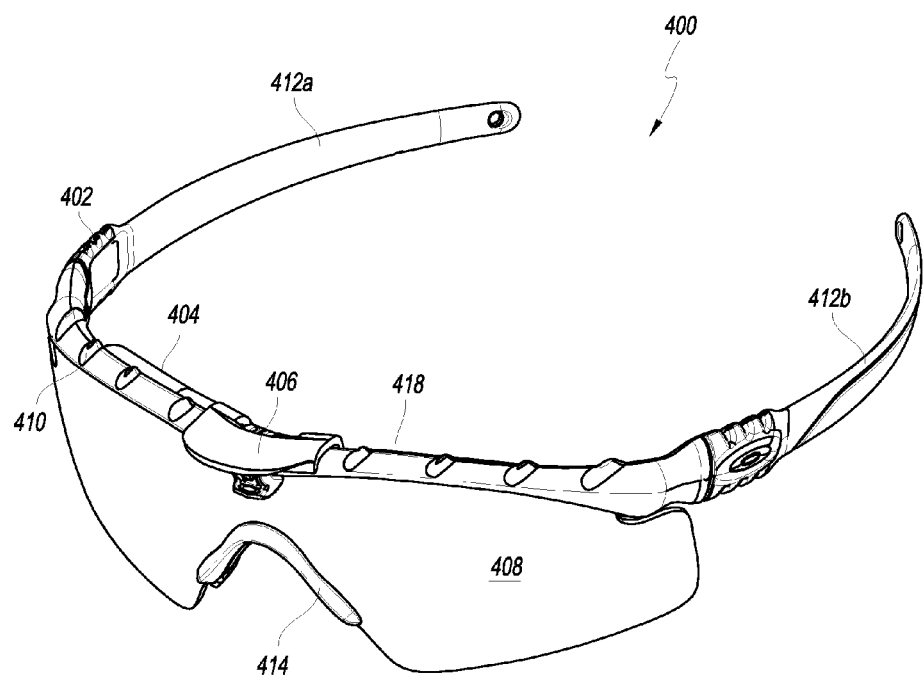
FIG. 41 is a front perspective view of an example embodiment of eyewear that includes a removable gasket.
Figure 42:
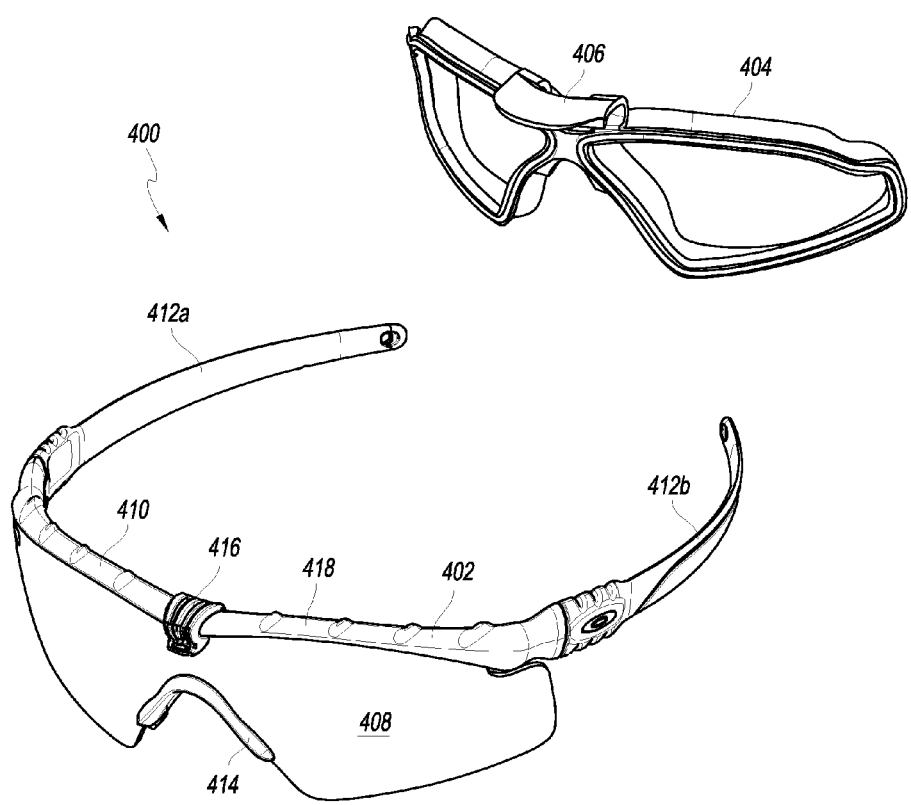
FIG. 42 shows an exploded front perspective view of the eyewear of FIG. 41, in which the gasket is disengaged from the eyeglass.
Figure 43:
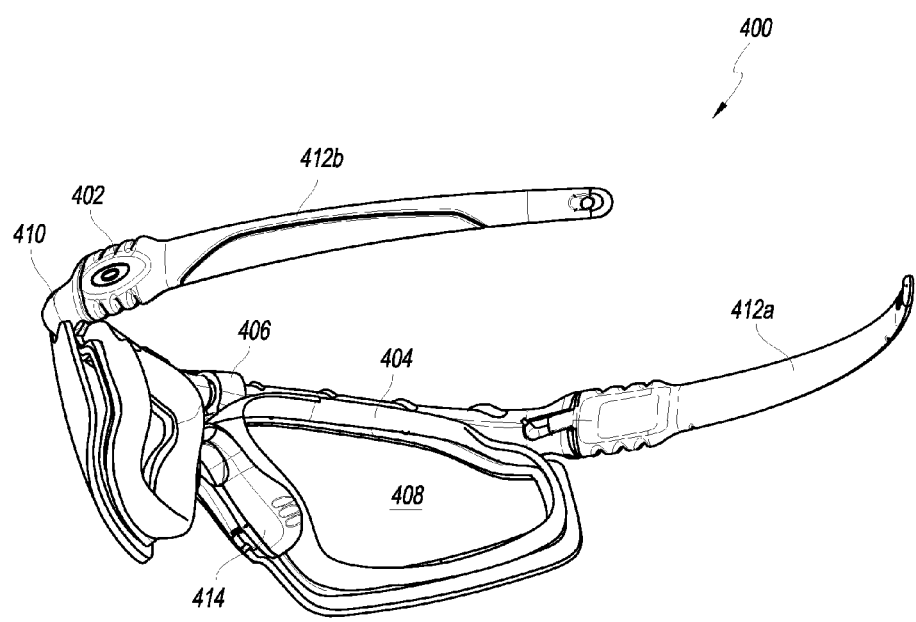
FIG. 43 is a rear perspective view of the eyewear of FIG. 41, in which the gasket is attached to the eyeglass.
Figure 44:
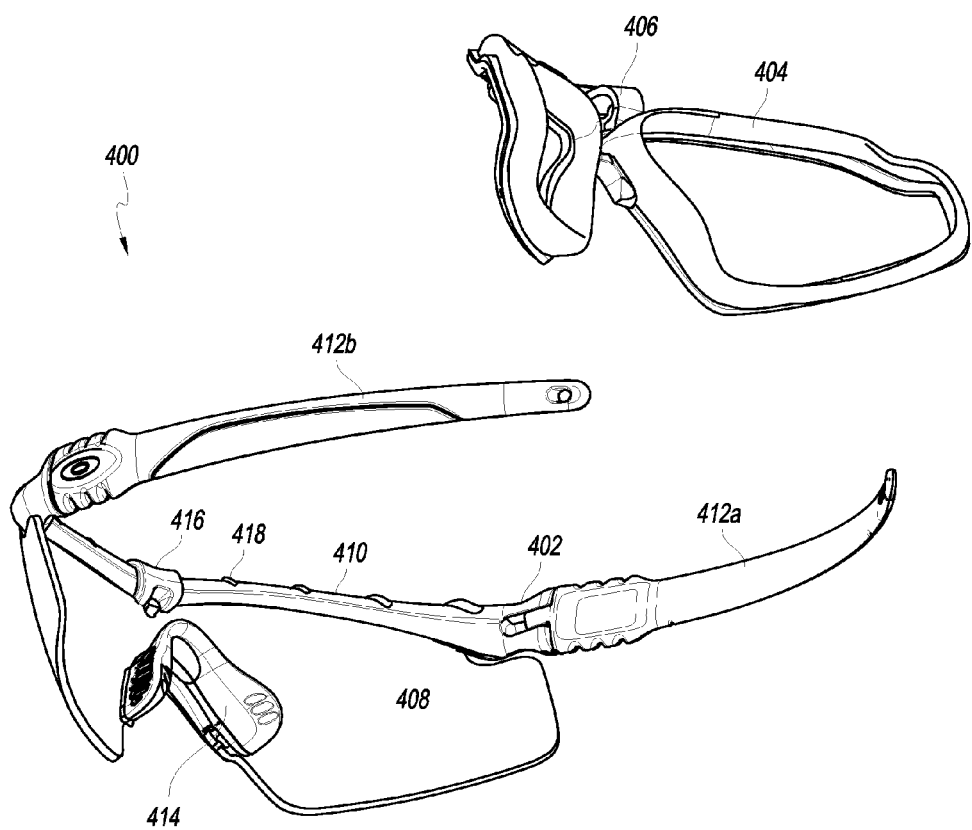
FIG. 44 is an exploded rear perspective view of the eyewear of FIG. 41, in which the gasket is disengaged from the eyeglass.

FIG. 41 is a front perspective view of an example embodiment of eyewear 400 that includes a removable gasket 404 (also referred to herein as an eyewear attachment). The eyewear 400 can include an eyeglass 402, and the gasket 404 can be removably attached to the eyeglass 402. FIG. 42 shows an exploded front perspective view of the eyewear 400, in which the gasket 404 is disengaged from the eyeglass 402. FIG. 43 is a rear perspective view of the eyewear, in which the gasket 404 is attached to the eyeglass 402. FIG. 44 is an exploded rear perspective view of the eyewear 400, in which the gasket 404 is disengaged from the eyeglass 402. Various features of the eyewear 400 can be similar to, or the same as, the other eyewear embodiments disclosed herein.

The eyeglass 402 can include a lens 408 and a frame 410 configured to position the lens 408 in the line of sight of a wearer. The eyeglass 402 can include ear stems 412a and 412b and a nose piece 414 to support the eyeglass 402 on the wearer's face. Although the eyeglass 402 is shown having a single lens 408 that is configured to extend over both eyes of the wearer, the eyeglass 402 can have two lenses. In some embodiments, the eyeglass 402 can include a lens retaining member 416 that can be configured to removably secure the lens 408 to the frame 410, thereby allowing the wearer to interchange the lens 408 of the eyeglass 402. For example, the lens 408 can be interchanged for a different lens if the lens 408 become damaged or dirty, and the lens 408 can be interchanged for a different lens having different optical properties depending on the conditions of use. The lens retaining member 416 can be configured to retain the lens 408 on the frame 410 in the event of impact to the lens 408 (e.g., a ballistic impact).

The eyeglass 402 can be configured to be wearable with or without the gasket 404. The gasket 404 can be attached to the eyeglass 402 to provide improved protection (e.g., from wind, dust, and debris) for the wearer's eyes. With the gasket 404 attached, the eyewear 400 can provide reduced ventilation as compared to the eyeglass 402 worn without the gasket 404. In some embodiments, the gasket 404 can be easily removed from the eyeglass 402 (e.g., without removal of the eyewear 400 from the wearer's face). With the gasket 404 removed, the eyewear 400 can have increased ventilation as compared to wearing the eyeglass 402 with the gasket 404 attached thereto. Thus, the wearer can attach the gasket 404 when additional protection is desired (e.g., in windy or dusty conditions), and the wearer can quickly remove the gasket 404 when additional ventilation is desired or when the additional protection is no longer needed. The eyewear 400 can be useful in various settings, including military settings in which the wearer may experience temporary conditions for which additional eye protection is desirable (e.g., jumping out of an aircraft or a dust storm). When the additional eye protection is no longer needed, the wearer can quickly remove the gasket 404 while continuing to wear the eyeglass 402. Because the gasket 404 can be removed quickly and with one hand, the wearer can remain focused on other tasks (e.g., on a combat situation) while removing the gasket 404. Because the gasket 404 can be removed without removing the eyeglass 402, the eyewear 400 can provide ballistic protection to the wearer's eyes during the removal of the gasket 404.

Figure 45:
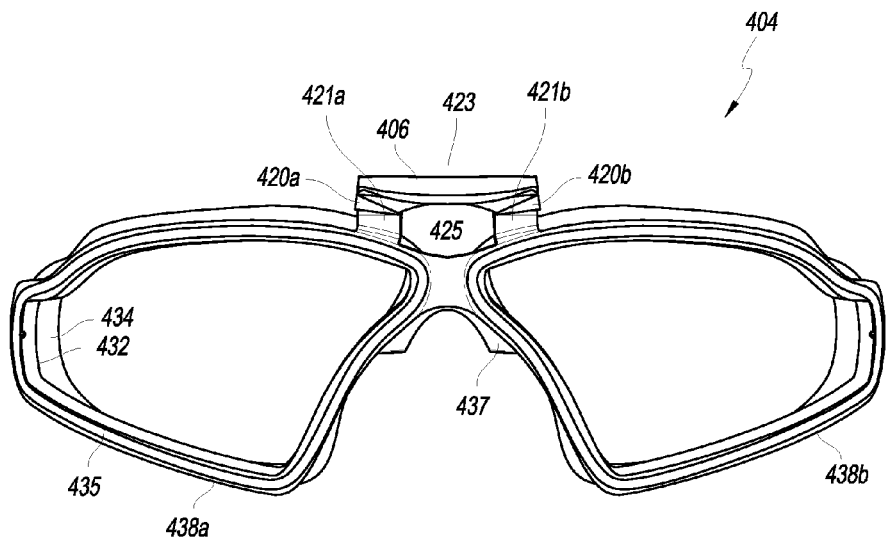
FIG. 45 is a front view of the gasket.
Figure 46:
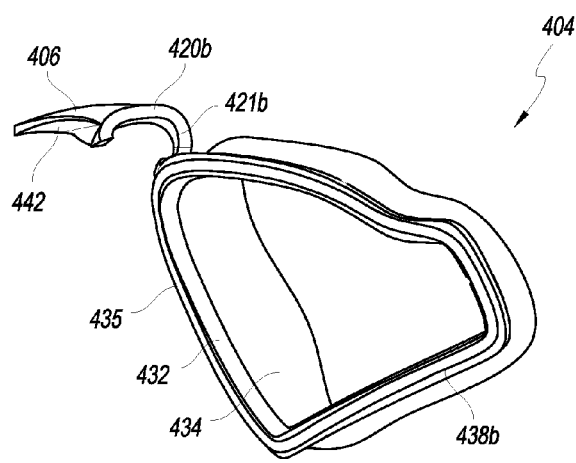
FIG. 46 is a side view of the gasket.

FIG. 45 is a front view of the gasket 404. FIG. 46 is a side view of the gasket 404. The gasket 404 can include a gasket retention member 406, which can be configured to removably couple to the gasket 404 to the eyeglass 402 (e.g., to the frame 410). The gasket retention member 406 can include one or more attachment mechanisms (e.g., one or more clips) that are configured to engage corresponding features on the eyeglass 402. For example, the gasket retention member 406 can include clips 420a and 420b that can be configured to engage the frame 410 of the eyeglass 402 (e.g., at a brow portion 418 of the frame 410). The clips 420a and 420b can have curved arms 421a and 421b with a shape that corresponds to the shape of an engagement area on the frame 410 (e.g., on the brow portion 418 of the frame 410). In some embodiments, the clips 420a and 420b can be positioned on either side of the lens retaining member 416 when attached to the eyewear 402, for example, such that the lens retaining member 416 is disposed in a gap 425 between the clips 420a and 420b. In some embodiments, the gasket retention member 406 can be positioned at the top of the gasket 404 (e.g., at the center of the gasket 404, such as above the brow portion of the gasket 404). The clips 420a and 420b can extend from the top surface of the subframe 432. The arms 421a and 421b of the clips 420a and 420b can be curved to correspond to the shape of the frame 410 that is engaged by the gasket retention member 406. For example, the arms 421a and 421b can have a generally hook shape (e.g., having a first portion extending generally upwardly from the subframe 432, a second portion extending generally forward, and a third portion that extends generally downwardly). The first clip 420a can be positioned on the right side of the gasket 404 (e.g., above the nasal portion of the right orbital 438a), and the second clip 420b can be positioned on the left side of the gasket 404 (e.g., above the nasal portion of the left orbital 438b). In some embodiments, clips (or other engagement features) can be positioned elsewhere on the gasket 404 in addition to, or instead of, the clips 420a and 420b. For example, additional clips can be added that engage the brow portion 418 of the eyeglass frame 410 at various positions along its length. In some embodiments, clips or other engagement features can be used to removably attach to the lens 408 (e.g., at the temples or bottom edges of the lens 408 or at any other suitable location along the periphery of the lens 408).

The gasket retention member 406 can include a grippable portion 442 (also referred to herein as a grip) that is configured to allow the user to grip the grippable portion 442 and pull the gasket 404 generally upwardly to disengage the gasket retention member 406 from the eyeglass 402 (e.g., by disengaging the clips 420a and 420b from the frame 410). The grippable portion 442 can extend forward from a bridge portion 423 that extends between the clips 420a and 420b, or the grippable portion 442 can form at least a portion of the bridge portion 423. For example, the bridge portion 423 and/or grippable portion 442 can extend generally horizontally between the clips 420a and 420b (e.g., between the forward portions of the arms 421a and 421b). The clips 420a and 420b can be spaced apart with an open space forming the gap 425 between the clips 420a and 420b. When the gasket 404 is attached to the frame 410 The lens retaining member 416 can be disposed between the clips 420a and 420b in the open space formed by the gap 425, thereby properly aligning the gasket 404 with the frame 410. If the frame 410 does not include specially shaped engagement portions that are configured to receive the clips 420a and 420b, the engagement between the gap 425 and the lens retaining member 416 can cause the clips 420a and 420b to engage the desired portion of the frame 410 to properly align the gasket 404 with the frame 410. Accordingly, the gasket 404 can be used with eyeglasses 402 that have a generally uniform frame shape without specially shaped engagement areas corresponding to the shape of arms 421a and 421b. Such gasket 404 can be especially beneficial in instances where specially shaped engagement areas on a frame are aesthetically undesirable or result in weak spots on the frame (e.g., for thin, indented engagement portions on the frame).

In operation, the user can attach the gasket 404 (or eyewear attachment) to the eyeglass 402 by holding the gasket 404 by the grip 442 and lowering the gasket 404 into the space between the eyeglass 402 and the wearer's face. The gasket 404 can be lowered until the gasket retention member 406 contacts the eyeglass 402 (e.g., the frame 410). The user can press downward (e.g., on the grip 442) to cause the gasket retentions member 406 to removably couple to the eyeglass 402. For example, the clips 420a and 420b can couple to the frame 410 when the user presses downward to attach the gasket 404. Thus, the user can attach the gasket 404 to the eyeglass 420 while the eyeglass 402 is being worn, without removing the eyeglass 402 from the wearer's face. The user can attach the gasket 404 to the eyeglass 402 with only one hand, which can be inside a glove, while the eyeglass 402 is being worn. In some embodiments, the wearer can remove the eyeglass 402 from the wearer's face and can attach the gasket 404 to the eyeglass 402 while the eyeglass 402 is not being worn. And the eyeglass 402 and gasket 404 together can be placed onto the wearer's face. As discussed herein, to remove the gasket 404 from the eyeglass 402, the wearer can press upward on the grip 442. Pressing upward on the grip 442 can cause the gasket retention member 406 to decouple from the eyeglass 402. For example, the clips 420a and 420b can decouple from the frame 410 when the user presses upward on the grip 442. The wearer can hold the grip 442 and lift the gasket 404 upward out of the space between the eyeglass 402 and the wearer's face. Thus, the wearer can remove the gasket 404 from the eyeglass 402 with only one hand, which can be inside a glove, while the eyeglass 402 is being worn, without removing the eyeglass 402 from the wearer's face. This can be advantageous for enabling the wearer to maintain protection of the eyes while removing the gasket 404.

Figure 47:
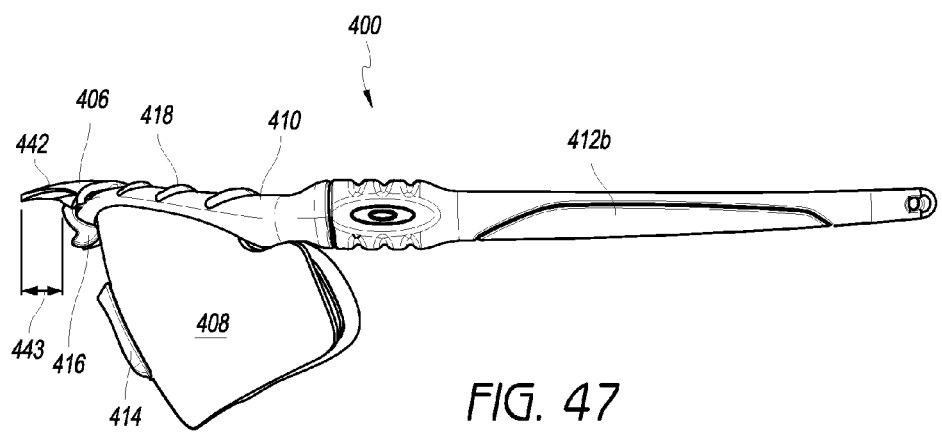
FIG. 47 is a side view of the eyewear with the gasket attached to the eyeglass.

As shown in FIG. 47, when the gasket 404 is coupled to the eyewear 402, the grippable portion 442 can extend forward past the end of the eyewear 402 (e.g., past the frame 410) by a distance 443 that allows the user to grip the grippable portion 442. The distance 443 can be at least about 3 mm and/or less than or equal to about 20 mm. The distance 443 can be at least about 5 mm and/or less than or equal to about 10 mm. In some embodiments, the distance 443 can be about 7 mm. The grippable portion 442 can also extend forward past the front of the clips 420a and 420b by the distance 443. Although a grippable portion 442 extending forward of the frame 410 may be aesthetically undesirable for eyewear that is worn for style, the grippable portion 442 can allow the wearer to remove the gasket 404 quickly and with one hand. In some embodiments, the gasket retention member 406 extends no more than about 5 mm, or no more than about 2 mm, or no more than about 1 mm above the top of the frame 410. This can enable the eyewear 400 to be worn with a helmet or other headwear and can facilitate removal of the gasket 404 while wearing a helmet or other headwear.

Figure 48:
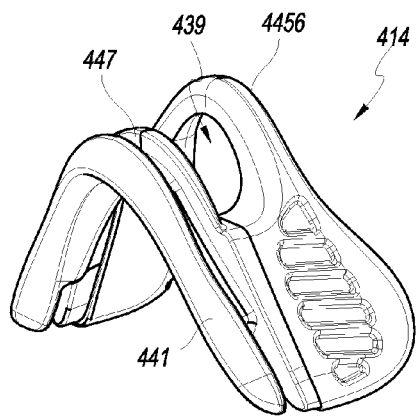
FIG. 48 is a perspective view of the nose piece of the eyewear of FIG. 41.
Figure 49:
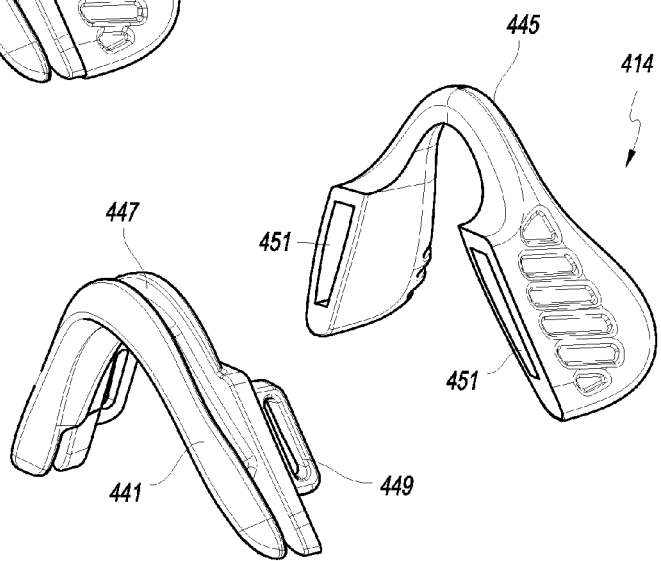
FIG. 49 is an exploded perspective view of the nose piece of FIG. 48.
Figure 50:
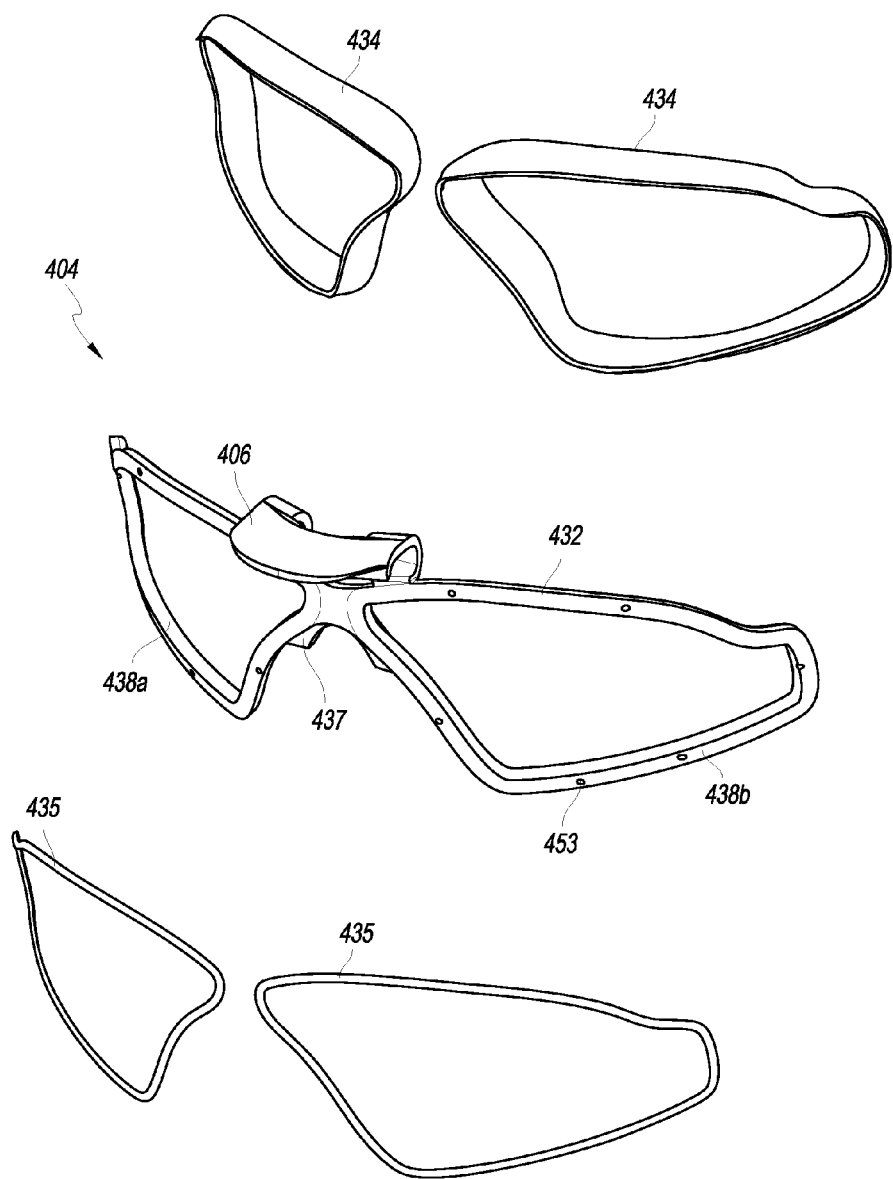
FIG. 50 is an exploded perspective view of an example embodiment of a gasket for use with the eyewear of FIG. 41.

In some embodiments, the gasket 404 can include a nose piece engagement member 437 that is configured to engage the nose piece 414, which can stabilize the attachment of the gasket 404 to the eyewear 402. As can be seen in FIG. 45, the nose piece engagement member 437 can have an arched projection that extends generally downwardly (e.g., from a bridge portion of the gasket 404). With reference to FIGS. 48 and 49, the nose piece 414 can have a recess 439 that is configured to receive the nose piece engagement member 437. The nose piece 414 can have a front member 441 and a rear member 445. The front member 441 can have a groove 447 for receiving the lens 408 to secure the nose piece 414 to the lens 408. The front member 441 can have engagement members 449 (e.g., tabs) that are configured to engage with engagement members 451 (e.g., slots) of the rear member 445, to couple the front member 441 to the rear member 445. In some embodiments, an adhesive can be used to couple the front member 441 to the rear member 445 in addition to or in lieu of the engagement members 449 and 451. The upper portions of the rear member 445 and the front member 441 can be spaced apart from each other when the rear member 445 is coupled to the front member 441, thereby forming a recess 439 therebetween. The recess 439 can be shaped to receive the nose piece engagement member 437 therein, as mentioned above. In some embodiments, the rear member 445 can be formed of a flexible material that that it can conform to the shape of the wearer's nose. In some embodiments, the front member 441 can be formed of a rigid, or semi-rigid material to facilitate the attachment between the lens 408 and the nose piece 414. In some embodiments, a single-piece nose piece can be used instead of the front and rear members 441 and 445 shown.

As can be seen in FIG. 45, the gasket 404 can include two orbitals 438a and 438b corresponding to the wearer's right and left eyes, respectively. In some embodiment, the orbitals 438a and 438b can be separately enclosed and can separate the unitary lens 408 into separately enclosed right-eye and left-eye portions. In some embodiments, the orbitals 438a and 438b can be joined to form a unitary opening that surrounds both the right and left eyes. The gasket 404 can include a subframe 432, a flange 434 (also referred to herein as a face flange) disposed rearward of the subframe 432, and a front seal 435 disposed forward of the subframe 432. The subframe 432 can be formed of a rigid or semi-rigid material (e.g., glass-filled polypropylene or polybutylene terephthalate (PBT)). The face flange 434 can be formed of a flexible material can be configured to conform to the shape of the wearer's face. The front seal 435 can be formed of a flexible material and can be configured to abut against the lens 408 (e.g., the back surface of the lens 408) to form a seal between the lens 408 and at least a portion of the orbitals 438a and 438b. In some embodiments, the front seal 435 can contact the back surface of the lens 408 at locations that are offset inwardly from the periphery of the lens 408 (e.g., by a distance of at least about 1 mm and/or less than or equal to about 7 mm). In some embodiments, the flexible material can be a thermoplastic elastomer (TPE) or a self-bonding silicone material. In some embodiments, the front seal 435 can include right and left portions which can be separated or joined, and which correspond to the right and left orbitals 438a and 438b, respectively. In some embodiments, the face flange 434 can include right and left portions which can be separated or joined, and which correspond to the right and left orbitals 438a and 438b, respectively.

Figure 51:
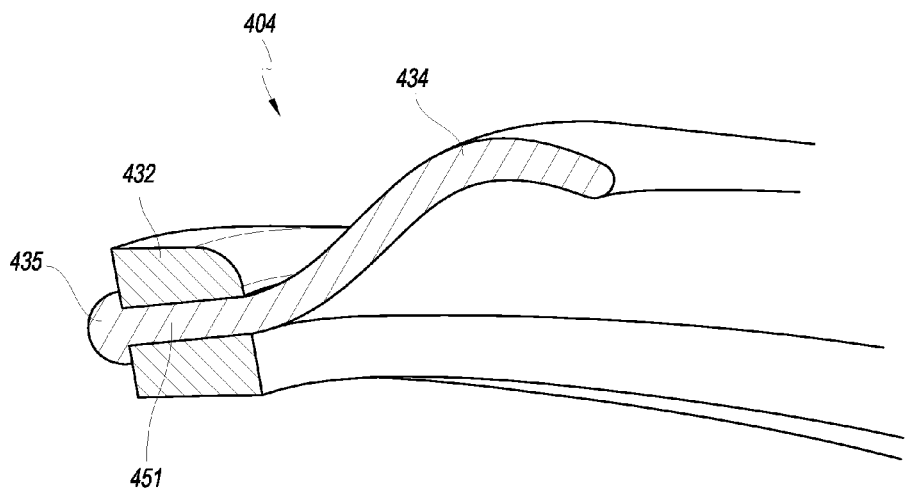
FIG. 51 is a partial cross-sectional view of the gasket of FIG. 50.
Figure 52:
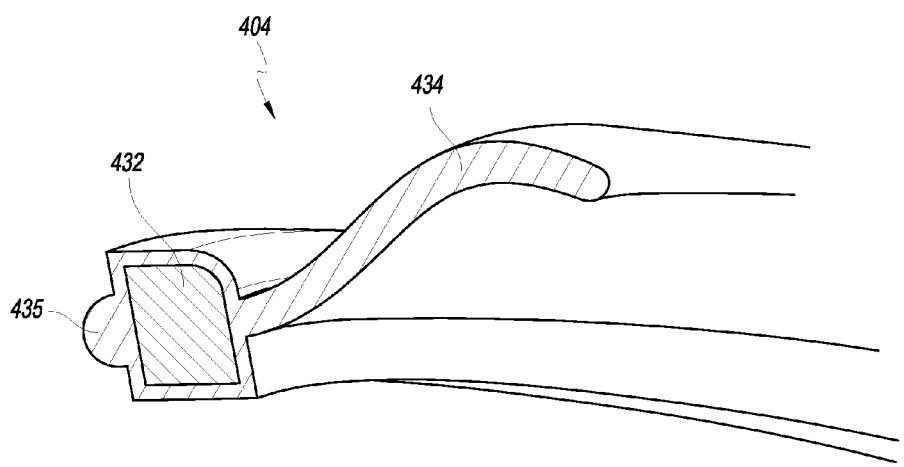
FIG. 52 is a partial cross-sectional view of another example embodiment of a gasket.

In some embodiments, the front seal 435 can be attached to, or integrally formed with, the face flange 434, which can facilitate the securing of the front seal 435 and face flange 434 to the subframe 432. For example, in some embodiments, the flexible material can extend from the front seal 435 to the face flange 434. In some embodiments, the subframe 432 can include holes 453 that extend therethrough. As shown in FIG. 51, the flexible material can extend through the holes 453 to interconnect the front seal 435 to the face flange 434. In some embodiments, the flexible material can extend around the outside of the subframe 432 to interconnect the front seal 435 to the face flange 434, as can be seen in FIG. 52. In some embodiments, the front seal 435 can be separate from the face flange 434. In some embodiments, the front seal 435 and/or the face flange 434 can be coupled to the subframe 432 by and adhesive or other attachment mechanism.

Figure 53:
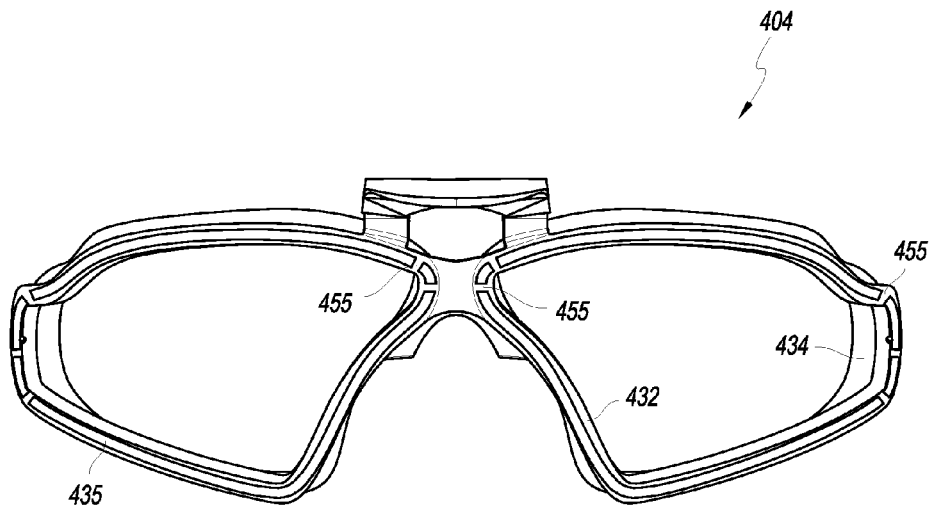
FIG. 53 is a front view of an example embodiment of a gasket having gaps configured to provide ventilation for the eyewear.
Figure 54:
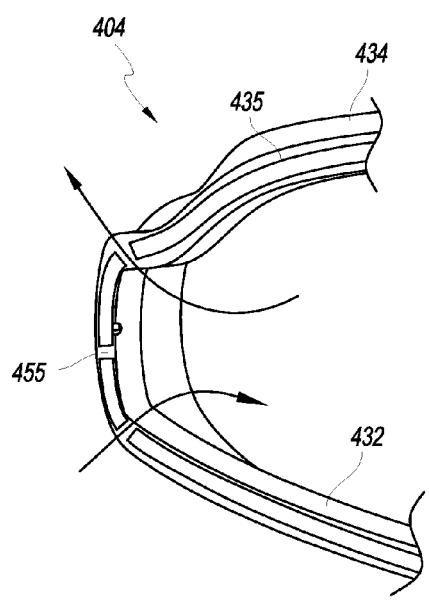
FIG. 54 is a detailed partial front view of the gasket of FIG. 53.

In some embodiments, the gasket 404 can be vented to allow exchange of air between the interior of the eyewear 400 and the outside area when the gasket 404 worn attached to the eyeglass 402. As shown in FIGS. 53 and 54, the front seal 435 can have gaps 455 that allow air to pass between the interior of the eyewear 400 and the surrounding area. As shown in FIG. 53, the gaps 455 can be located at the temple portions of the gasket 404 and/or at the medial or nasal portions of the gasket 404. Various other configurations are possible. For example, in some embodiments, the gaps 455 can be dispersed around the full circumference of the orbitals 438a and 438b. In some embodiments, the gasket 404 can include lower gaps formed on a lower portion of the gasket 404 (e.g., as gaps in the front seal 435) and upper gaps formed on an upper portion of the gasket 404 (e.g., as gaps in the front seal 435) so that the lower gaps and upper gaps cooperate for produce a chimney effect that draws fresh air into the eyewear 400 from the bottom and expels air from the eyewear 400 from the top thereof.

The ventilation provided by the gasket 404 can reduce or prevent fogging on the interior of the eyewear 400. As discussed above, the gasket 404 can be configured to be easily and quickly removable in the event that the ventilation provided by the gaps 455 is insufficient to prevent fogging. In some embodiments, the front seal 435 can form a seal between the lens 408 and a majority of the orbitals 438a and 438b (e.g., forming a seal at substantially all portions of the orbital except at the gaps 455). For example, the front seal 435 can form a seal between the lens 408 and at least about 80%, at least about 90%, or at least about 95% of the orbitals 438a and 438b. In some embodiments, the gaps 455 can cause the front seal 435 to form a seal between the lens 408 and less than or equal to about 98%, less than or equal to about 95%, less than or equal to about 93%, or less than or equal to about 90%, of the orbitals 438a and 438b. In some embodiments, the face flange 434 and/or the subframe 432 can include gaps (not shown) that provide ventilation similar to the gaps 455 discussed herein.

In some embodiments, the seal between the wearer's face and the gasket 404 (e.g., the face flange 434) can be more important than the seal formed between the lens 408 and the gasket 404 (e.g., the front seal 435) for protecting the wearer's face from dust and debris. Thus, the front seal 435 can form a seal between the lens 408 and the orbitals 438a and 438b of less than the values disclosed above. The face flange 434 can be formed of a flexible material that is configured to conform to the face of the wearer. Although a single orbital can be used in some embodiments, the use of two orbitals 438a and 438b with a face flange 434 having right and left portions that correspond to the two orbitals 438a and 438b can facilitate sealing of the gasket 404 against the wearer's face. For example, the right and left portions of the face flange 434 can be separately enclosed so that if the seal is compromised for one side, the other side can remain sealed. Also, the use of a face flange 434 having separate portions for the two orbitals 328a and 438b can reduce the occurrence of leakage around the nose portion, as compared to a face flange that extends across a user's nose.

In some embodiments, the subframe 432, the face flange 434, and/or the front seal 435 can include an open-cell foam or other porous material that allows air exchange between the interior of the eyewear 400 and the surrounding area. For example, the venting gaps formed in the face flange 434, the subframe 432, and/or the front seal 435 can be covered and/or filled with the open-cell foam or other porous material. In some embodiments, the foam or other material can allow air to pass therethrough while substantially preventing dust or other debris from passing therethrough, thereby providing ventilation while also providing protection from dust and debris. In some embodiments, an anti-fogging coating can be applied to the interior of the eyewear 400 (e.g., to the eyeglass 402 and/or to the gasket 404) to reduce or prevent moisture fogging. Various types of anti-fogging coatings can be used (e.g., moisture absorption coatings, moisture sheer coatings, coatings based on urethanes, and/or coatings based on treated polysiloxanes).

Figure 55:
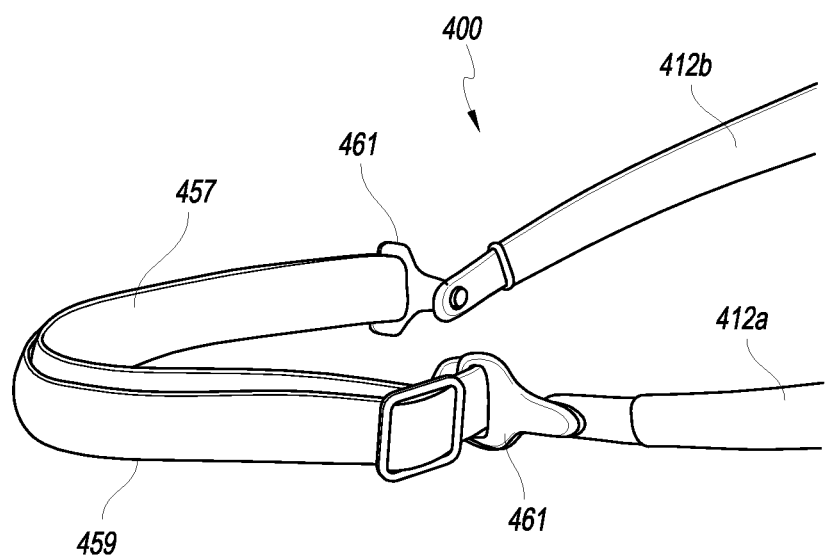
FIG. 55 is a partial perspective view of eyewear that includes a leash.

With reference to FIG. 55, in some embodiments, the eyewear 400 (and the other eyewear embodiments disclosed herein) can include a leash 457 that can extend between the ear stems 412a and 412b to aid in holding the eyewear 400 on the wearer. The lease 457 can include a strap 459, which can be adjustable in length. The strap 459 can be coupled to end pieces 461, which can be pivotally attached to the ear stems 412a and 412b (e.g., at the rear ends thereof). In some embodiments, the leash 457 can be configured to hold the eyewear 400 against the wearer's face such that the wearer's face presses the gasket 404 against the eyeglass 402 to facilitate the formation of a seal between the gasket 404 and the eyewear 402. In some embodiments, the gasket 404 can be configured to seal against the eyewear 402 without the leash 457, and the leash can be omitted.

Although embodiments have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed embodiments.

What is claimed is:

1. Eyewear comprising:
a lens;
a frame configured to support the lens in a field of view of a wearer; and
a lens retaining member coupled to a brow portion of the frame, wherein the lens retaining member is rotatable between a closed position and an open position;
wherein the closed position of the lens retaining member retains the lens on the frame in a closed configuration configured to be in the field of view of the wearer;
wherein the open position of the lens retaining member retains the lens on the frame in an open configuration also configured to be in the field of view of the wearer, and wherein the open configuration of the lens provides more ventilation through the eyewear than the closed configuration of the lens.

2. The eyewear of claim 1, wherein the lens retaining member comprises a back arm disposed rearward of the lens and configured to push the lens to the open configuration when the lens retaining member is moved to the open position.

3. The eyewear of claim 1, wherein the lens retaining member comprises a front arm disposed forward of the lens and configured to push the lens to the closed configuration when the lens retaining member is moved to the closed position.

4. The eyewear of claim 1, wherein the lens retaining member comprises one or more positioning features configured to engage one or more corresponding features on the frame to maintain the lens retaining member in the closed position.

5. The eyewear of claim 1, wherein the eyewear is a goggle that comprises a flexible flange configured to rest against and conform to the face of the wearer.

6. The eyewear of claim 1, wherein the lens substantially seals against the frame when the lens is in the closed configuration.

7. The eyewear of claim 1, wherein the lens comprising one or more tabs, wherein the frame comprising one or more grooves configured to receive the one or more tabs therein, and wherein the tabs slide within the grooves when the lens moves between the closed configuration and the open configuration.

8. The eyewear of claim 1, wherein the frame comprises a first lateral side and a second lateral side, and wherein the brow portion extends between the first and second lateral sides.

9. The eyewear of claim 1, wherein the lens retaining member is substantially centered on the brow portion of the frame.

10. The eyewear of claim 1, wherein the frame comprises:
a nose portion, wherein the lens in the open position is spaced apart from the nose portion of the frame such that a linear line extends from a location outside the eyewear, between the nose portion and the lens, and to a location inside the eyewear that is rearward of the frame; and at least one ridge disposed between the nose portion of the frame and the lens, the at least one ridge intersecting the linear line.

11. The eyewear of claim 10, wherein the at least one ridge is configured such that, when the lens is in the open position, all of one or more openings between the lens and the nose portion of the frame through which a linear line extends from a location outside the eyewear to a location inside the eyewear and rearward of the frame have a width of about 1.5 mm or less.

12. The eyewear of claim 10, wherein the nose portion comprises one or more openings extending through the nose portion and configured increase ventilation through the eyewear when the lens is in the open position.

13. The eyewear of claim 12, wherein the nose portion comprises a plurality of ridges and the one or more openings are disposed between the plurality of ridges.

14. The eyewear of claim 10, wherein the brow portion of the frame comprises a plurality of openings, wherein the plurality of openings in the brow portion are in communication with the inside of the eyewear to provide ventilation when the lens is in the open position, and wherein the plurality of openings in the brow portion are not in communication with the inside of the eyewear when the lens is in the closed position.

15. Eyewear comprising:
a lens;
a frame configured to support the lens in a field of view of a wearer, wherein the lens is movable with respect to the frame between a closed position and an open position, wherein the lens is configured to be in the field of view of the wearer in the open position and in the closed position, wherein the open position provides more ventilation through the eyewear than the closed position; and
a lens retaining member configured to toggle the lens between the closed position and the open position, wherein the lens retaining member is rotatable between a first position associated with the closed position of the lens and a second position associated with the open position of the lens;
wherein the lens retaining member is configured to impede the lens from moving from the closed position to the open position in response to a force pushing the lens toward the open position.

16. The eyewear of claim 15, wherein the lens retaining member comprises:

a front arm positioned forward of the lens when the lens is in the closed position, wherein the lens applies a force on the front arm when the lens is pushed toward the open position; and one or more positioning features on a first side of the lens retaining member, the one or more positioning features configured to engage one or more corresponding features on the frame when the lens is in the closed position;

wherein the front arm is coupled to the one or more positioning features at a junction on a second side of the lens retaining member such that the force applied to the front arm by the lens imparts a force on to the one or more positioning features in a direction that further secures the lens in the closed position.

17. The eyewear of claim 16, wherein the second side of the lens retaining member is substantially opposite the first side of the lens retaining member.

18. The eyewear of claim 16, wherein the one or more positioning features are on a front side of the lens retaining member and wherein the junction is on a back side of the lens retaining member.

19. The eyewear of claim 16, wherein the one or more positioning features comprise hooks, and wherein the one or more corresponding features on the frame comprise teeth.

20. The eyewear of claim 15, wherein the lens retaining member comprises:
one or more positioning features configured to engage one or more corresponding features on the frame when the lens is in the closed position; and
a locking element configured such that the force that pushes the lens toward the open position causes the locking element to press against the one or more positioning features to impede the one or more positioning features from disengaging from the one or more corresponding features on the frame so as to impede the lens from moving from the closed position to the open position.

21. The eyewear of claim 20, wherein the lens retaining member comprises a front arm positioned forward of the lens when the lens is in the closed position, and wherein the locking element is disposed on a front side of the front arm.

22. The eyewear of claim 15, wherein the lens retaining member is movable between the first position associated with the closed position of the lens, the second position associated with the open position of the lens, and a releasing position configured to enable the lens to be removed from the frame.

* * * * *